US007262268B2

(12) United States Patent
Morytko et al.

(10) Patent No.: US 7,262,268 B2
(45) Date of Patent: Aug. 28, 2007

(54) LIPOPEPTIDE STEREOISOMERS, METHODS FOR PREPARING SAME, AND USEFUL INTERMEDIATES

(75) Inventors: Michael Morytko, Framingham, MA (US); Yanzhi Zhang, Sharon, MA (US); Michael Jung, Los Angeles, CA (US); John Finn, Stow, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 346 days.

(21) Appl. No.: 10/213,218

(22) Filed: Aug. 6, 2002

(65) Prior Publication Data

US 2003/0096948 A1 May 22, 2003

Related U.S. Application Data

(60) Provisional application No. 60/310,313, filed on Aug. 6, 2001.

(51) Int. Cl.
*A61K 38/12* (2006.01)
(52) U.S. Cl. ..................................................... 530/317
(58) Field of Classification Search ...................... None
See application file for complete search history.

(56) References Cited

U.S. PATENT DOCUMENTS

| 4,399,067 A | 8/1983 | Debono ................... 260/112.5 |
|---|---|---|
| 4,482,487 A | 11/1984 | Abbott et al. ............ 260/112.5 |
| 4,524,135 A | 6/1985 | Abbott et al. .................. 435/69 |
| 4,537,717 A | 8/1985 | Abbott et al. ............ 260/112.5 |
| RE32,310 E | 12/1986 | Debono ....................... 530/317 |
| RE32,311 E | 12/1986 | Debono ....................... 530/317 |
| RE32,333 E | 1/1987 | Hamill et al. ................ 530/321 |
| RE32,455 E | 7/1987 | Hamill et al. ................ 530/317 |
| 4,800,157 A | 1/1989 | Eaton et al. .................... 435/71 |
| 4,874,843 A | 10/1989 | Baker .......................... 530/317 |
| 4,885,243 A | 12/1989 | Huber et al. ................. 435/71.3 |
| 5,573,936 A | 11/1996 | Kreuzman et al. ........... 435/196 |
| 5,629,288 A | 5/1997 | Lattrell et al. |
| 5,912,226 A | 6/1999 | Baker et al. ..................... 514/9 |
| 6,794,490 B2 * | 9/2004 | Hill et al. .................... 530/317 |
| 2002/0025924 A1 * | 2/2002 | Hill et al. .................... 530/317 |
| 2002/0028771 A1 | 3/2002 | Curran et al. .................... 514/9 |
| 2003/0083240 A1 | 5/2003 | Finn |
| 2004/0067878 A1 * | 4/2004 | Hill et al. .................... 530/317 |

FOREIGN PATENT DOCUMENTS

| EP | 0885957 | 12/1998 |
|---|---|---|
| WO | WO 01/44271 | 12/2000 |
| WO | WO 01/44272 | 12/2000 |
| WO | WO 01/44274 | 12/2000 |
| WO | WO 01/53330 | 1/2001 |
| WO | WO 01/05837 | 7/2001 |

OTHER PUBLICATIONS

Tilmann B. Walk et al., "Identification of Unusual Amino Acids in Peptides Using Automated Sequential Edman Degradation Coupled to Direct Detection by Electrospray-Ionization Mass Spectrometry", 1999 vol. 49, 329-340.
Richard H. Baltz, "Lipopeptide Antibiotics Produced by *Streptomyces roseosporus* and *Streptomyces fradiae*", Biotechnology of Antibiotics, Chapter 14, pp. 415-435.
F.M. Huber et al., "The formation of daptomycin by supplying decanoic acid to *Streptomyces roseosporus* cultures producing the antibiotic complex A21978C", Journal of Biotechnology, 7 (1988) 283-292.
M. Debono et al., Synthesis of New Analogs of Echinocandin B by Enzymatic Deacylation and Chemical Reacylation of the Echinocandin B Peptide: Synthesis of the Antifungal Agent Cilofungin (LY121019), The Journal of Antibiotics, vol. XLII No. 3, pp. 389-397 (Aug. 1, 1988).
LaVerne D. Boeck et al., "Deacylation of A21978C, An Acidic Lipopeptide Antibiotic Complex, by *Actinoplanes Utahensis*", The Journal of Antibiotics, vol. XLI No. 8, pp. 1085-1092 (Mar. 7, 1988).
Junji Inokoshi et al., "Cloning and sequencing of the aculeacin A acylase-encoding gene from *Actinoplanes utahensis* and expression in *Streptomyces lividans* ", Gene, 119 (1992) 29-35.
F.M. Huber et al., "The Synthesis of A21978C Analogs by *Streptomyces Roseosporus* Cultivated Under Carbon Limitation and Fed Fatty Acids", Biotechnology Letters vol. 12, No. 11, 789-792 (1990).
Junji Inokoshi et al., "Efficient production of aculeacin A acylase in recombinant *Streptomyces* strains", Applied Micribiology and Biotechnology (1993) 39:532-536.
Mauel Debono et al., "Enzymatic and Chemical Modifications of Lipopeptide Antibiotic A21978C: The Synthesis and Evaluation of Daptomycin (LY146032)", The Journal of Antibiotics, vol. XLI No. 8, pp. 1093-1105.
Kia-Ki Han et al., "Current Developments in Stepwise Edman Degradation of Peptides and Proteins", Int. J. Biochem, vol. 17 No. 4, pp. 429-445, 1985.
A.J. Kreuzman et al., "Membrane-associated echinocandin B deacylase of *Actinoplanes utahensis:* purification, characterization, heterologous cloning and enzymatic deacylation reaction", Journal of Industrial Microbiology & Biotechnology (2000) 24, 173-180.

* cited by examiner

*Primary Examiner*—Cecilia Tsang
*Assistant Examiner*—Roy Teller
(74) *Attorney, Agent, or Firm*—Timothy J. Douros; Jill M. N. Mandelblatt

(57) ABSTRACT

The present invention provides daptomycin stereoisomeric compounds, methods and intermediates for preparing daptomycin and daptomycin stereoisomoeric compounds, as well as pharmaceutical compositions of these compounds and methods of using these compositions as antibacterial agents.

7 Claims, No Drawings

LIPOPEPTIDE STEREOISOMERS, METHODS FOR PREPARING SAME, AND USEFUL INTERMEDIATES

CROSS-REFERENCE TO RELATED APPLICATIONS

This application claims the benefit of U.S. Provisional Application No. 60/310,313, filed Aug. 6, 2001, which is hereby incorporated by reference in its entirety.

FIELD OF THE INVENTION

The present invention relates to a process for preparing daptomycin and novel daptomycin stereoisomoeric compounds. The invention also relates to novel daptomycin stereoisomeric compounds, pharmaceutical compositions of these compounds and methods of using these compounds as antibacterial agents.

BACKGROUND OF THE INVENTION

The rapid increase in the incidence of gram-positive infections—including those caused by resistant bacteria—has sparked renewed interest in the development of novel classes of antibiotics. A class of compounds which have shown potential as useful antibiotics includes the A-21978C lipopeptides described in, for example, United States Patents RE 32,333; RE 32,455; RE 32,311; RE 32,310; U.S. Pat. Nos. 4,482,487; 4,537,717; and 5,912,226 and U.S. patent applications Ser. Nos. 09/738,742; 09/737,908; and 09/739,535 filed Dec. 15, 2000.

Daptomycin, a member of the A-21978C lipopeptides, is described by Baltz in *Biotechnology of Antibiotics, 2nd Ed.*, ed. W. R. Strohl (New York: Marcel Dekker, Inc.), 1997, pp. 415–435. Daptomycin, also referred to as LY 146032, has an n-decanoyl side chain linked to the N-terminal tryptophan of a three-amino acid chain, which is linked to a cyclic 10-amino acid peptide. The reported structure (see, e.g., U.S. Pat. No. 4,537,717) of daptomycin is shown below:

Daptomycin has potent bactericidal activity in vitro and in vivo against clinically relevant gram-positive bacteria that cause serious and life-threatening diseases. These bacteria include resistant pathogens, such as vancomycin-resistant enterococci (VRE), methicillin-resistant *Staphylococcus aureus* (MRSA), glycopeptide intermediate susceptible *Staphylococcus aureus* (GISA), coagulase-negative staphylococci (CNS), and penicillin-resistant *Streptococcus pneumoniae* (PRSP), for which there are few therapeutic alternatives. See, e.g., Tally et al., 1999, *Exp. Opin. Invest. Drugs* 8:1223–1238.

Despite the promise that existing antibacterial agents have shown, the need for novel antibiotics continues. Many pathogens have been repeatedly exposed to commonly-used antibiotics. This exposure has led to the selection of variant antibacterial strains resistant to a broad spectrum of antibiotics. The loss of potency and effectiveness of an antibiotic caused by resistant mechanisms renders the antibiotic ineffective and consequently can lead to some life-threatening infections that are virtually untreatable. As new antibiotics come to market pathogens may develop resistance or intermediate resistance to these new drugs, effectively creating a need for a stream of new antibacterial agents to combat these emerging strains. In addition compounds that exhibit bactericidal activity offer advantages over present bacteriostatic compounds. Thus, novel synthetic antibacterial agents would be expected to be useful to treat not only "natural" pathogens, but also intermediate drug resistant and drug resistant pathogens because the pathogen has never been exposed to the novel antibacterial agent. New antibacterial agents may exhibit differential effectiveness against different types of pathogens.

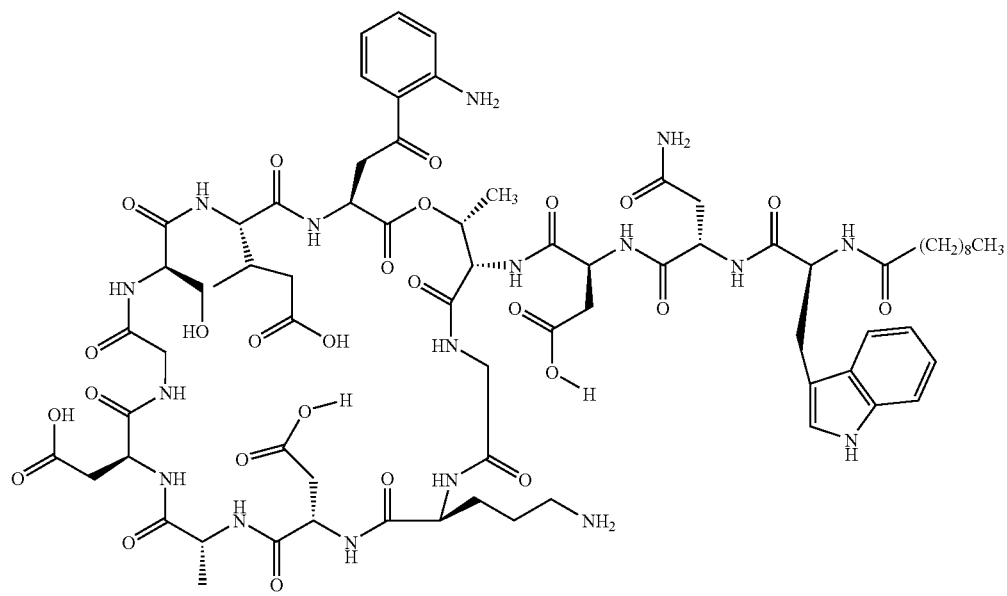

(I)

Known processes for the production of daptomycin involve the fermentation of *Streptomyces roseosporus* resulting in the formation of daptomycin as a single stereoisomer (see, for example, United States Patents RE 32,333; RE 32,455; RE 32,311; U.S. Pat. Nos. 4,482,487; 4,537,717; 4,800,157, 4,874,843; 4,885,243 and 5,912,226). Stereoisomers of daptomycin and processes for the production of these stereoisomers have not been reported. New processes that allow for the preparation of a variety of daptomycin stereoisomeric compounds would therefore be advantageous.

SUMMARY OF THE INVENTION

The present invention provides stereoisomeric compounds, and methods of preparing such stereoisomeric compounds, as well as intermediates useful for preparing such stereoisomeric compounds.

In one embodiment, the invention provides the following stereoisomer compounds:

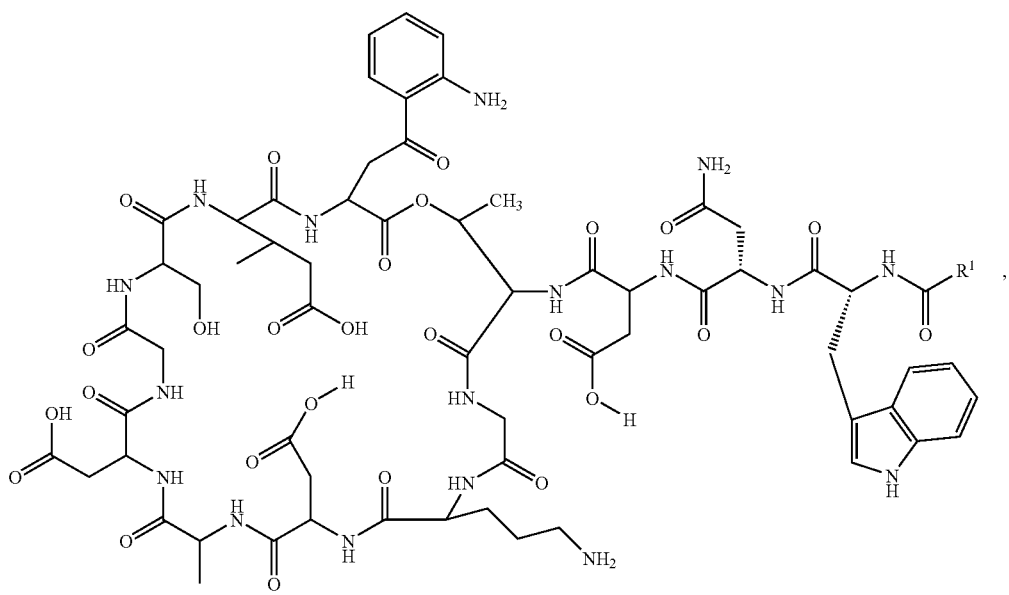

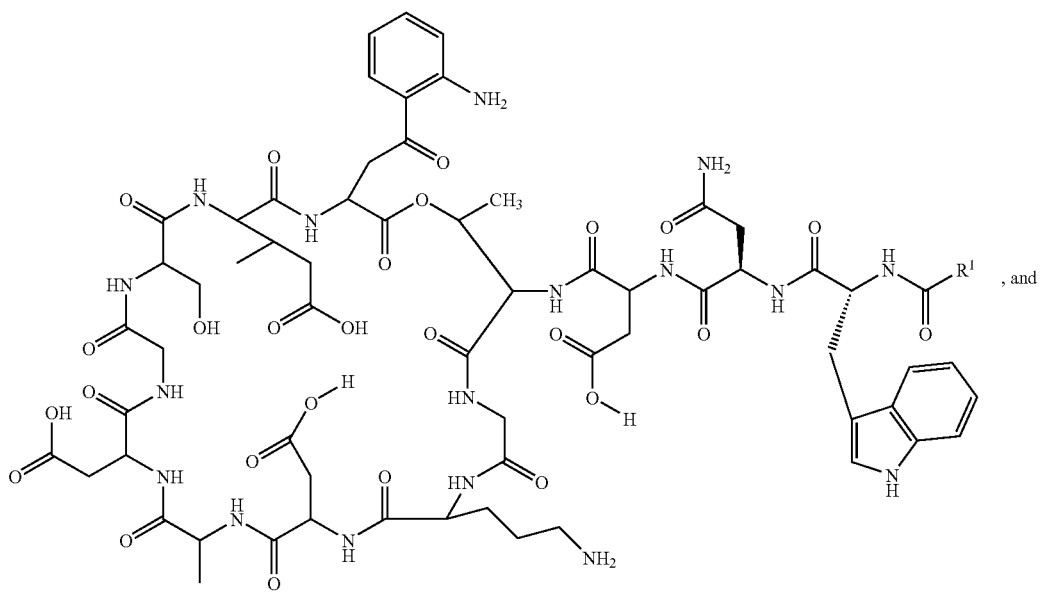

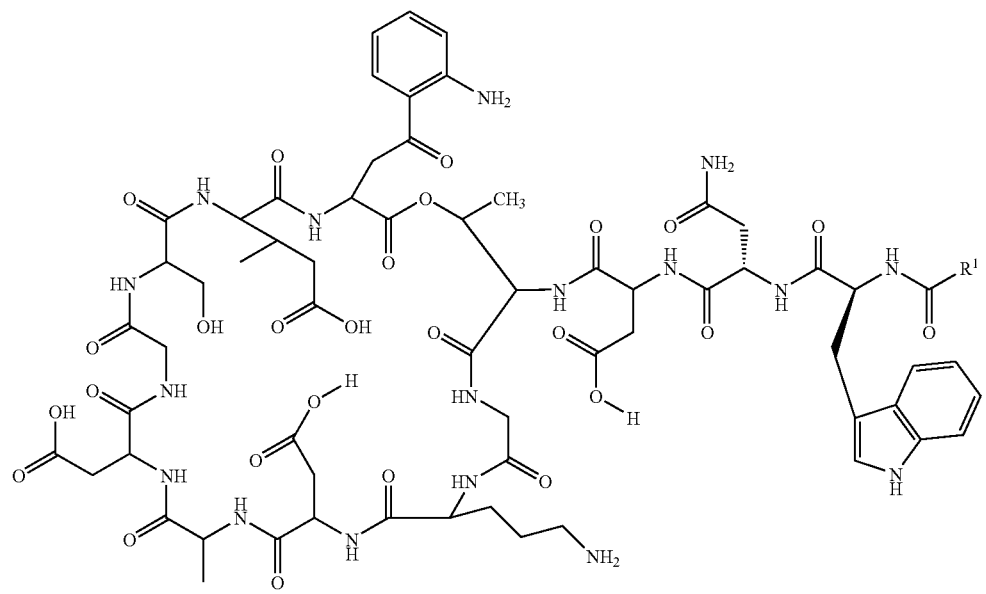
where R¹ is alkyl.
In another embodiment, the invention provides methods of preparing daptomycin and daptomycin stereoisomeric compounds. In particular, the invention provides a method for the preparation of a compound having the structure:
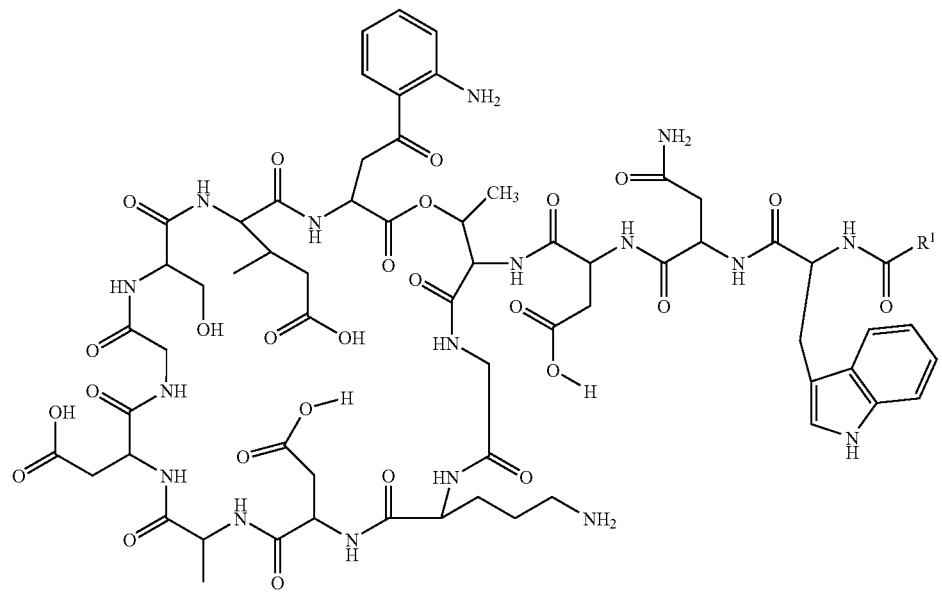

where R[1] is alkyl. This method includes the steps of: acylating a destryptophan compound having the structure:

where R[5] is an ornithine protecting group, R[6] is hydrido or an asparagine protecting group, and removing the ornithine

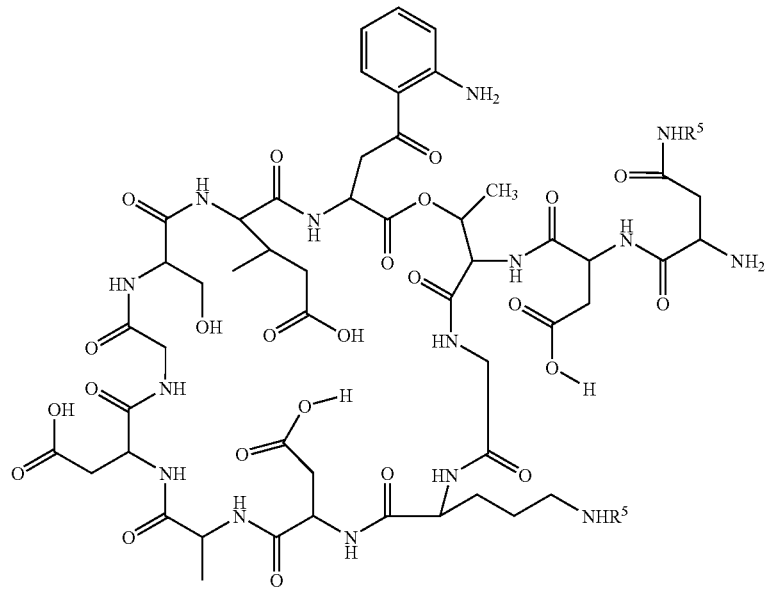

to obtain an ornithine amino protected compound having the structure:

protecting group and, when present, the asparagine protecting group, to obtain the compound having the structure:

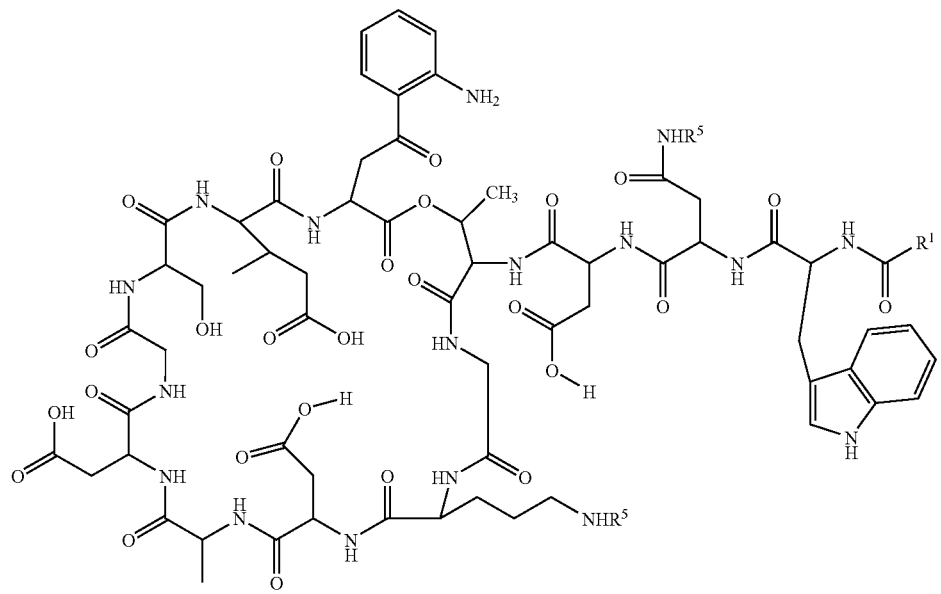

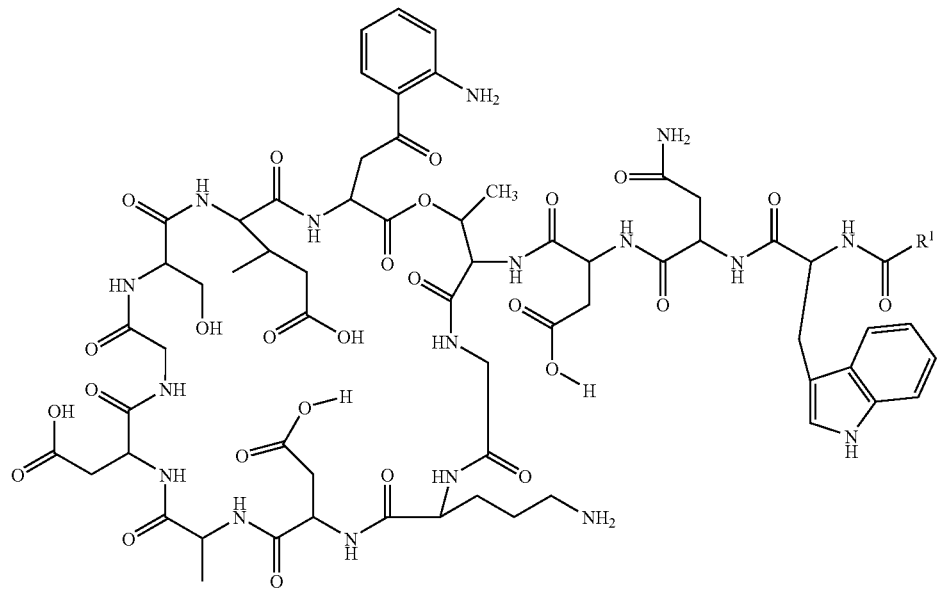

In another aspect of this embodiment, the method includes acylating the destryptophan compound with an acylating compound having the structure:

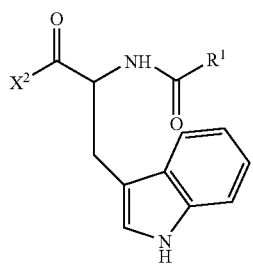

where $X^2$ is an activating group.

In a further aspect of this embodiment, the method includes acylating the destryptophan compound with an acylating compound having the structure:

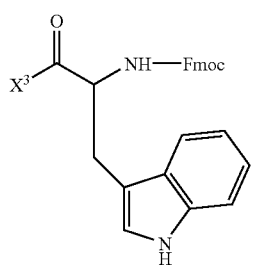

where $X^3$ is an activating group, to obtain a Fmoc-protected terminal tryptophanyl compound, removing the Fmoc group of the Fmoc-protected terminal tryptophanyl compound to obtain a terminal tryptophanyl compound, and then acylating the terminal tryptophanyl compound with an acylating compound having the structure:

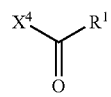

where $X^4$ is an activating group.

In another embodiment, the invention provides a method for the preparation of a compound having the structure:

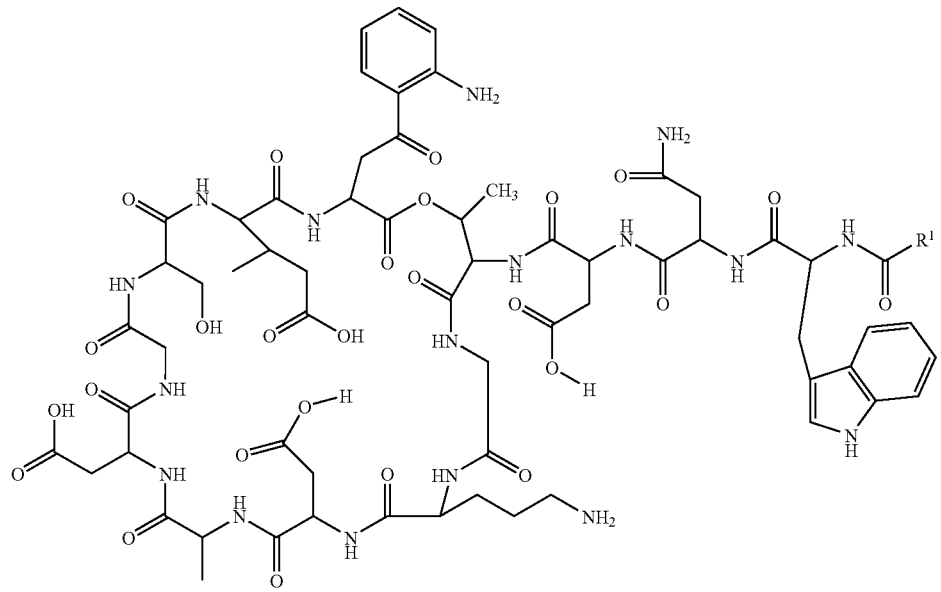
where R¹ is alkyl. This method includes the steps of:
acylating a desasparagine compound having the structure:
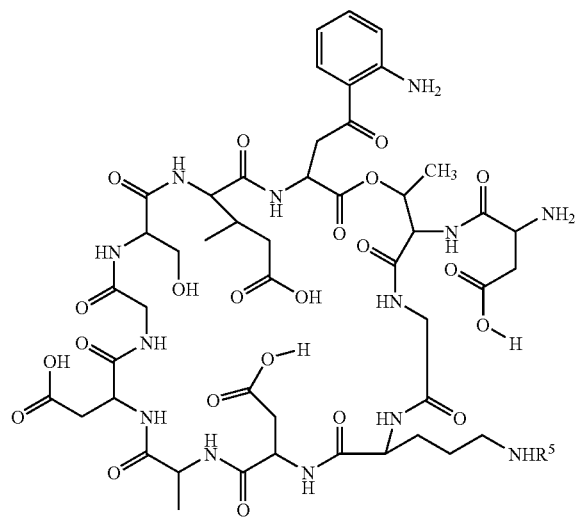
to obtain an ornithine amino protected compound having the structure:

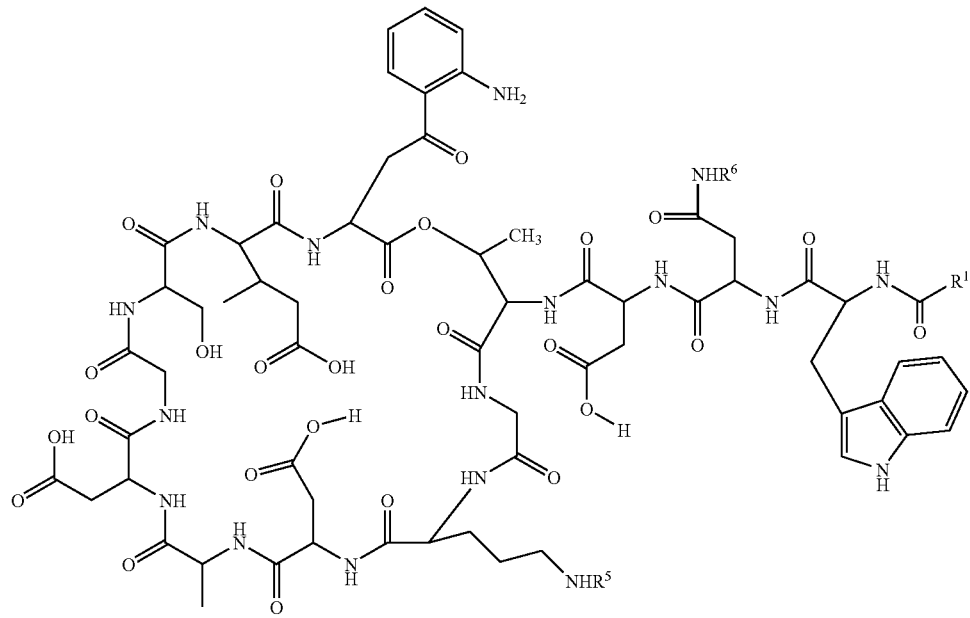

where R[5] is an ornithine protecting group, R[6] is hydrido or an asparagine protecting group, and removing the ornithine protecting group and, when present, the asparagine protecting group, to obtain the compound having the structure:

In another aspect of this embodiment, the method includes acylating the desasparagine compound with an acylating compound having the structure:

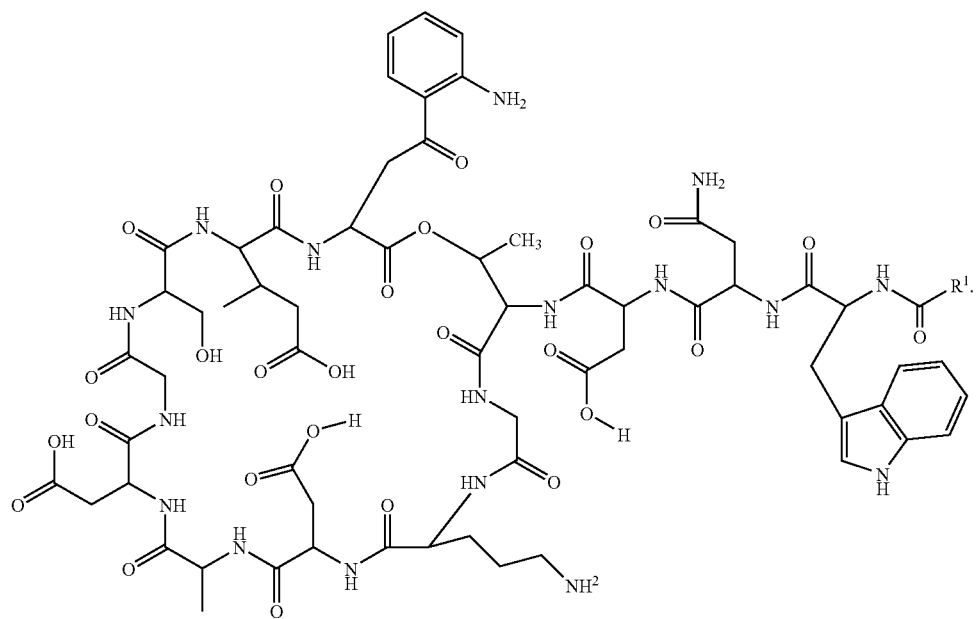

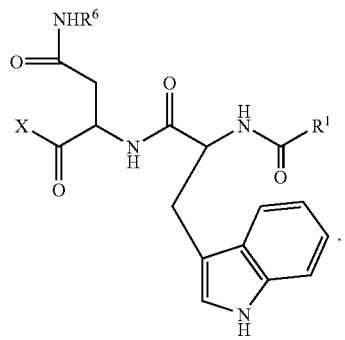

In yet another aspect of this embodiment, the method includes acylating the desasparagine compound with an acylating compound having the structure:

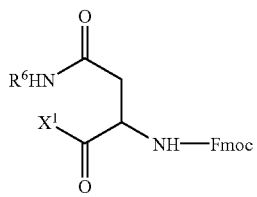

where $X^1$ is an activating group, to obtain an Fmoc-protected terminal asparaginyl compound, removing the Fmoc group of the Fmoc-protected terminal asparaginyl compound to obtain a terminal asparaginyl compound, and then acylating the terminal asparaginyl compound with an acylating compound having the structure:

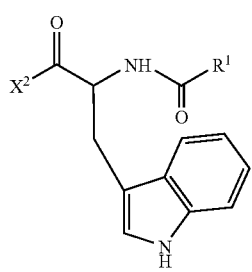

where $X^2$ is an activating group.

In still another aspect of this embodiment, the method includes acylating the desasparagine compound with an acylating compound having the structure:

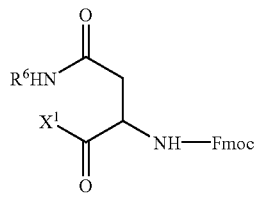

where $X^1$ is an activating group, to obtain a Fmoc-protected terminal asparaginyl compound, removing the Fmoc group of the Fmoc-protected terminal asparaginyl compound to obtain a terminal asparaginyl compound, and acylating the terminal asparaginyl compound with an acylating compound having the structure:

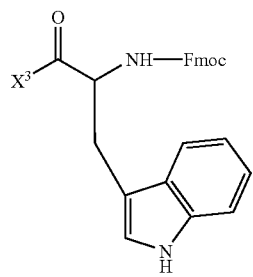

where $X^3$ is an activating group, to obtain a Fmoc-protected terminal tryptophanyl compound, removing the Fmoc group of the Fmoc-protected terminal tryptophanyl compound to obtain a terminal tryptophanyl compound, and acylating the terminal tryptophanyl compound with an acylating compound having the structure:

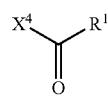

where $X^4$ is an activating group.

In another embodiment, the method of the invention includes the step of removing an asparagine residue from a destryptophan compound having the structure:

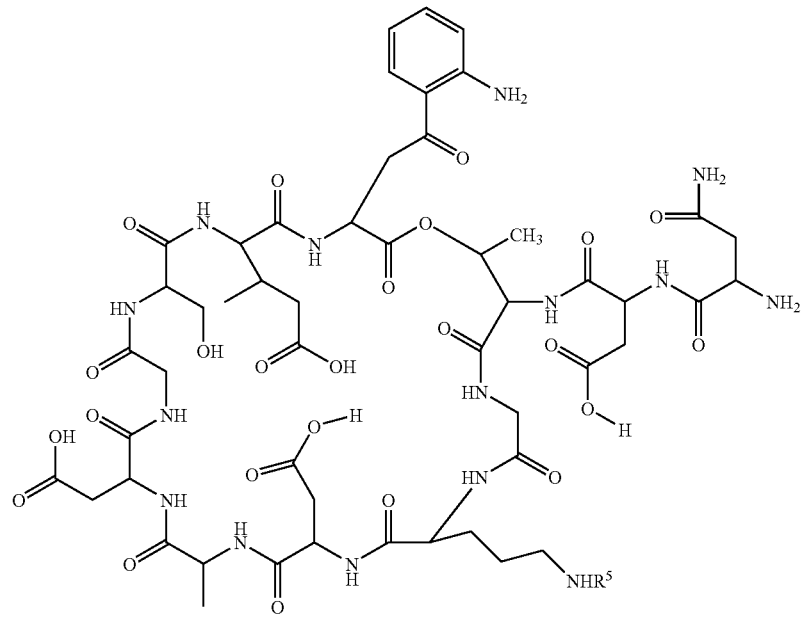
to obtain the desasparagine compound.
In a further embodiment, the method of the invention includes the step of removing a tryptophan residue from a deacylated compound having the structure:
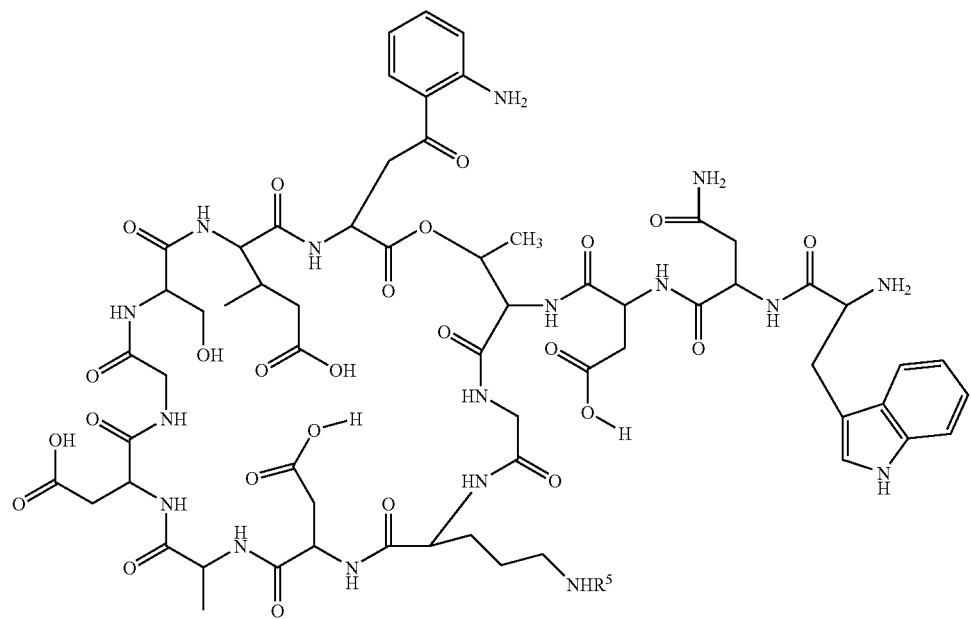

to obtain the destryptophan compound.
In other embodiments, the invention provides intermediates useful for the preparation of daptomycin and daptomycin stereoisomeric compounds. The invention provides the following intermediate compounds:
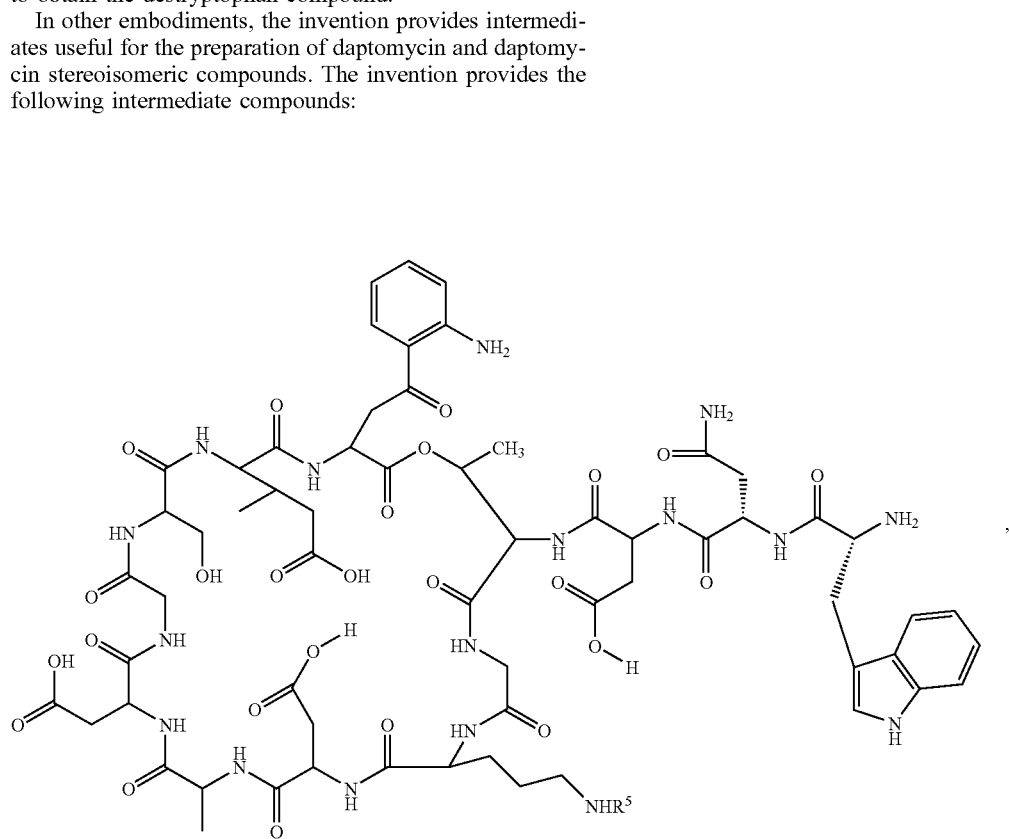
,
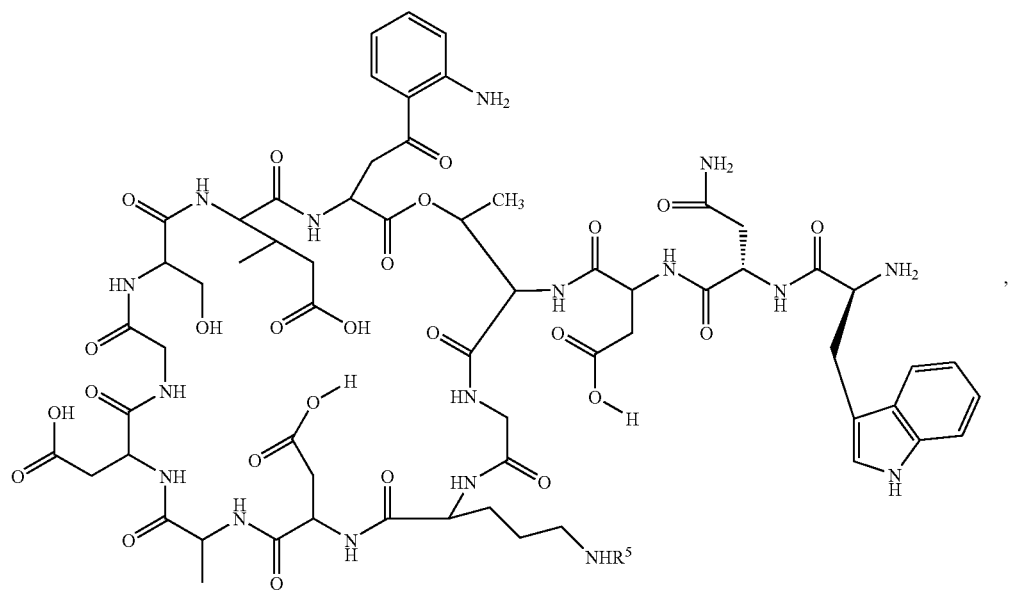
, -continued
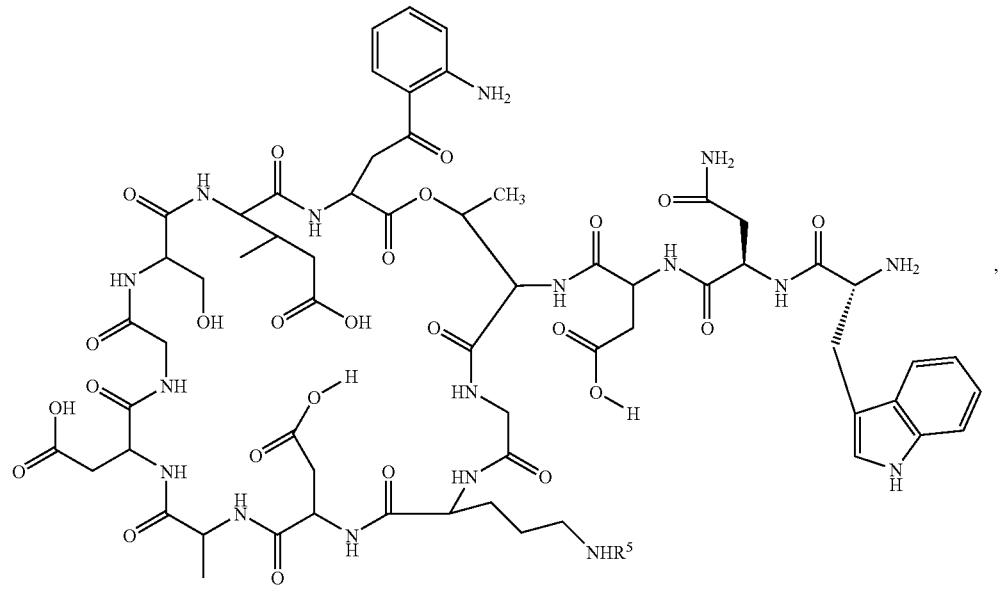
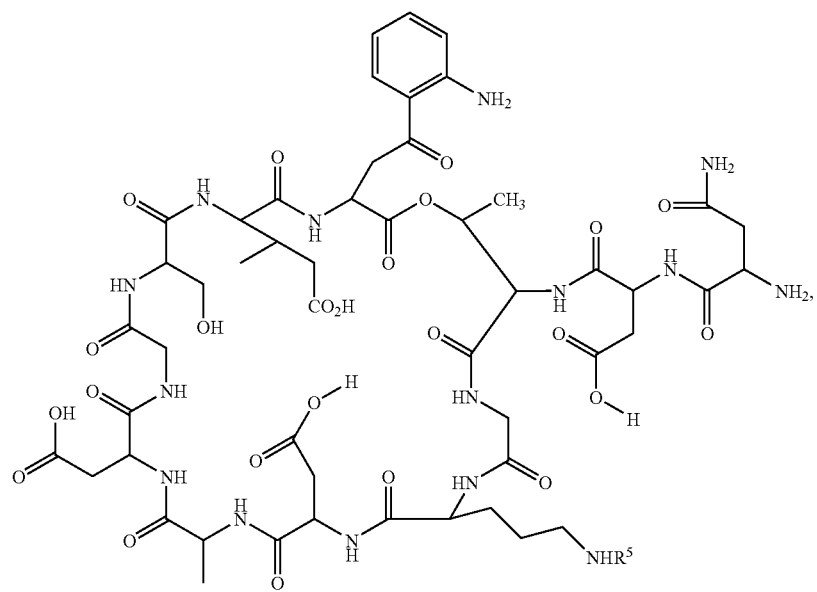

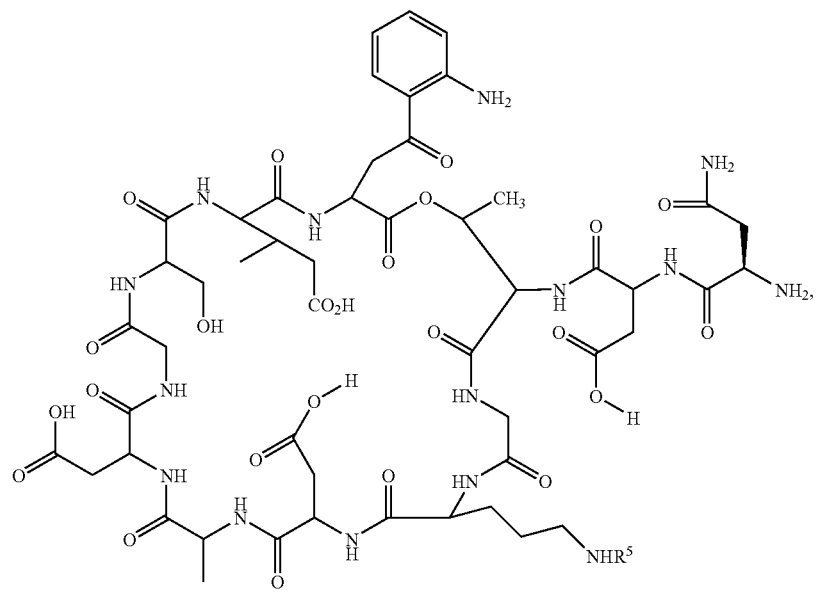
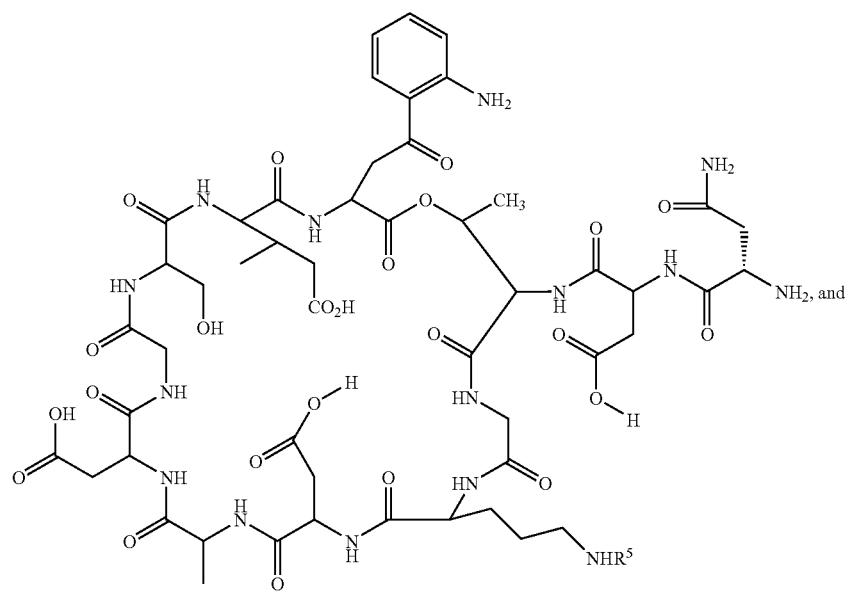

-continued

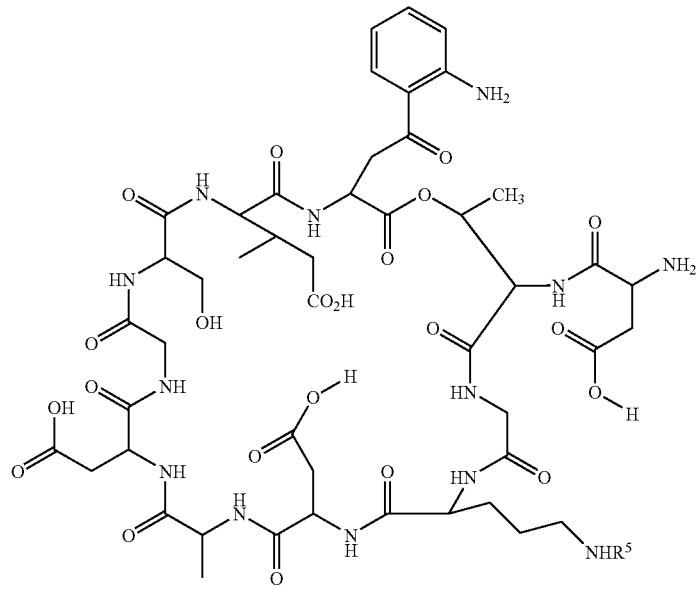

where R[5] is an ornithine protecting group.

In yet other embodiments, the invention features pharmaceutical compositions including one or more daptomycin stereoisomeric compounds. The invention also provides methods of using such compositions.

DETAILED DESCRIPTION OF THE INVENTION

Definitions

Molecular descriptive terms, when used in this application, have their common meaning unless otherwise specified.

The term "hydrido" denotes a single hydrogen atom (H).

The term "halo" is defined herein as a bromo, chloro, fluoro or iodo radical.

The term "alkyl" is defined herein as a linear or branched, saturated radical having one to about twenty carbon atoms unless otherwise specified. Preferred alkyl radicals are "higher alkyl" radicals having from about nine carbon atoms to about fifteen carbon atoms. Preferred alkyl groups are 7-methylnonyl, 9-methyldecyl, 9-methylundecyl, nonyl, and decyl.

The term "aryl" or "aryl ring" denotes aromatic radicals in a single or fused carbocyclic ring system, having from five to fourteen ring members. In a preferred embodiment, the ring system has from six to ten ring members. One or more hydrogen atoms may also be replaced by a halo or nitro substituent group.

The term "aryloxy" denotes oxy-containing radicals substituted with an aryl group. Examples include, without limitation, phenloxy, and pentafluorophenyloxy.

The term "amino acid side chain" denotes any side chain (R group) from a naturally-occurring or synthetic amino acid.

The term "amino protecting group" refers to any chemical compound that may be used to prevent an amino group on a molecule from undergoing a chemical reaction while chemical change occurs elsewhere in the molecule. Numerous amino protecting groups are known to those skilled in the art and examples can be found in "Protective Groups in Organic Synthesis" by Theodora W. Greene, John Wiley and Sons, New York, 1981, hereafter "Greene," incorporated herein by reference. Examples of amino protecting groups include pthalimido, trichloroacetyl, STA-base, bezyloxycarbonyl, t-butoxycarbonyl, t-amyloxycarbonyl, isobornyloxycarbonyl, adamantyloxycarbonyl, chlorobenzyloxycarbonyl, nitrobenzyloxycarbonyl or the like.

A "carbamate amino protecting group" which, when bound to an amino group, forms a carbamate, is a preferred amino protecting group. Preferred amino carbamate protecting groups include allyloxycarbonyl (alloc), carbobenzyloxy (CBZ), and tert-butoxycarbonyl protecting groups. Examples of carbamate amino protecting groups can be found in Greene and include but are not limited to, bezyloxycarbonyl, tert-butoxycarbonyl, t-amyloxycarbonyl, isobornyloxycarbonyl, adamantyloxycarbonyl, chlorobenzyloxycarbonyl, nitrobenzyloxycarbonyl or the like. Preferred carbamate amino protecting groups are allyloxycarbonyl (alloc), carbobenzyloxy (CBZ), and tert-butoxycarbonyl protecting groups (BOC).

The term "activating group" denotes a group that, when adjacent to a carbonyl group, activates the carbonyl group to attack by a nucleophilic amine, resulting in the loss of the activating group and the formation of an amide bond. Such activating groups are well known in the art and include aryloxy, acyloxy, imidazolyl,

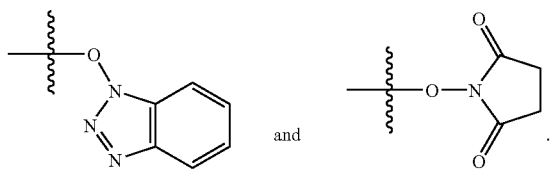
and

Preferred activating groups are aryloxy groups. A most preferred activating group is pentafluorophenloxy.

"Daptomycin stereoisomeric compound" is used herein to refer to any compound of Formula II, in which one or more chiral centers differs in absolute stereochemistry from daptomycin.

The group "Fmoc" is a 9-fluorenylmethoxycarbonyl group.

The group trityl is a triphenylmethyl group.

In one embodiment, the present invention provides a process for preparing compounds of Formula II:

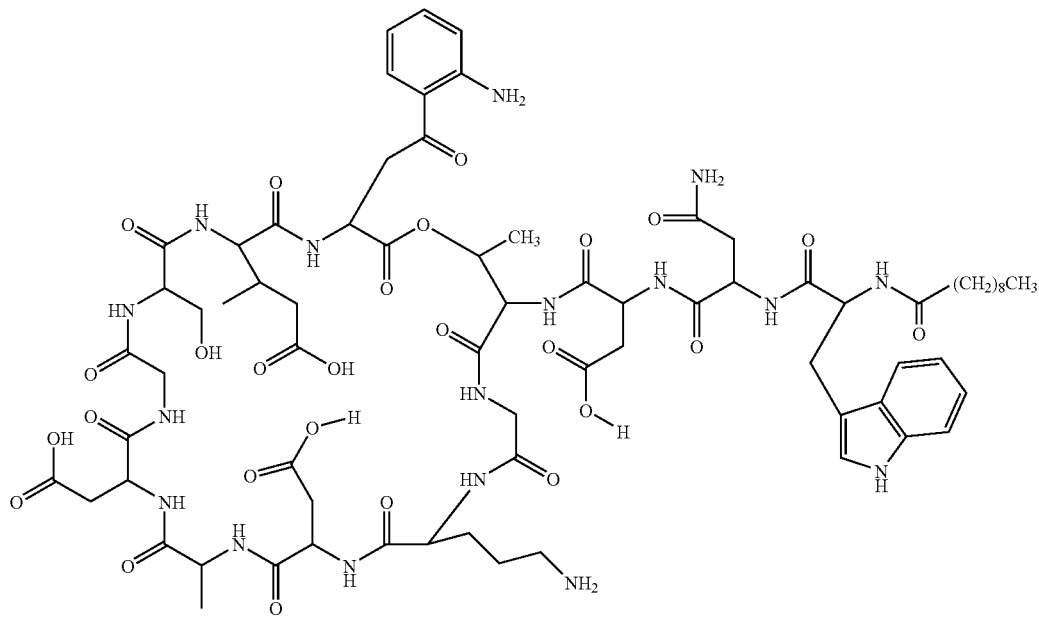

(II)

The process, in accordance with one aspect of the invention, includes the steps of:
(a) providing one or more A-21978C derivative of the Formula III

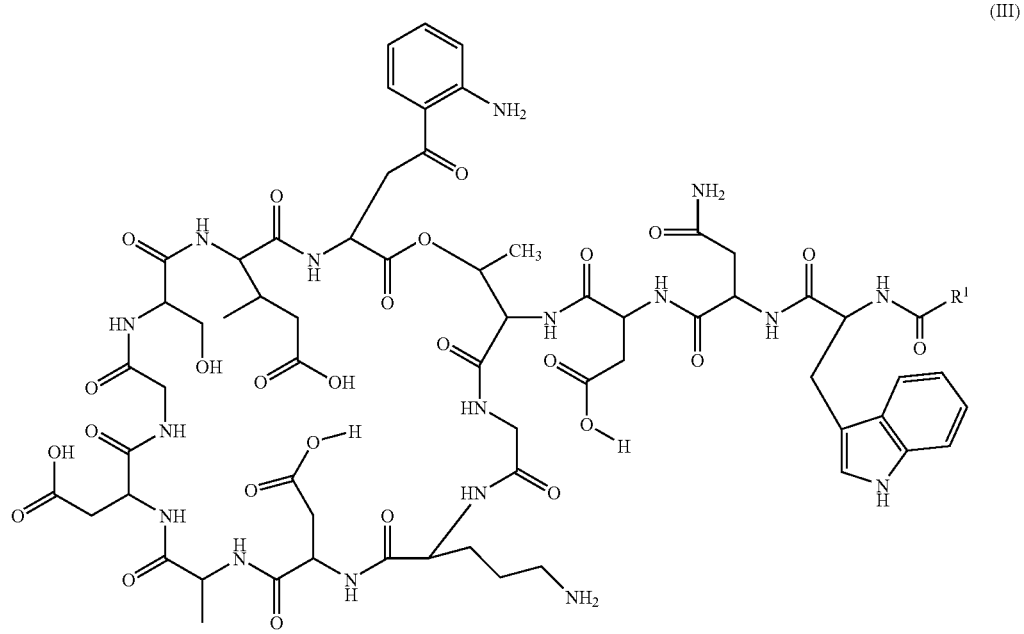

(III)

where R¹ is an alkyl group; or a salt thereof;
(b) treating the ornithine amine of a compound of Formula III with a carbamate amino protecting group to obtain an orninthine amino-protected A21978C compound;
(c) treating the ornithine amino-protected A21978C compound obtained in (b) with a deacylating agent to obtain a terminal amino A 21978C compound;
(d) removing the tryptophan amino acid residue of the terminal amino A 21978C compound obtained in (c) to obtain a compound;
(e) removing the asparagine amino acid residue of the destryptophan compound obtained in (d) to obtain a desasparagine compound;
(f) acylating the desasparagine compound of (e) with a compound of the Formula IV:

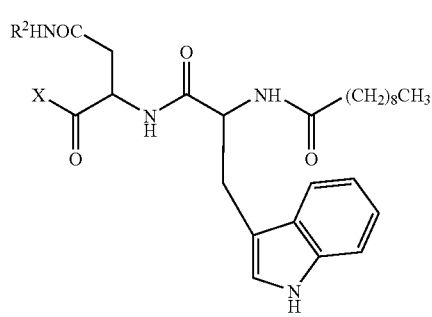

IV where X is an activating group and R² is hydrido to obtain an acylated compound; and removing the ornithine carbamate amino protecting group from the acylated compound to give the compound of Formula II; or (g) acylating the desasparagine compound of (e) with a compound of the Formula V:

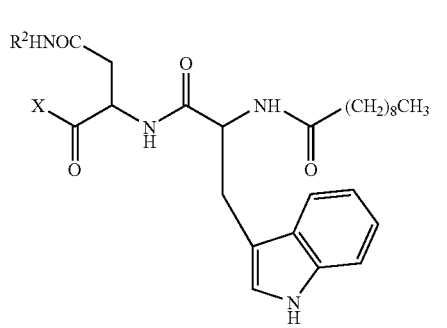

V where X is an activating group and R² is a trityl protecting group to obtain an acylated compound; and, removing the ornithine carbamate amino-protecting group and the trityl-protecting group to give the compound of Formula II.

In a second aspect, the process of the invention includes the steps of:
(a) providing one or more A-21978C derivative of the Formula III

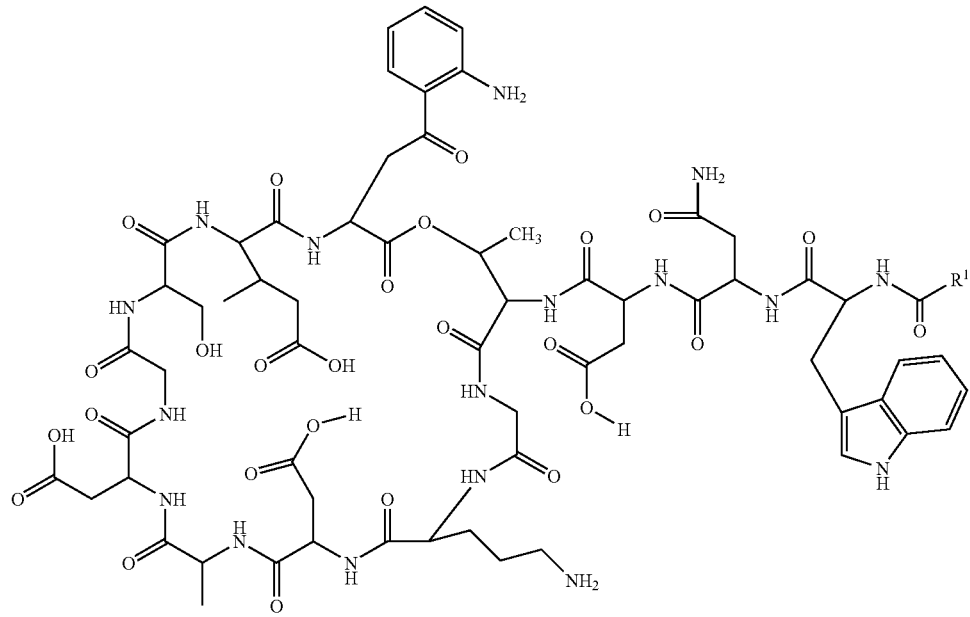

(III)

where R¹ is an alkyl group; or a salt thereof;
(b) treating the ornithine amino of a compound of Formula III with an amino protecting group to obtain an ornithine amino-protected A21978C compound;
(c) treating the orninthine amino-protected A21978C compound obtained in (b) with a deacylating agent to obtain a terminal amino A 21978C compound;
(d) removing the tryptophan amino acid residue of the terminal amino A 21978C compound obtained in (c) to obtain a destryptophan compound;
(e) removing the asparagine amino acid residue of the destryptophan compound obtained in (d) to obtain a desasparagine compound;
(f) acylating the desasparagine compound of (e) with a compound of the Formula VI:

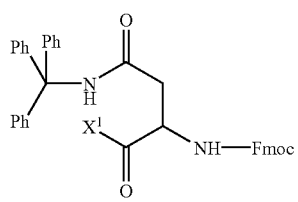

VI where X¹ is an activating group to give an Fmoc-protected terminal asparaginyl compound;
(g) removing the Fmoc group of the Fmoc-protected terminal asparaginyl compound of (f) selectively over the ornithine carbamate amino-protecting group to give a terminal asparaginyl compound;
(h) acylating the terminal asparaginyl compound of (g) with a compound of the Formula VII:

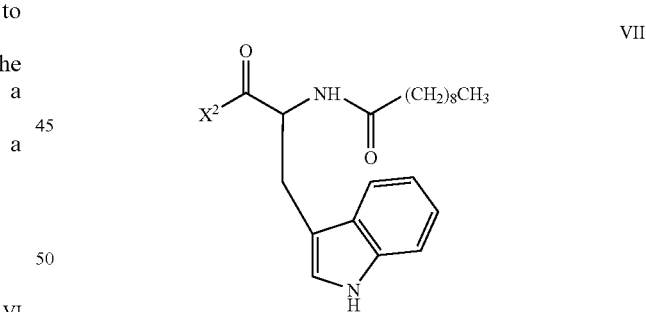

VII where X² is an activating group to give an acylated compound; and
(i) removing the ornithine carbamate- and trityl-amino protecting groups from the acylated compound to give the compound of Formula II.

The process, in a third aspect of the invention, includes the steps of:
(a) providing one or more A-21978C derivative of the Formula III

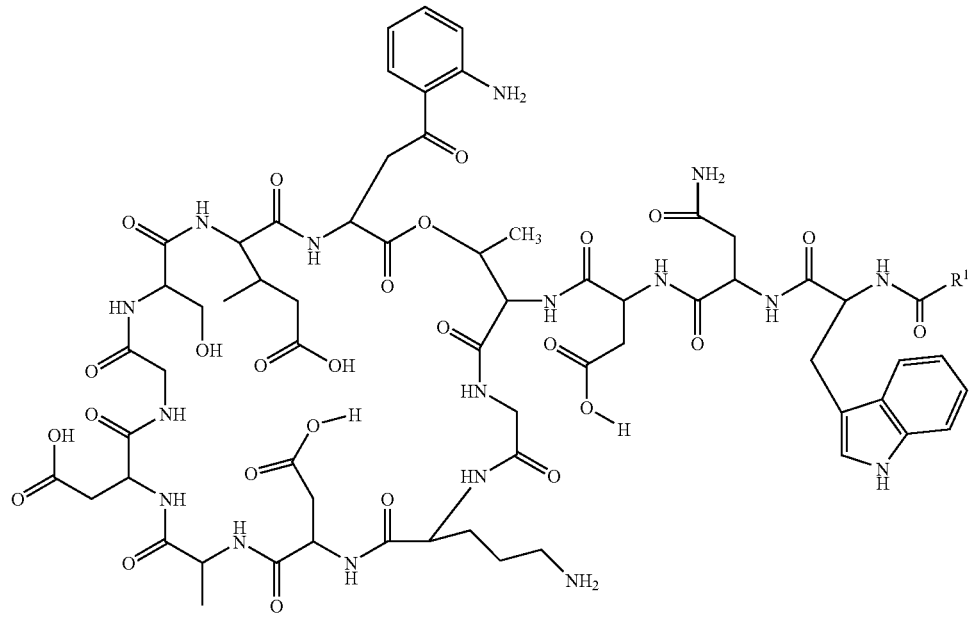

(III)

where R¹ is an alkyl group; or a salt thereof;

(b) treating the ornithine amino of a compound of Formula III with a carbamate amino-protecting group to obtain an orninthine amino-protected A21978C compound;

(c) treating the orninthine amino-protected A21978C compound obtained in (b) with a deacylating agent to obtain a terminal amino A 21978C compound;

(d) removing the tryptophan amino acid residue of the terminal amino A 21978C compound obtained in (c) to obtain a destryptophan compound;

(e) removing the asparagine amino acid residue of the destryptophan compound obtained in (d) to obtain a desasparagine compound;

(f) acylating the desasparagine compound of (e) with a compound of the Formula:

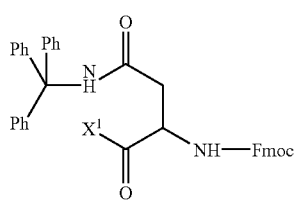

where X¹ is an activating group;

to give an Fmoc protected terminal asparaginyl compound;

(g) removing the Fmoc group of the Fmoc-protected terminal asparaginyl compound of (f) selectively over the ornithine carbamate-amino protecting group to give the terminal asparaginyl compound;

(h) acylating the terminal asparaginyl compound of (g) with a compound of the Formula

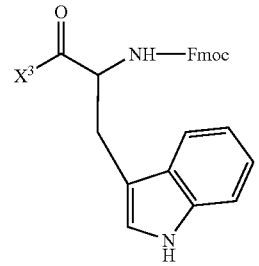

where X³ is an activating group;

to give the protected Fmoc terminal trytophanyl compound;

(i) removing the Fmoc group of the Fmoc-protected terminal tryptophanyl compound of (h) selectively over the ornithine carbamate amino protecting group to give the terminal trytophanyl compound;

(j) acylating the terminal tryptophanyl compound of (i) with a compound of the Formula

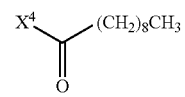

where X⁴ is an activating group;

to obtain an acylated compound; and (k) removing the ornithine carbamate amino and trityl protecting group from the acylated compound of (j) to give the compound of Formula II.

The salts of the compounds of the invention include acid addition salts and base addition salts. The term "pharmaceutically acceptable salts" embraces salts commonly used to form alkali metal salts and to form addition salts of free acids or free bases. The nature of the salt is not critical, provided that it is pharmaceutically-acceptable. Suitable pharmaceutically acceptable acid addition salts of the compounds of the invention may be prepared from an inorganic acid or an organic acid. Examples of such inorganic acids include, without limitation, hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts of compounds of the invention include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine. All of these salts may be prepared by conventional means from the corresponding compound of the invention by treating, for example, the compound of the invention with the appropriate acid or base.

The compounds of the invention can possess one or more asymmetric carbon atoms and are thus capable of existing in the form of optical isomers as well as in the form of racemic or non-racemic mixtures thereof. The compounds of the invention can be utilized in the present invention as a single isomer or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from the optically active salts. An alternative process for separation of optical isomers includes the use of a chiral chromatography column optimally chosen to maximize the separation of the enantiomers. Still another method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention can likewise be obtained by utilizing optically active starting materials. These isomers may be in the form of a free acid, a free base, an ester or a salt.

The invention also includes isolated compounds. An isolated compound refers to a compound which represents at least 10%, preferably at least 20%, more preferably at least 50% and most preferably at least 80% of the compound present in the mixture. In a preferred embodiment, the compound, a pharmaceutically acceptable salt thereof or a pharmaceutical composition comprising the compound exhibits a detectable (i.e. statistically significant) antimicrobial activity when tested in conventional biological assays such as those described herein.

Processes For Preparing Daptomycin Stereoisomeric Compounds

Prior to applicant's invention herein, only a single diastereomer of daptomycin had been reported (Formula I). Previous reports have concluded that the terminal tryptophan residue and the asparagine residue of daptomycin are both in the (L)-configuration. Applicants now have surprisingly found that the configuration of the asparagine residue of daptomycin had been previously misassigned and that the asparagine residue of daptomycin is actually in the (D)-configuration.

Based on applicant's discovery of the stereochemistry of the asparagine residue of daptomycin, the stereochemistry of the compound known as daptomycin can be accurately described by Formula IV:

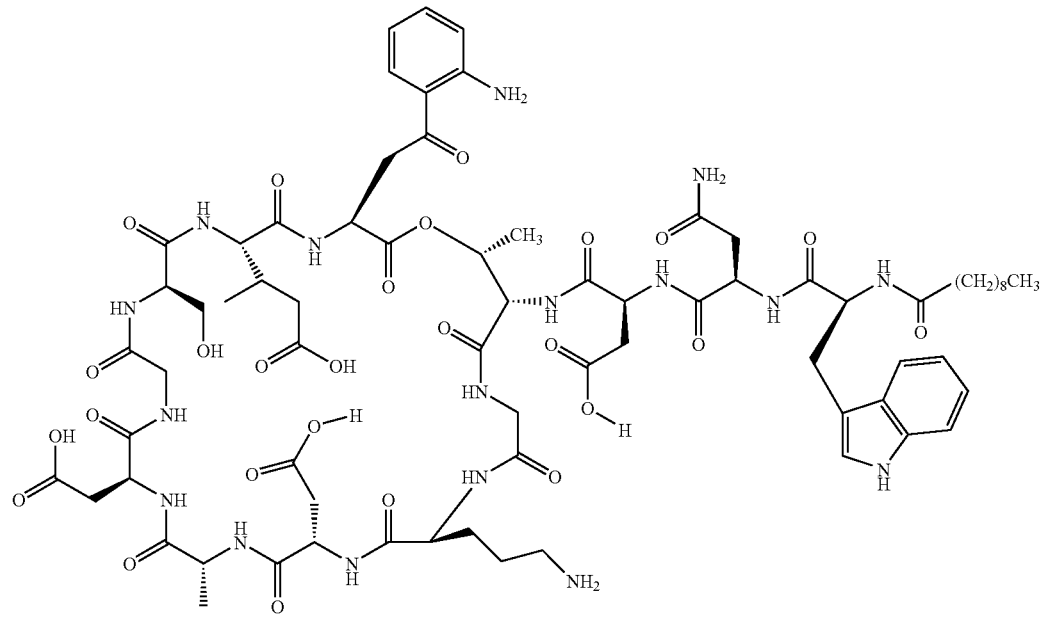

(IV)

All reported processes for the production of daptomycin have resulted in the formation of daptomycin as a single stereoisomer of Formula IV, rather than Formula I, as previously assigned. Similarly, there has been no reported preparation, isolation, or testing of the compound of Formula I, or, for that matter, stereoisomers of daptomycin other than the single isomer of Formula IV. Processes for the production of individual daptomycin stereoisomeric compounds are have not been previously reported.

The present invention provides an efficient method for preparing stereoisomers of lipopeptides, particularly daptomycin stereoisomeric compounds. The present invention allows for the efficient preparation of both racemic mixtures of compounds, as well as unique compounds of defined stereochemistry.

One process for the preparation of a compound of Formula II is illustrated in Scheme I.

Scheme I

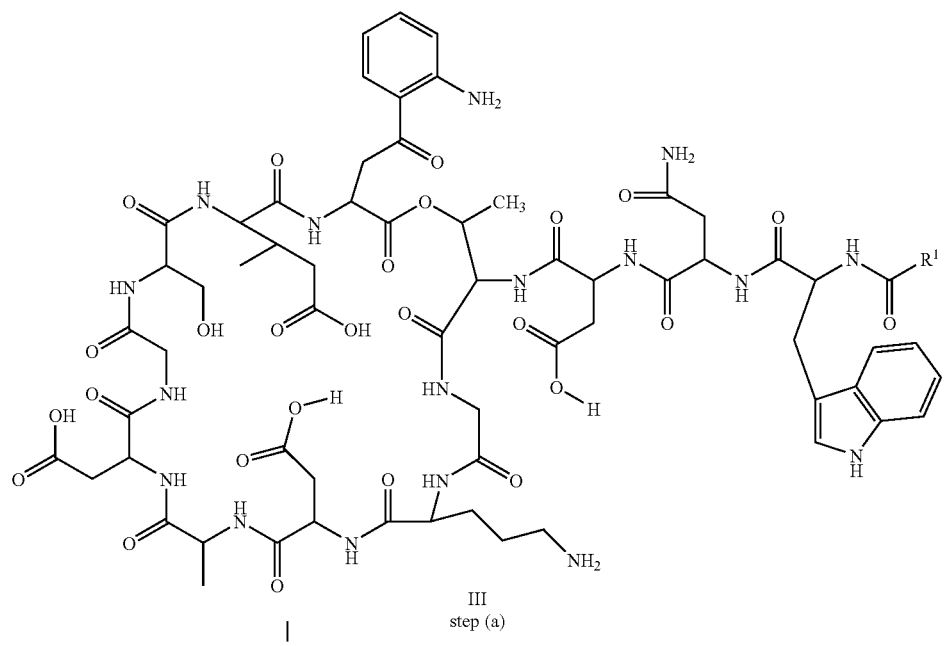

I

III
step (a)

Protection of the ornithine amine
step (b)
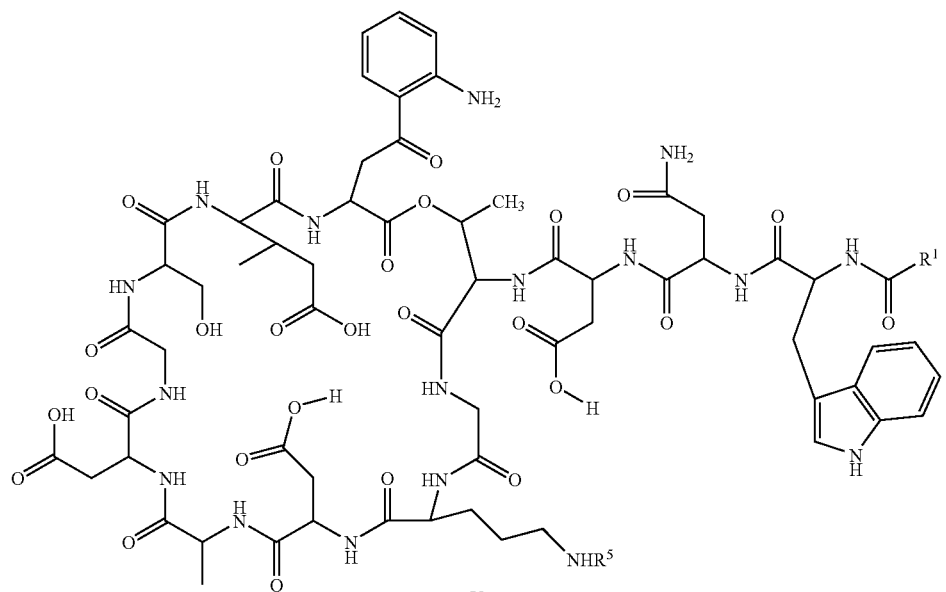
V
Deacylation
step (c)
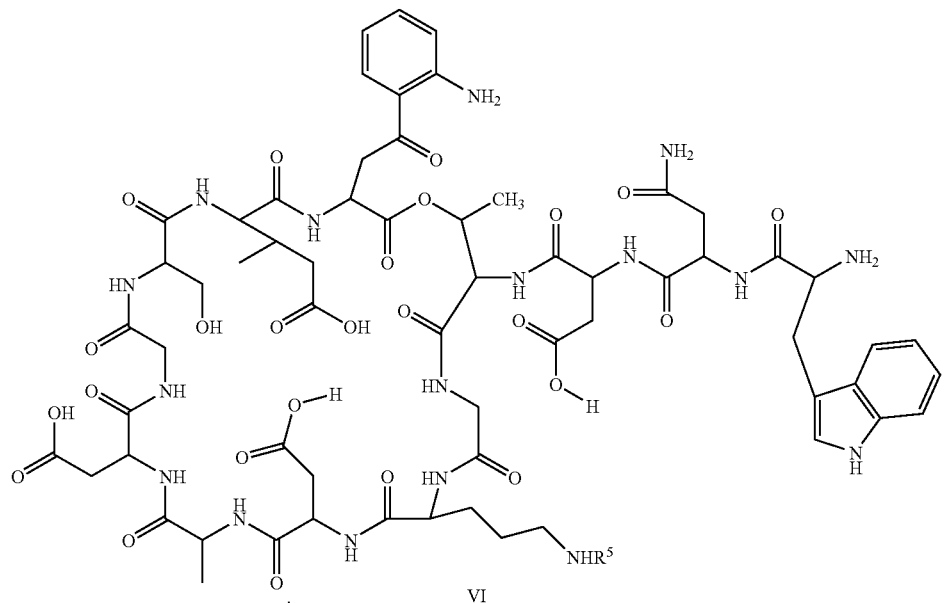
VI
Removal of the tryptophan amino acid residue
step (d)

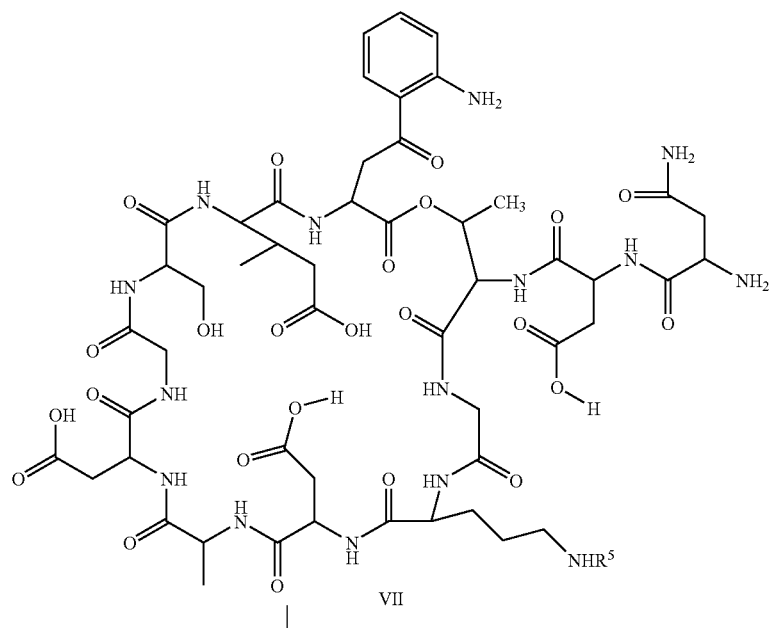
VII
Removal of the asparagine amino acid residue
step (e)
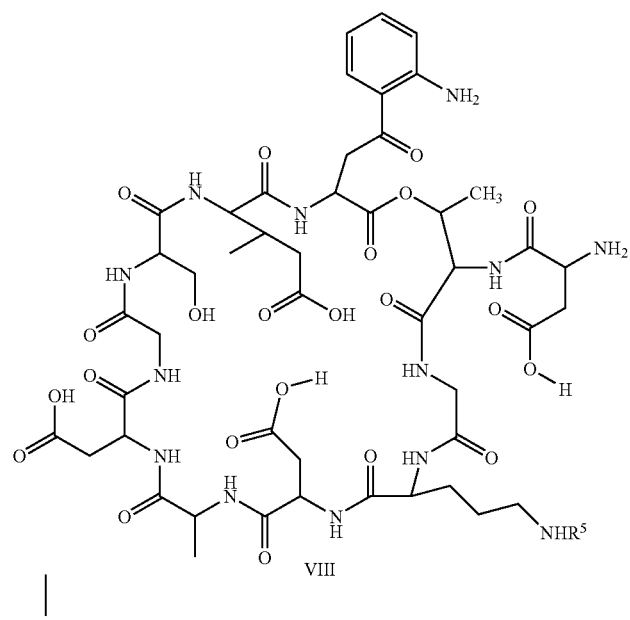
VIII

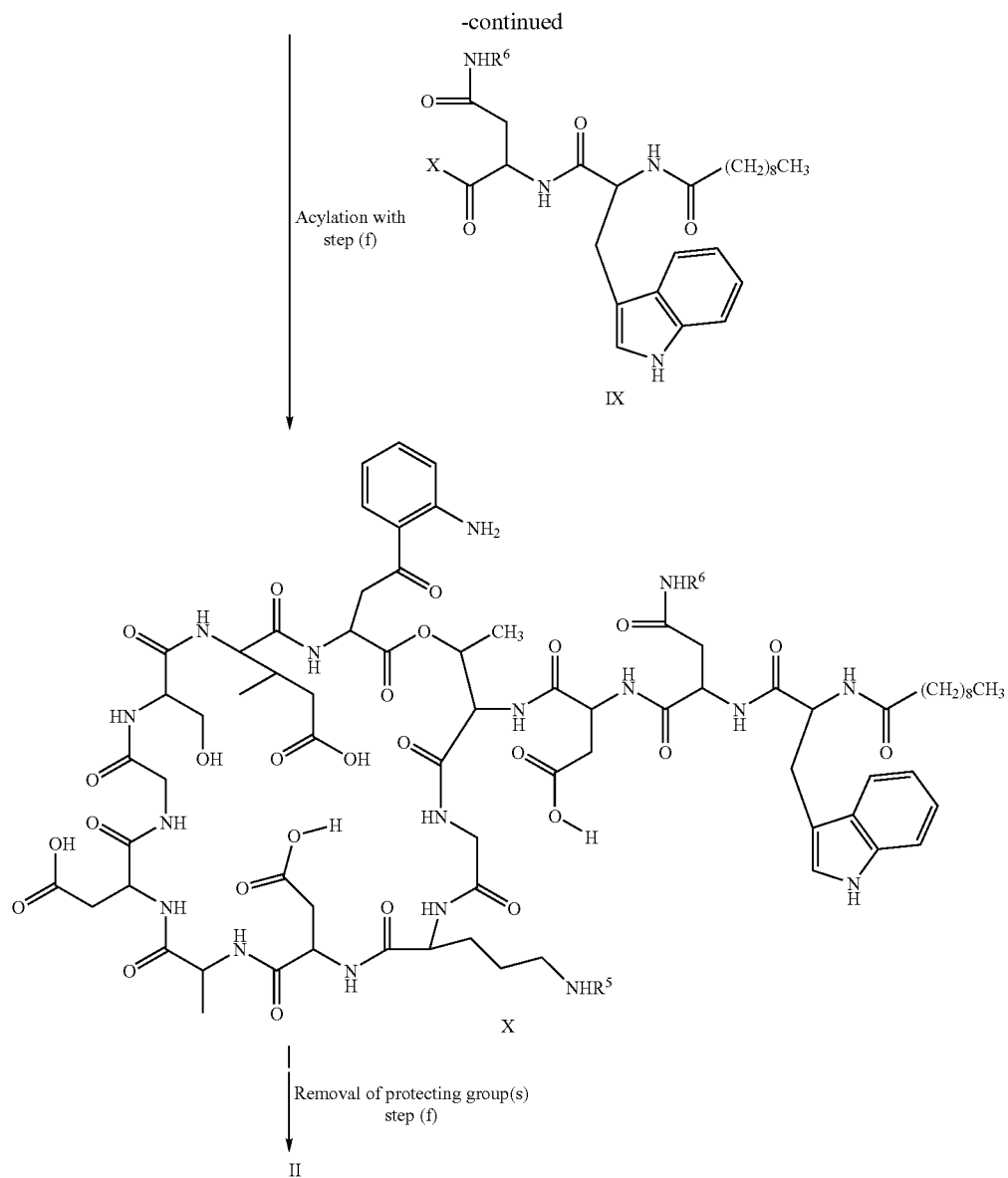

This process, in accordance with one aspect of the invention, comprises providing one or more A21978C derivatives of the Formula III (step(a)). Compounds of Formula III can be obtained by methods disclosed in United States Patents RE 32,333; RE 32,455; RE 32,311; U.S. Pat. Nos. 4,482,487; 4,537,717; 4,800,157, 4,874,843; 4,885,243 and 5,912, 226, each of which is incorporated herein by reference in its entirety. In preferred embodiments of the invention, $R^1$ is 7-methylnonyl, 9-methyldecyl, 9-methylundecyl, nonyl, decyl or mixtures thereof. In a more preferred embodiment $R^1$ is nonyl. In an even more preferred embodiment $R^1$ is n-nonyl. In the most preferred embodiment of the invention, compound III is daptomycin.

The ornithine amine of the A21978C derivative of Formula III is treated with an amino protecting group to give an ornithine amino protected A21978C compound of Formula V (step (b)), wherein $R^1$ is as previously defined and $R^5$ is an amino protecting group. Preferably, $R^5$ is a carbamate amino protecting group.

Methods of protecting the ornithine amine of daptomycin and related lipopeptides can be found in United States Patents RE 32,310; RE 32,311; U.S. Pat. Nos. 4,482,487; 4,524,135; and 4,537,717. Preferred carbamate amino protecting groups of the invention are benzyloxycarbonyl, tert-butoxycarbonyl and allyloxycarbonyl. The most preferred carbamate amino protecting group is allylyoxycarbonyl.

The ornithine amino protected A21978C compound of Formula V is then treated with a deacylating agent to form a terminal amino A21978C compound of Formula VI (step (c)). Enzymatic deacylating agents are suitable deacylating agents for use in the present invention. For example, an enzyme which is useful for deacylation of a compound of Formula V is produced by certain microorganisms of the family Actinoplanaceae. Some of these known species and varieties of this family include *Actinoplanes philippinensis, Actinoplanes armeniacus, Actinoplanes utahensis, Actinoplanes missouriensis, Spirillospora albida, Streptosporangium roseum, Streptosporangium vulgare, Streptosporangium roseum* var *hollandensi, Streptosporangium album, Streptosporangium viridialbum, Amorphosporangium auranticolor, Ampullariella regularis, Ampullariella campanulata, Ampullariella lobata, Ampullariella digitata, Pilimelia terevasa, Pimelia anulata, Planomonospora parontospora, Planomonospora venezuelensis, Planobispora longispora, Planobispora rosea, Dactylosporangium aurantiacum,* and *Dactylosporangium thailandende.* Any natural and artificial variant or mutant obtained from the Actinoplanacea and which produce the enzyme may be used in this invention.

Preferred sources of the deacylation enzyme are *Actinoplanes utahensi*: NRRL 12052; *Actinoplanes missouriensis* NRRL 12053; *Actinoplanes sp.*: NRRL8122, *Actinoplanes sp.*: NRRL 12065, *Streptosporsngium roseum* var *hollandensis*: NRRL 12064, *Actinoplanes utahenis* ATCC 14539 and *Actinoplanes missouriensis* ATCC 14538. The more preferred source of deacylation enzyme is the species *Actinoplanes utahensi*. The most preferred source of deacylation enzyme is one produced from recombinant *Streptomyces lividans*, which expresses the *Actinoplanes utahensis* deacylation enzyme as described in J. Ind. Microbiol. Biotechnol. 2000, 24(3) 173–180. This enzyme is also known as echinocandin B deacylase or ECB deacylase.

Suitable methods for enzymatic deacylation of compounds of Formula V can be found in U.S. Pat. Nos. 4,524,135; 4,537,717; 4,482,487; RE 32,310, and RE 32,311, each herein incorporated by reference in its entirety.

Removal of the tryptophan amino acid residue from the terminal amino A21978C compound of Formula VI, leads to the formation of the compound of Formula VII (step(d)). Methods for removal of the tryptophan amino acid residue are known to those skilled in the art. A preferred method for removal of the tryptophan amino acid residue is under standard Edman degradation conditions.

The Edman degradation is a well-established reaction known to those skilled in the art (see, for example, P. Edman, 1950, *Acta Chem. Scan.* 4: 283–93 and P. Edman, 1956, *Acta Chem Scan* 10: 761–768). In this reaction, the terminal NH$_2$ group of a peptide reacts with an isothiocynanate to form a thiourea derivative of the peptide. Upon treatment with acid or base, the thiourea peptide undergoes a cyclization reaction, giving a thiohydantoin and a shorter peptide (see Scheme II).

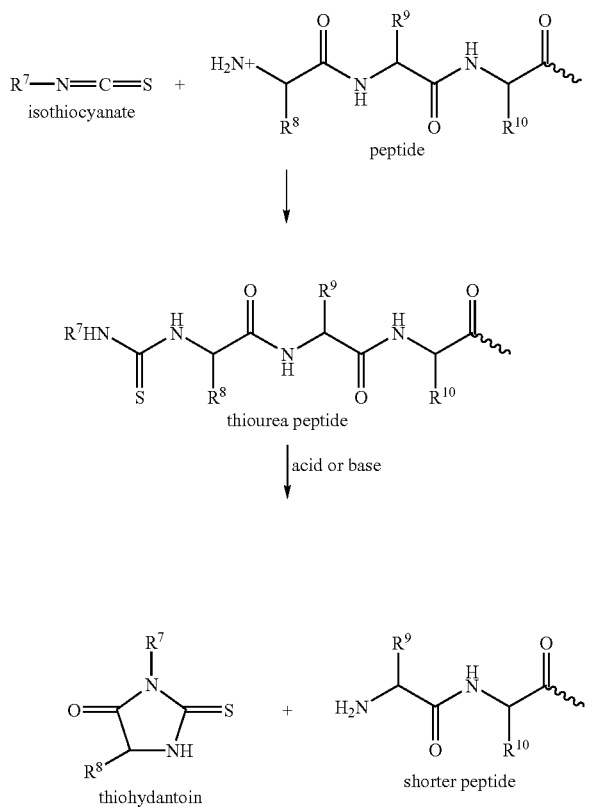

where each of R$^8$, R$^9$, and R$^{10}$ is, independently, an amino acid side chain.

The Edman degradation can be carried out under a variety of conditions. In the first step of the Edman degradation, the isothiocyanate reacts with the amine under neutral to mildly basic (pH<9.5) conditions in solvents such as tetrahydrofuran, N, N'-dimethylformamide, dichloromethane, dioxane or ethanol. A variety of isothiocyanates can be used (see K. K. Han et al. *Biochemie* 1977, 59: 557–576.

Subsequent cyclization and cleavage can be accomplished under a variety of conditions. Typically, anhydrous trifluoroacetic acid, heptafluorobutyric acid (see, for example, W. F. Brandt et al., 1976, *Z. Physiol. Chem.* 357: 1505–1508) or concentrated hydrochloric acid (see, for example, G. E. Tarr, 1977, *Methods in Enzymology* 47: 335–337) are used. Mild basic conditions such as triethylamine or N,N-dimethylallyamine/acetic acid (pH~9) can also be used (see G. C. Barrett et al., 1985, *Tetrahedron Letters* 26(36): 4375–4378). For a review of this reaction see K. K. Han, 1985, *Int. J. Biochem* 17(4): 429–445.

In a preferred embodiment, the thiourea peptide (the compound of Formula XI) formed upon reaction of the thioisocyanate with a compound of Formula VI is treated under acidic conditions to provide a compound of Formula VII. In a more preferred embodiment of the invention, a compound of Formula XI is treated with trifluoroacetic acid to give the compound of Formula VII (Scheme III).

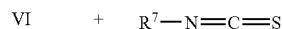

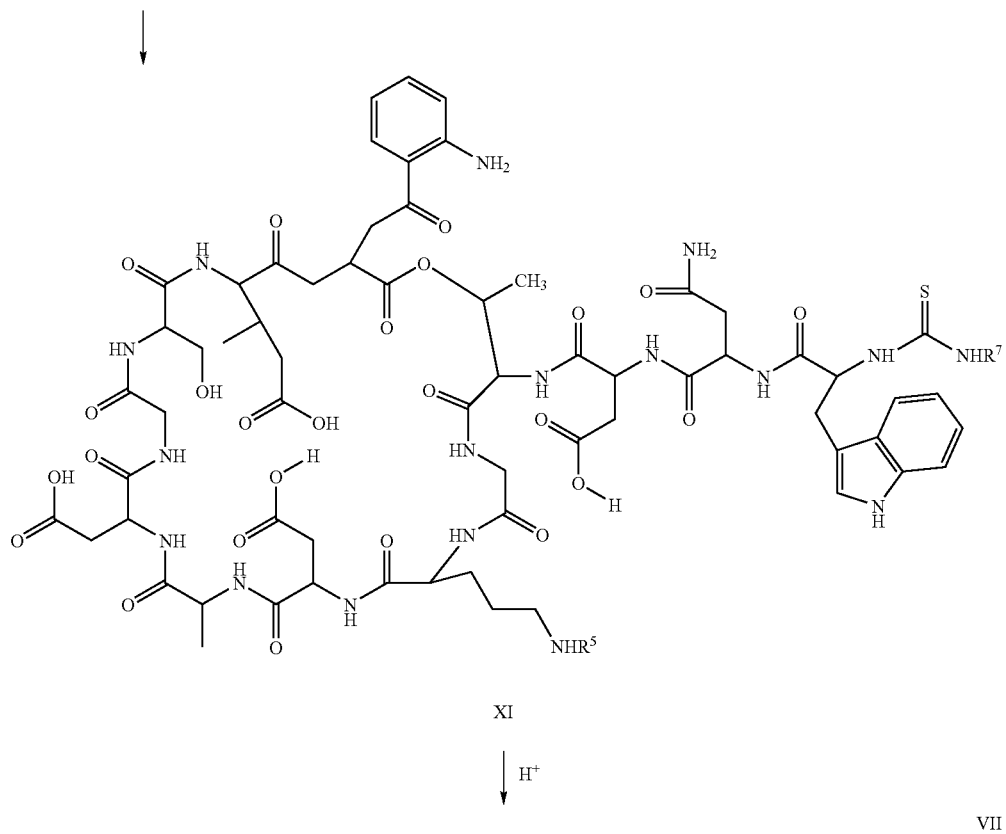

XI where $R^7$ is alkyl, aryl, 2-pyridyl or 3-pyridyl. In preferred embodiments, $R^7$ is phenyl, n-decyl, nonyl or octyl. In a more preferred embodiment, $R^7$ is n-decyl.

Removal of the asparagine amino acid residue from the compound of Formula VII, leads to the formation of the desasparagine compound of Formula VIII (step(e)). Methods for removal of the asparagine amino acid residue are known to those skilled in the art. Preferably, the asparagine amino acid residue is removed under Edman degradation conditions (vide supra).

In a preferred embodiment, the thiourea peptide (the compound of Formula XII) formed upon reaction of the thioisocyanate with a compound of Formula VII is treated under acidic conditions to provide desasparagine compound of Formula VIII. In a preferred embodiment of the invention, a compound of Formula XII is treated with trifluoroacetic acid to give the compound of Formula VIII (Scheme IV).

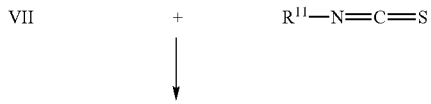

-continued

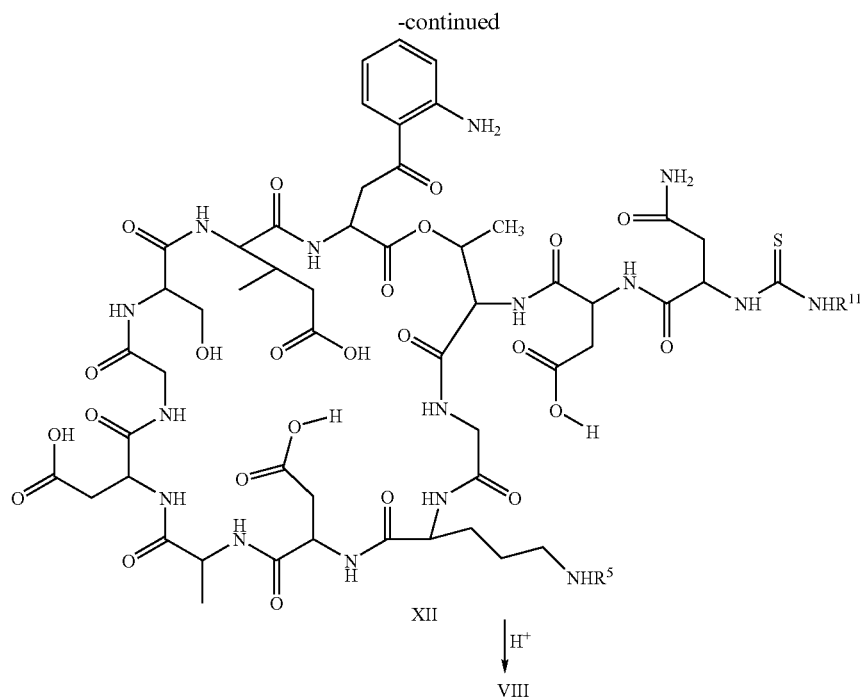

XII

↓ H⁺

VIII where $R^{11}$ is alkyl, aryl 2-pyridyl or 3-pyridyl. In preferred embodiments, $R^{11}$ is phenyl, n-decyl, nonyl or octyl. In a more preferred embodiment, $R^{11}$ is n-decyl.

Acylation of the desasparagine compound of Formula VIII with an activated compound of Formula IX results in the formation of acylated compound of Formula X (step(f)). Acylation reactions are well known to those skilled in the art. Acylation of complex molecules such as daptomycin and related lipopeptides can be found in U.S. Pat. Nos. 4,399,067; 4,482,487; and 4,537,717.

In a preferred embodiment, the substituent X on the acylating compound of Formula IX is an aryloxy group. In a more preferred embodiment, the substituent X is pentafluorophenoxy.

Compounds of Formula IX can be prepared from the corresponding peptide upon treatment with an activating agent such as an anhydride, a chloroformate, pentafluorophenol/dicyclohexylcarbodiimide, N',N'-carbonyldiimidazole, hydroxybenzotriazole or N-hydroxysuccinimide. These peptides can be prepared by any standard peptide procedure. For an overview of standard peptide formation procedures, see *Vogel's Textbook of Practical Organic Chemistry, 5th Ed.*, eds. B. S. Furniss, A. J. Hannaford; P. W. G. Smith; A. R. Tatchell (New York: John Wiley and Sons, Inc.), 1989, pp750–763 and *Introduction to Organic Chemistry, 2nd Ed.* by A. Streitwieser, Jr. and C. H. Heathcock (New York: MacMillan Publishing Co., Inc.), pp 954–962. Other methods for the preparation of peptides of the present invention involve synthesis on a solid support. Specific examples of such procedures are detailed in the examples herein.

Thus, using these procedures, a variety of stereoisomeric compounds of Formula IX are readily available. Compounds of Formula IX may be obtained and used in the acylation reaction as either a racemic mixture or as a single diastereomer. In a preferred embodiment of the invention the compound of Formula IX is enriched with one diastereomer. In a more preferred embodiment of the invention, the compound of Formula IX comprises greater than about 50% of one diastereomer. In an even more preferred embodiment of the invention, the compound of Formula IX comprises greater than about 75% of one diastereomer. In a still more preferred embodiment of the invention, the compound of Formula IX comprises greater than about 90% of one diastereomer. In another more preferred embodiment of the invention, the compound of Formula IX comprises greater than about 95% of one diastereomer. In a most preferred embodiment of the invention, the compound of Formula IX comprises greater than about 98% of one diastereomer. In a preferred embodiment of the invention, the asparagine residue of a compound of Formula IX is in the L or D configuration. In a preferred embodiment of the invention, the tryptophan residue of the compound of Formula IX is in the L or D-configuration. Preferred compounds of Formula IX are

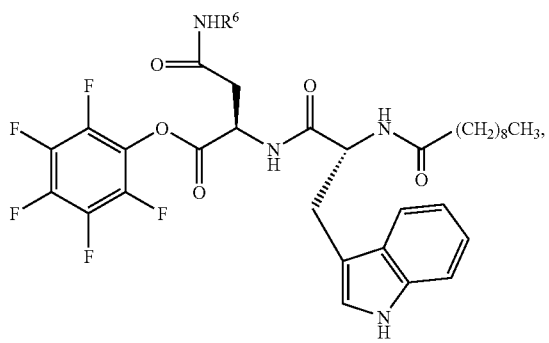

XIV

XV

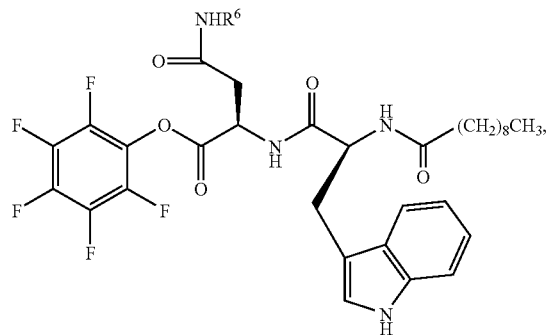

XVI

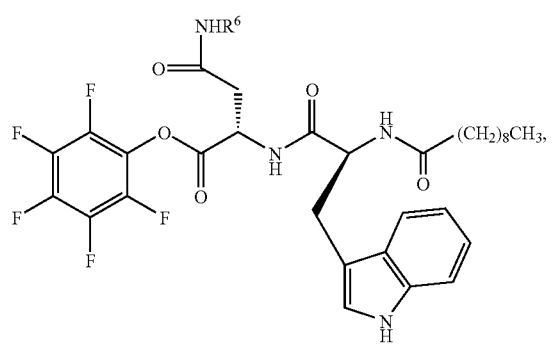

and

XVII

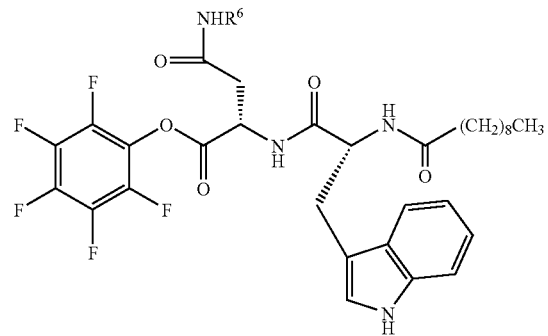

wherein $R^6$ is as previously defined.

Removal of the protecting group(s) from the acylated compound of Formula X results in the formation of the compound of Formula II. When $R^6$ is hydrido, only the ornithine protecting group needs to be removed. Removal of the ornithine amino protecting group can be accomplished according to procedures described in Greene. As one skilled in the art will recognize, the choice of amino protecting group employed in the first step of the process will dictate the reagents and procedures used in removing that amino protecting group.

When $R^6$ is an asparagine amino protecting group, both the asparagine amino protecting group and the ornithine amino protecting group are removed to obtain a compound of Formula II. Removal of these protecting groups can be accomplished in either a one step or a two step procedure, depending on the choice of amino protecting group employed in the first step of the process.

As one skilled in the art will recognize, a one step procedure may be used when the ornithine amino protecting group, $R^5$, is removed under conditions in which the asparagine amino protecting group is also removed, or vice versa. For example, because a trityl protecting group can be removed under acidic conditions, other amino protecting groups that are removed under acidic conditions are removed concurrently upon treatment with acid.

A two step procedure for removing asparagine amino protecting group and the ornithine amino protecting group, $R^6$ and $R^5$, respectively, may be used when the ornithine amino protecting group is removed under one set of conditions, while the asparagine amino protecting group is removed under a different set of conditions. In these cases, a step-wise approach may be employed, such that one amino protecting group is removed in a first step, and the other amino protecting group is removed in a second step. For example, a trityl group may be removed in the first step to give a compound of Formula XVIII, then a carbamate amino protecting group can be removed in the second step to give a compound of Formula II. Alternatively the carbamate amino protecting group can be removed in the first step to give a compound of Formula XIX, and then the trityl protecting group can be removed in the second step to give the compound of Formula II (Scheme V).

Scheme V
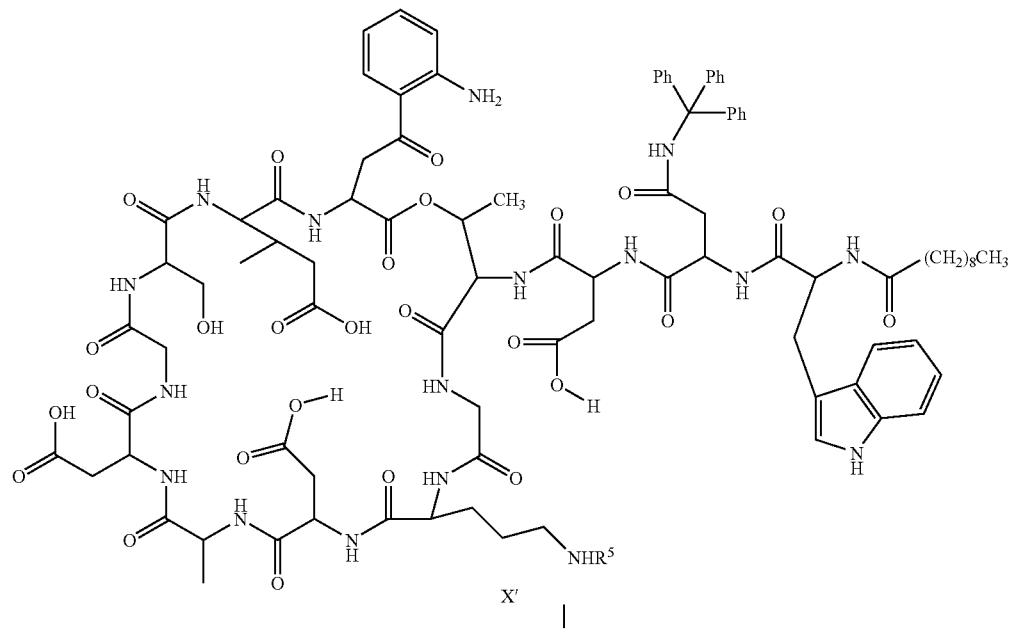
↓ removal of trityl protecting group
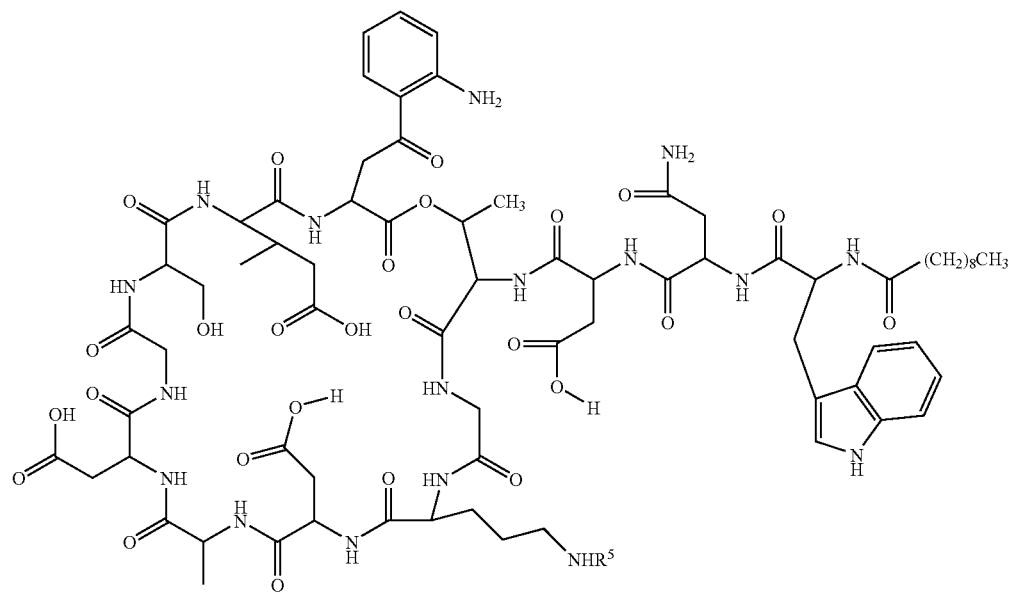
↓ removal of carbamate amino protecting group
II -continued
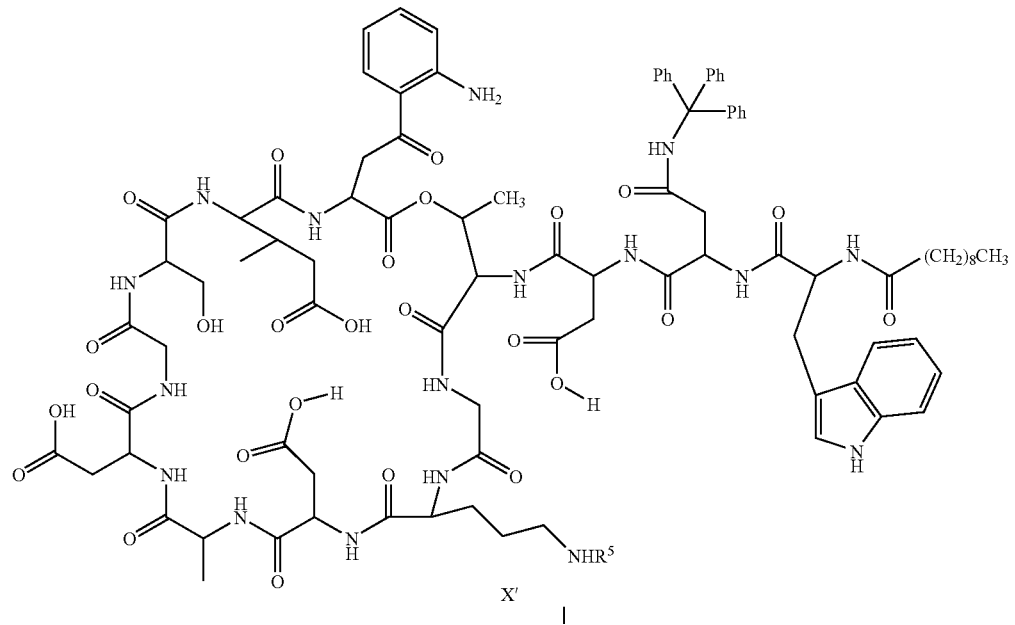
X'
↓ removal of carbamate amino protecting group
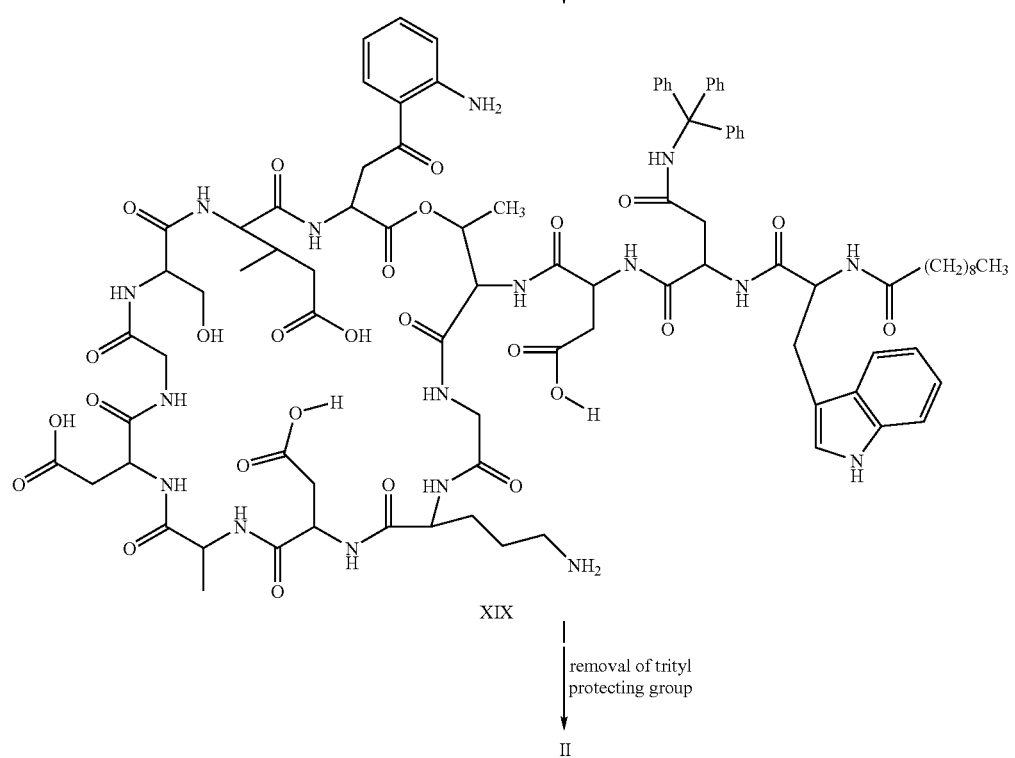
XIX
↓ removal of trityl protecting group
II
The process of the invention, in a second aspect, is outlined in Scheme VI. In this process, the transformation of a compound of Formula VIII, from step (e) above, to a compound of Formula X, may be conducted in three steps.

Scheme VI
VIII
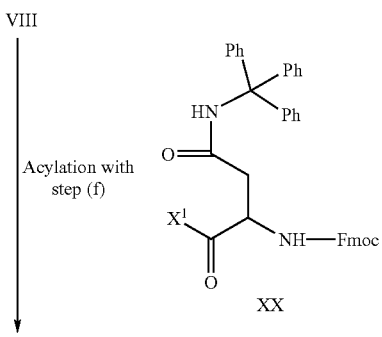
↓ Acylation with step (f)
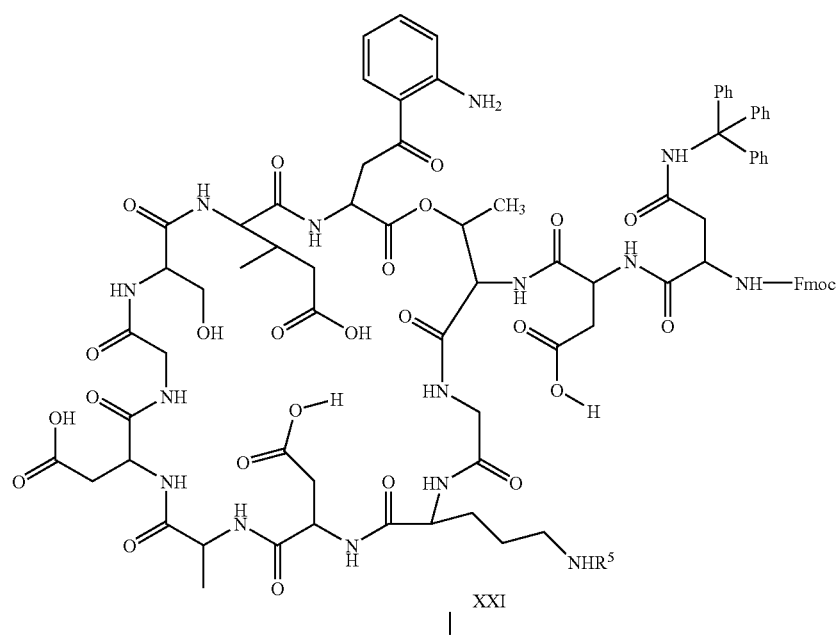
XXI
↓ removal of Fmoc group step (g)

-continued

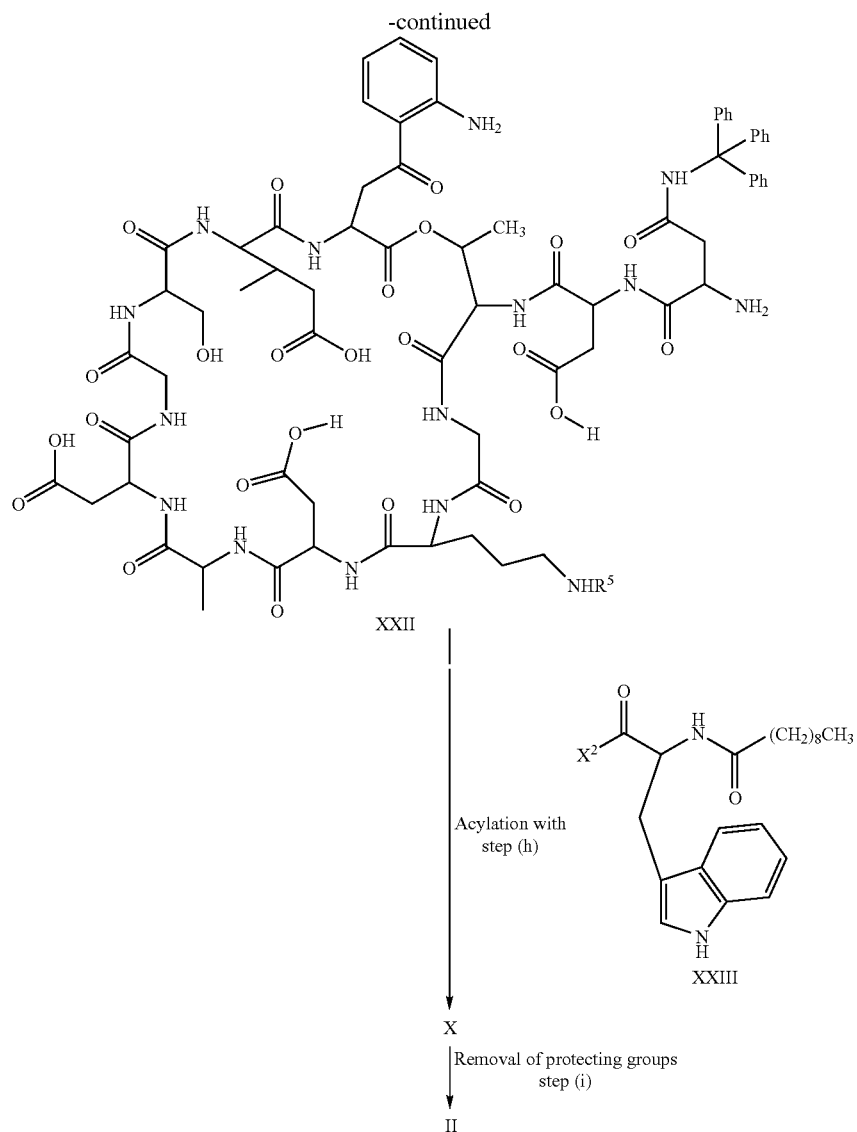

where $R^5$ is as described previously and each of $X^1$ and $X^2$ is, independently, an activating group.

The desasparagine compound of Formula VIII is acylated with a compound of Formula XX to give the Fmoc protected terminal asparaginyl compound of Formula XXI (step(f)). The acylation may be performed as previously described.

For example, the compound of Formula XX is readily available via activation of commercially available trityl protected N-Fmoc-asparagine using methods as discussed previously. In a preferred embodiment of the invention, $X^1$ is an aryloxy group. In a more preferred embodiment of the invention, $X^1$ is pentafluorophenyloxy.

Compounds of the Formula XX may be obtained and used in the acylation reaction as either a racemic mixture or as a single enantiomer. In a preferred embodiment of the invention, the compound of Formula XX is enriched with one enantiomer. In a more preferred embodiment of the invention, the compound of Formula XX comprises greater than about 50% of one enantiomer. In an even more preferred embodiment of the invention, the compound of Formula XX comprises greater than about 75% of one enantiomer. In a still more preferred embodiment of the invention, the compound of Formula XX comprises greater than about 90% of one enantiomer. In another more preferred embodiment of the invention, the compound of Formula XX comprises greater than about 95% of one enantiomer. In a most preferred embodiment of the invention, the compound of Formula XX comprises greater than about 98% of one enantiomer.

The Fmoc protecting group of the Fmoc protected terminal asparaginyl compound of Formula XXI is removed to afford the terminal asparaginyl compound of Formula XXII according to procedures described in Greene (step(g)).

The terminal asparaginyl compound of Formula XXII is acylated with a compound of Formula XXIII to give the acylated compound of Formula X (step(h)). The acylation reaction can be performed as described previously. The compound of the Formula XXIII is readily available via (a) acylation of tryptophan followed by activation as described previously or (b) acylation of a tryptophan ester (e.g.

methyl-, ethyl-, t-butyl-, allyl-, or benzyl ester), followed by hydrolysis then activation as described previously. In a preferred embodiment of the invention, $X^2$ is an aryloxy group. In a more preferred embodiment of the invention, $X^2$ is pentafluorophenyloxy. Compounds of the Formula XXIII may be obtained and used in the acylation reaction as either a racemic mixture or as a single enantiomer. In a preferred embodiment of the invention, the compound of Formula XXIII is enriched with one enantiomer. In a more preferred embodiment of the invention, the compound of Formula XXIII comprises greater than about 50% of one enantiomer. In an even more preferred embodiment of the invention, the compound of Formula XXIII comprises greater than about 75% of one enantiomer. In a still more preferred embodiment of the invention, the compound of Formula XXIII comprises greater than about 90% of one enantiomer. In an even still more preferred embodiment of the invention, the compound of Formula XXIII comprises greater than about 95% of one enantiomer. In the most preferred embodiment of the invention, the compound of Formula XXIII comprises greater than about 98% of one enantiomer.

The compound of the Formula X is then converted to the compound of Formula II as previously described (step(i)).

The process of the invention, in a third aspect, it outlined in Scheme VII. In this process, the transformation of a compound of Formula VIII to a compound of Formula X may be conducted in five steps.

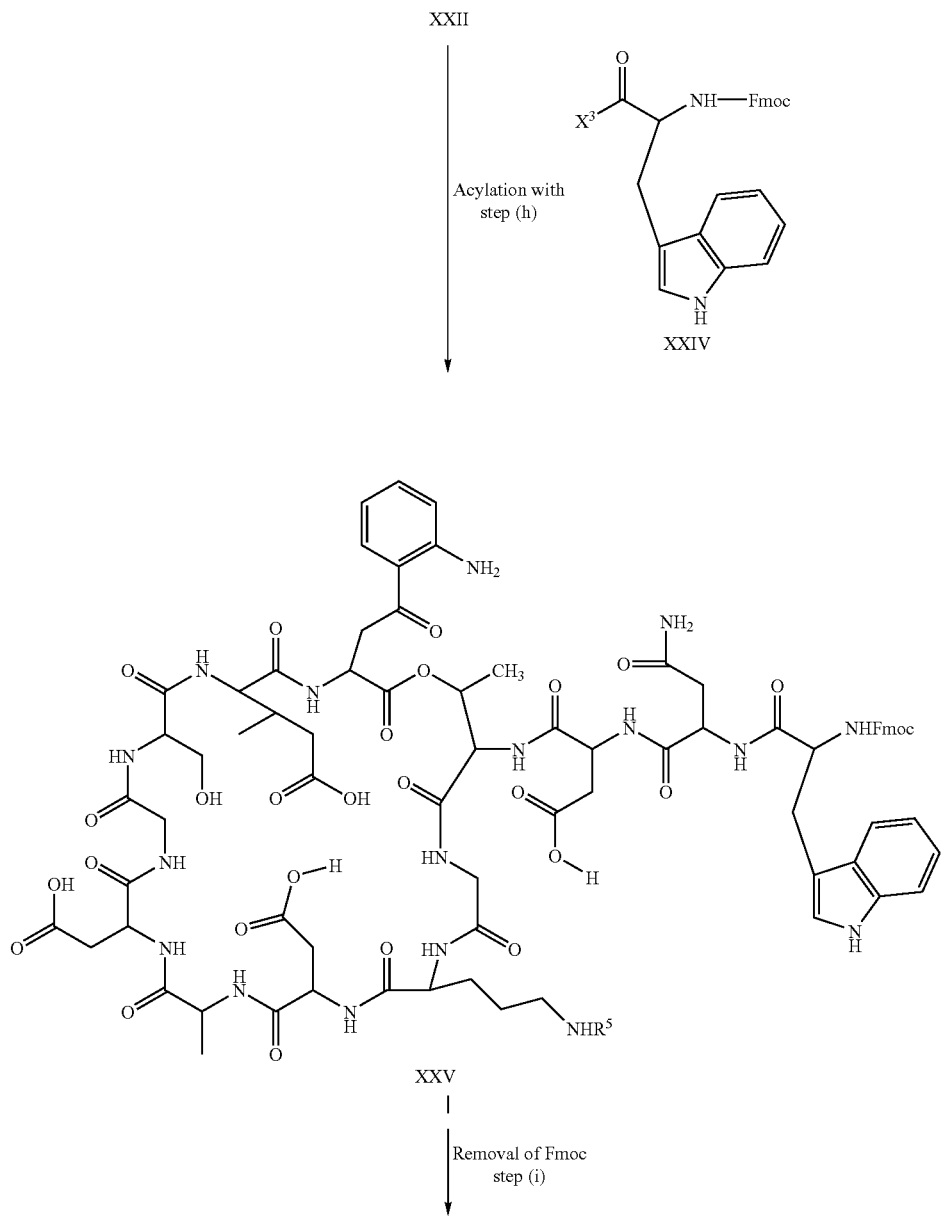

-continued

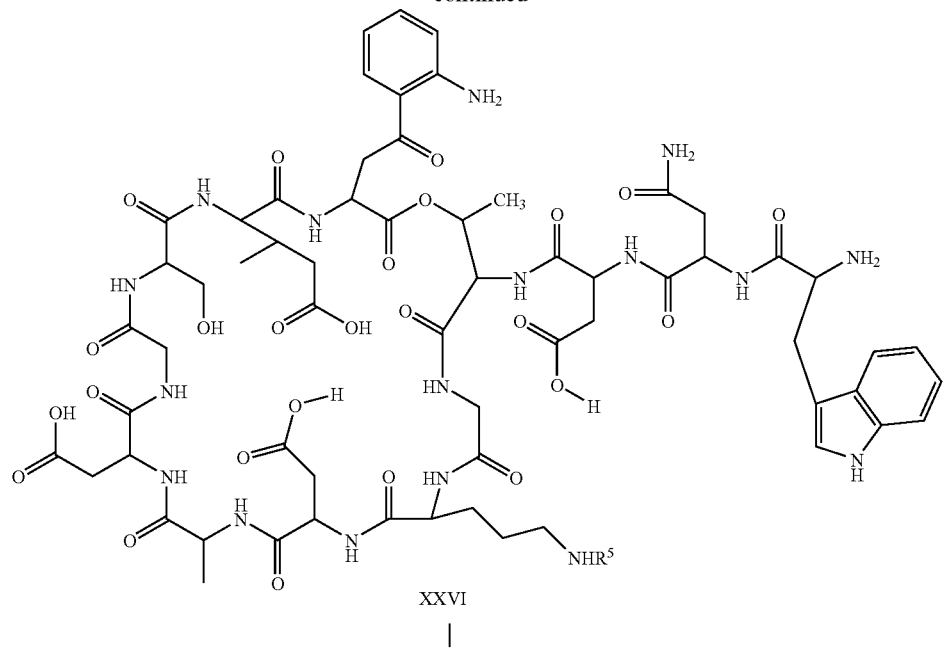

XXVI

↓ Acylation with step (j) | $X^4 \overset{O}{\underset{}{\|}} (CH_2)_8 CH_3$

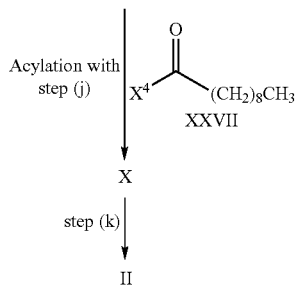

XXVII

↓

X

↓ step (k)

II where $R^5$ is as previously defined and each of $X^3$ and $X^4$ is, independently, an activating group.

In this process, the terminal asparaginyl compound of Formula XXII, from step (g) above, undergoes an acylation reaction with a compound of the Formula XXIV to give a Fmoc protected terminal tryptophan compound of Formula XXV(step(h)). The acylation reaction is performed as previously described. The compound of Formula XXIV is readily available via activation of commercially available N-Fmoc-tryptophan. In a preferred embodiment of the invention, $X^3$ is an 10 aryloxy group. In a more preferred embodiment, $X^3$ is a pentafluorphenoxy. Compounds of the Formula XXIV may be obtained and used in the acylation reaction as either a racemic mixture or as a single enantiomer. In a preferred embodiment of the invention the compound of Formula XXIV is enriched with one enantiomer. In a more preferred embodiment of the invention, the compound of Formula XXIV comprises greater than about 50% of one enantiomer. In an even more preferred embodiment of the invention, the compound of Formula XXIV comprises greater than about 75% of one enantiomer. In a still more preferred embodiment of the invention, the compound of Formula XXIV comprises greater than about 90% of one enantiomer. In another more preferred embodiment of the invention, the compound of Formula XXIV comprises greater than about 95% of one enantiomer. In the most preferred embodiment of the invention, the compound of Formula XXIV comprises greater than about 98% of one enantiomer.

The Fmoc protecting group of the Fmoc protected terminal tryptophanyl compound of Formula XXV is removed to afford the terminal tryptophan compound of Formula XXVI (step(i)) according to procedures described in Greene.

The terminal tryptophanyl compound of Formula XXVI is then acylated as previously described, with a compound of Formula XXVII to give the acylated compound of Formula X (step(j)). The compound of Formula XXVII is readily available via activation of decanoic acid. In a preferred embodiment of the invention, $X^4$ is an aryloxy group. In a more preferred embodiment, $X^4$ is a pentafluorophenoxy group.

The compound of Formula X is then converted to a compound of Formula II as described previously (step (k)).

Daptomycin Stereoisomeric Compounds

According to another embodiment, the present invention provides daptomycin stereoisomeric compounds, and pharmaceutically acceptable salts thereof. As shown below, daptomycin has thirteen chiral centers:

(IV)

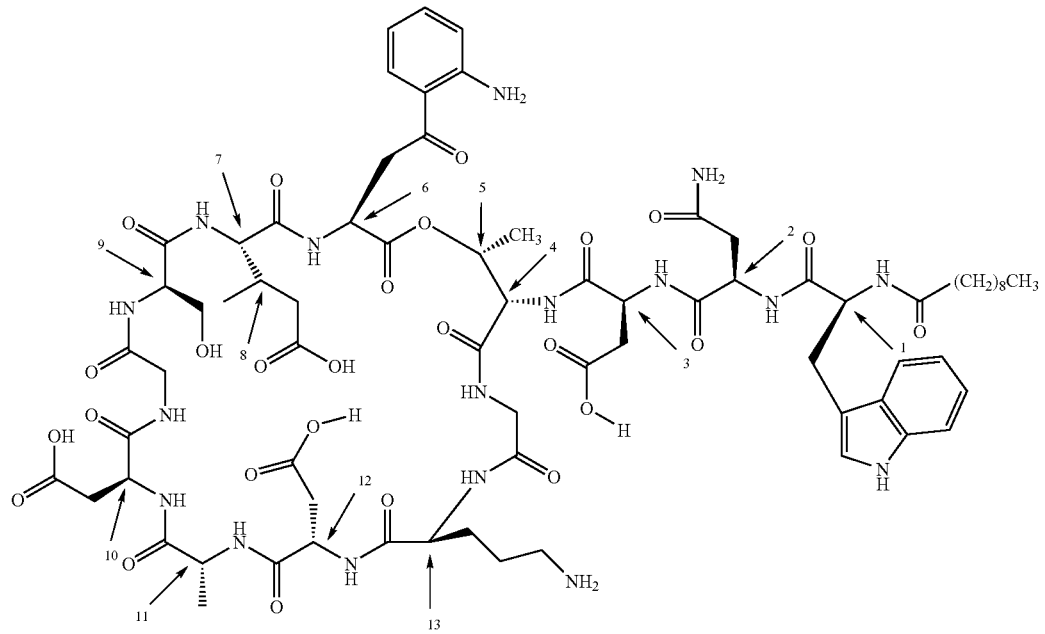

The present invention allows for the absolute configuration at positions 1 and 2 to be varied based on the choice of acylating agents (for example, compounds of the Formulas IX, XX, XXIII, and XXIV).

The present invention provides daptomycin stereoisomeric compounds of the Formula:

and pharmaceutically-acceptable salts thereof.

In preferred embodiments of the invention, the daptomycin stereoisomeric compound includes at least one of the following:

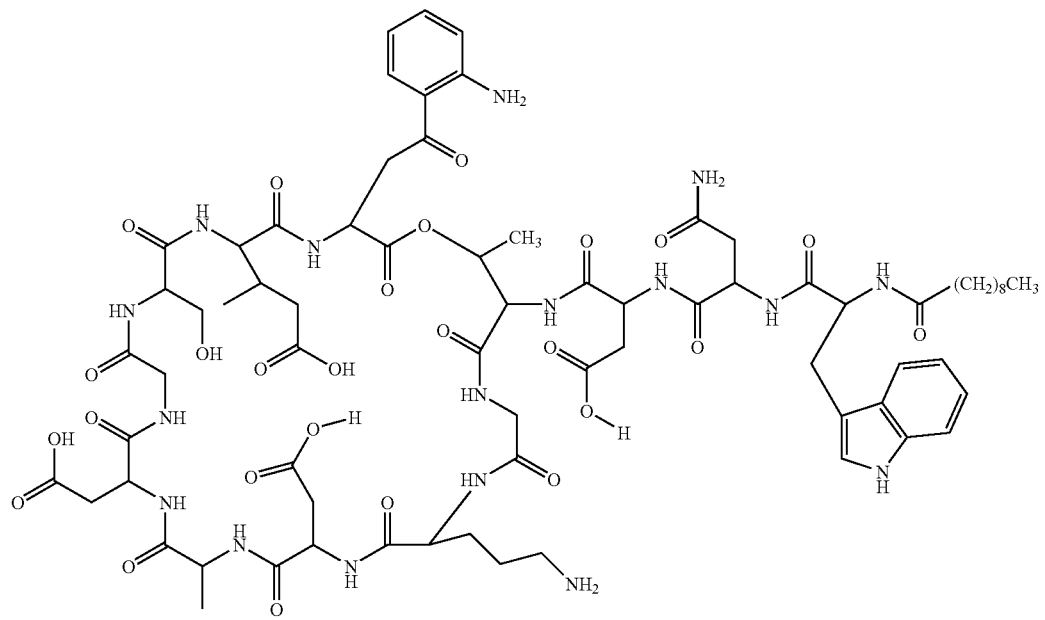

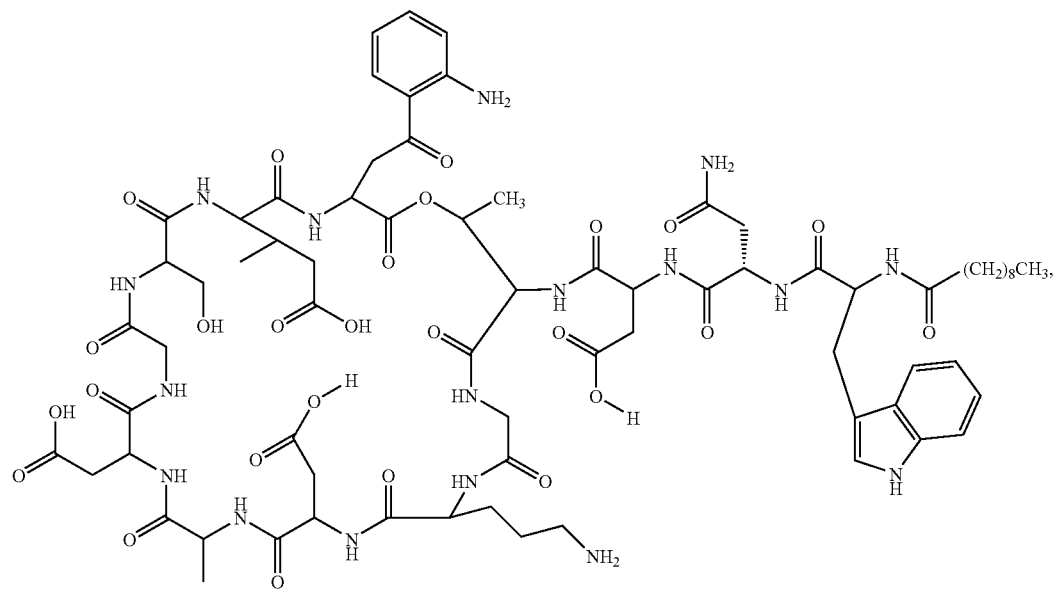
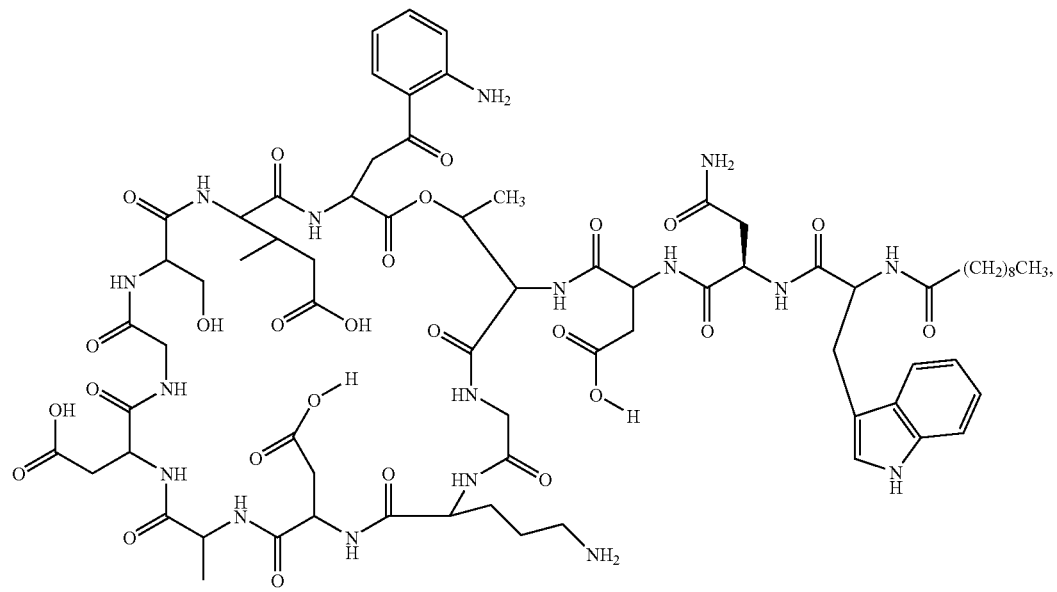

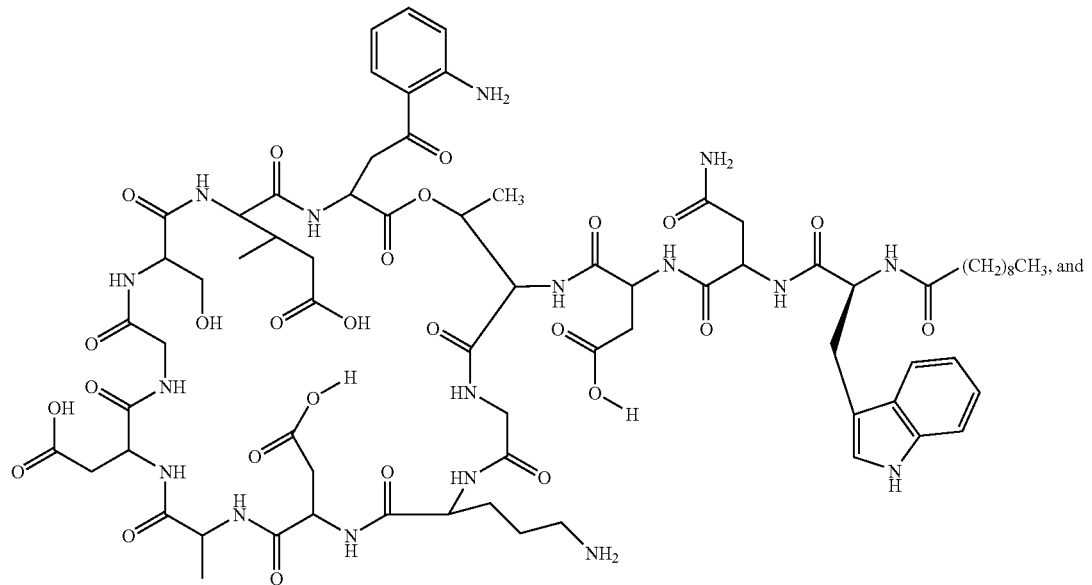
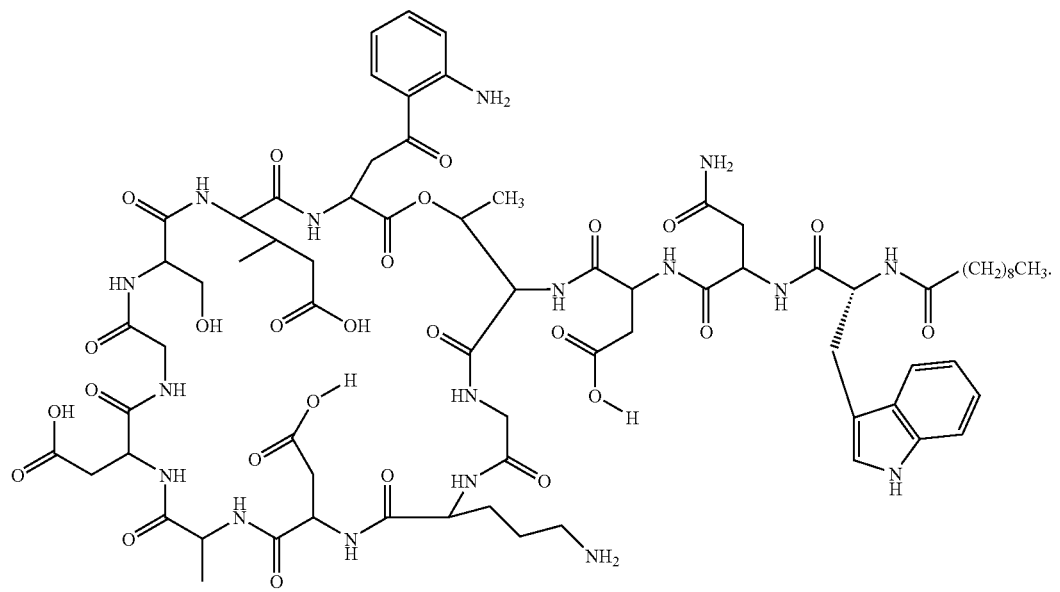

In more preferred embodiments of the invention, the daptomycin stereoisomeric compound includes at least one of the following:
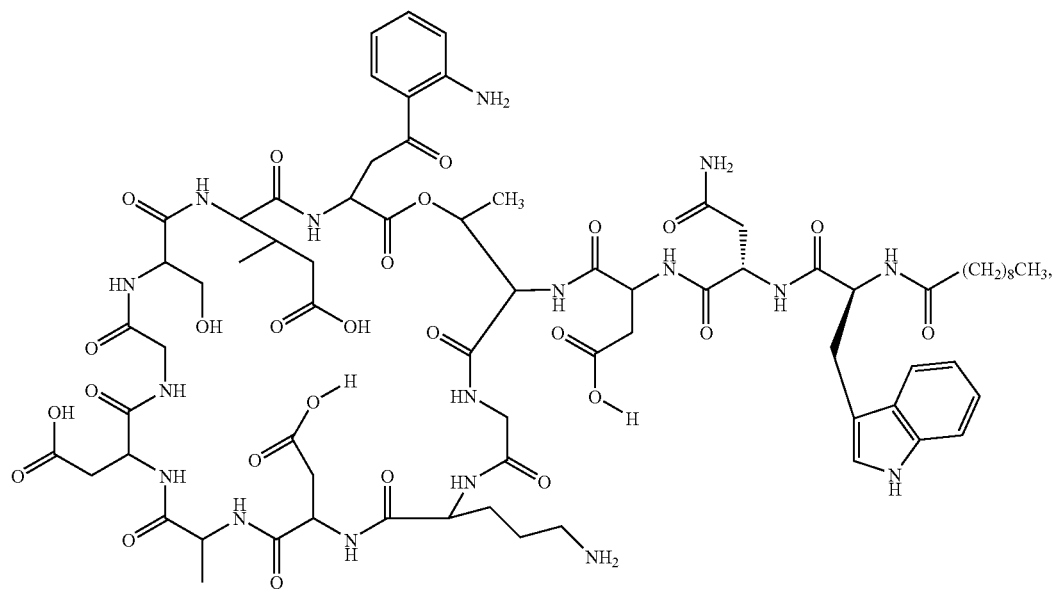
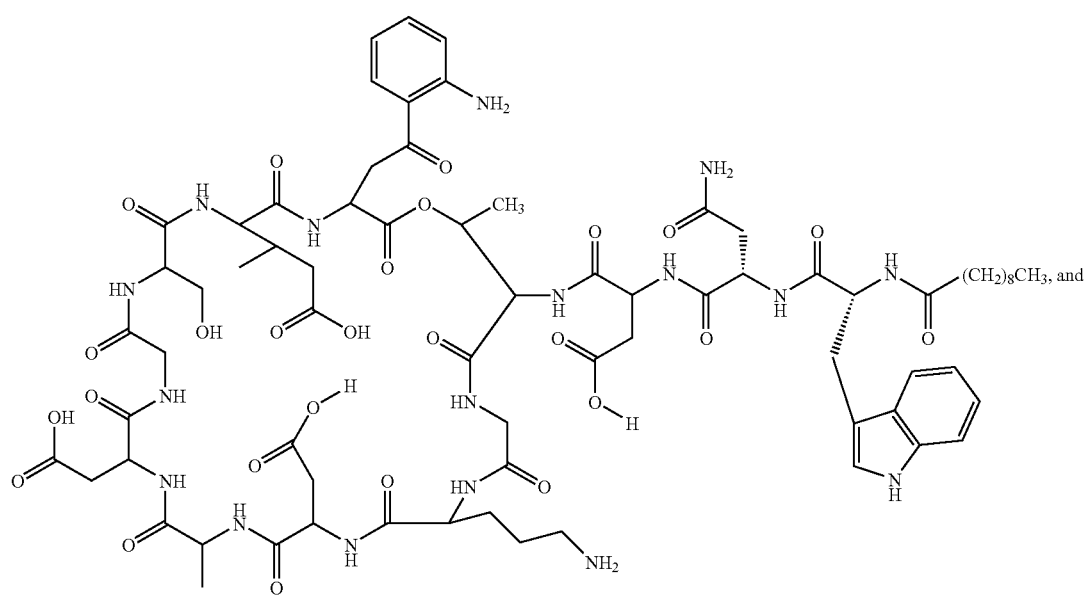

-continued
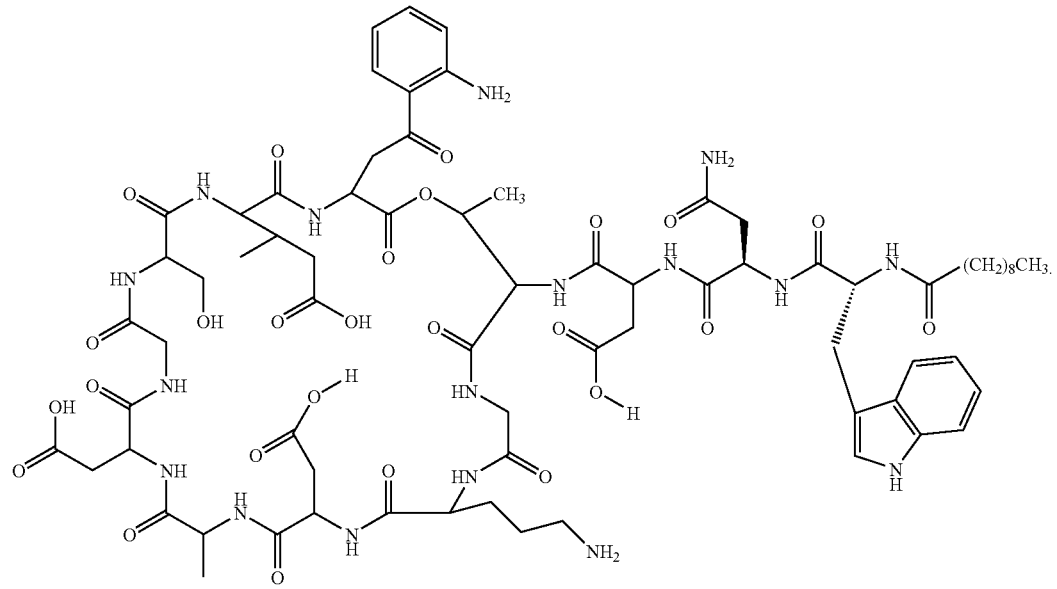
Intermediates
The present invention also provides intermediates useful in the methods of the invention. Intermediates of the present invention include compounds having the structure:
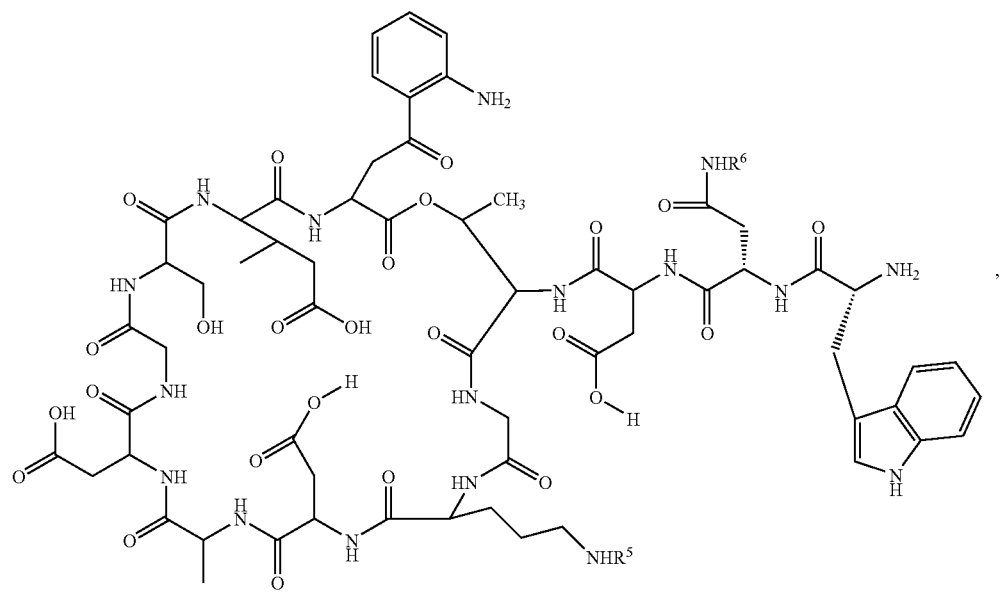

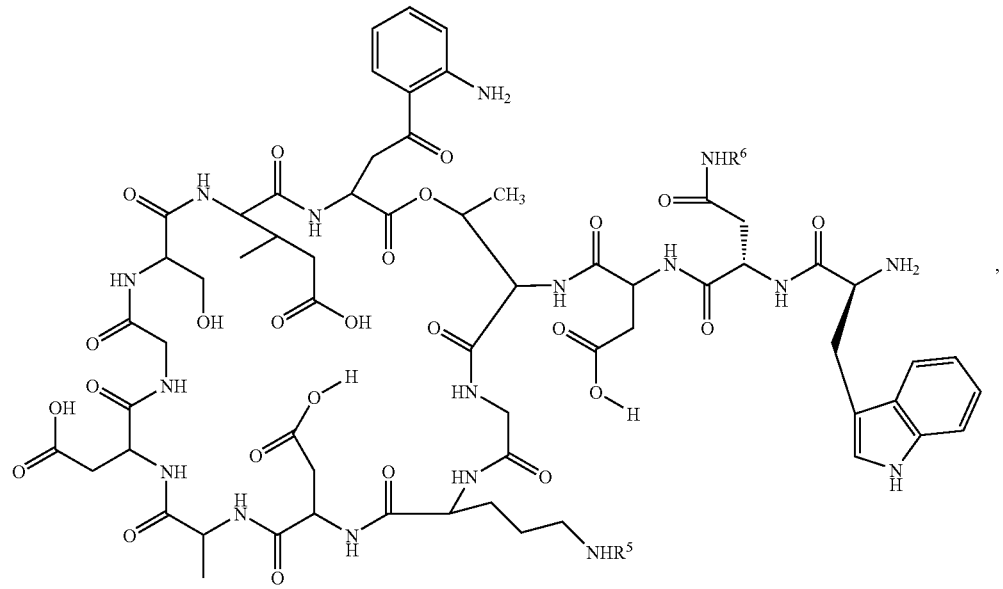
,
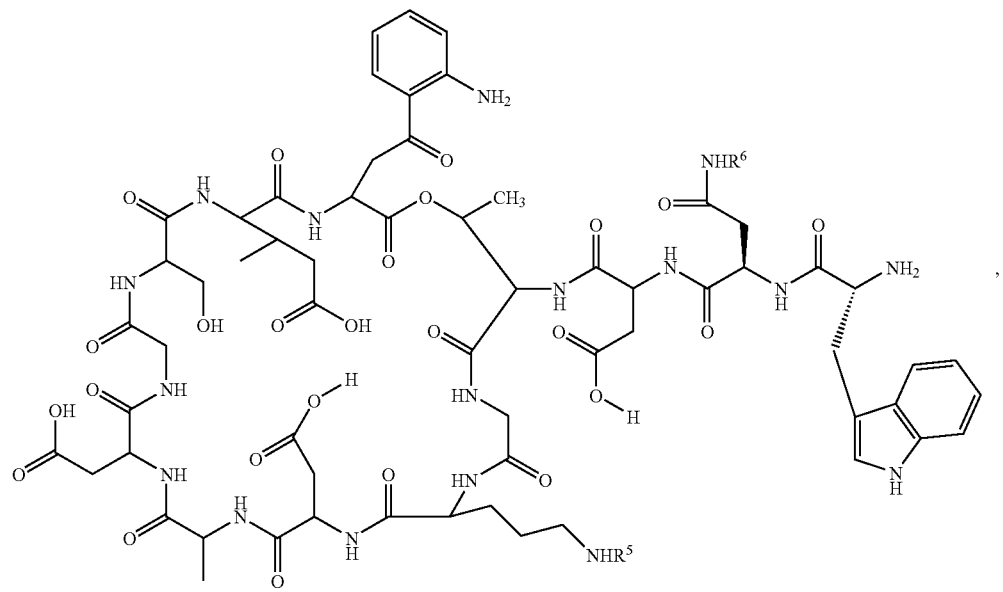
,

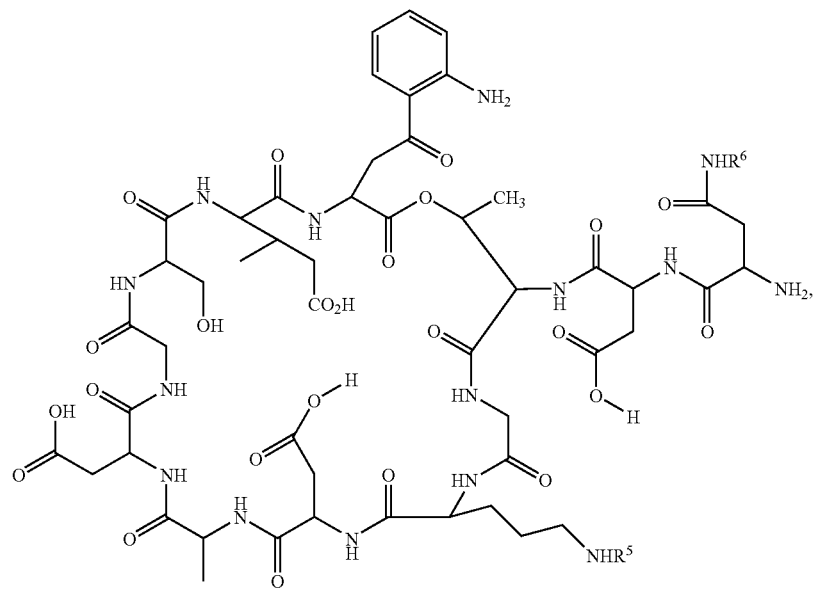
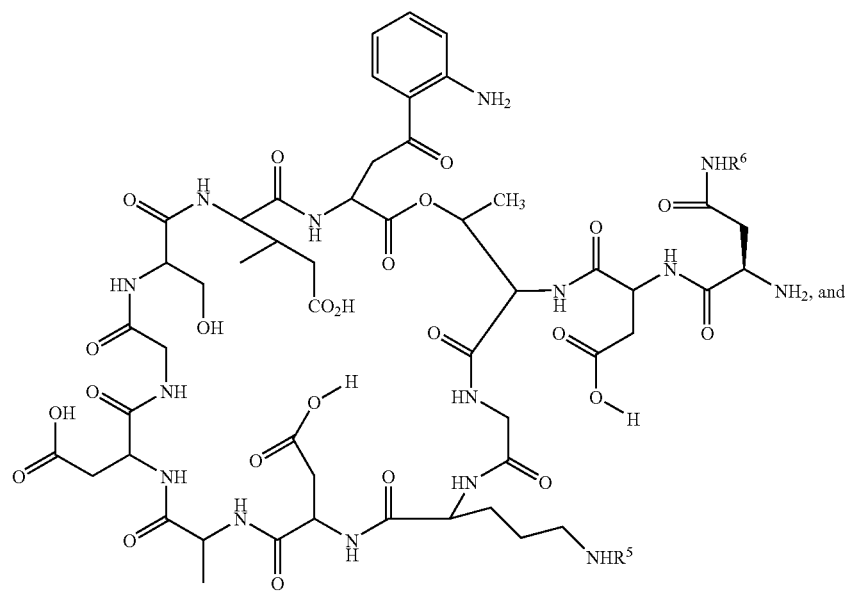

-continued

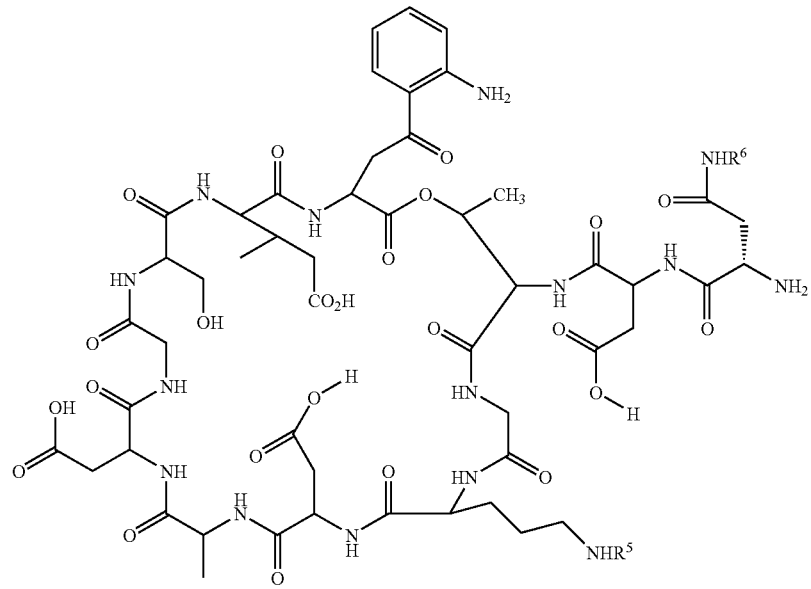

where $R^5$ is an ornithine protecting group and $R^6$ is hydrido or an asparagine protecting group. $R^5$ is preferably allyloxycarbonyl, carbobenzyloxycarbonyl or tert-butoxycarbonyl; most preferably, $R^5$ is allyloxycarbonyl.

Compounds of the Formula VII are particularly useful as intermediates for the preparation of the compounds of Formula II.

where $R^5$ is an ornithine amino protecting group. In preferred embodiments of the invention, $R^5$ is allyloxycarbonyl, carbobenzyloxycarbonyl or tert-butoxycarbonyl. In a most preferred embodiment, $R^5$ is allyloxycarbonyl.

The present invention also provides compounds of the Formula VIII that are particularly useful as intermediates for the preparation of the compounds of Formula II.

VII

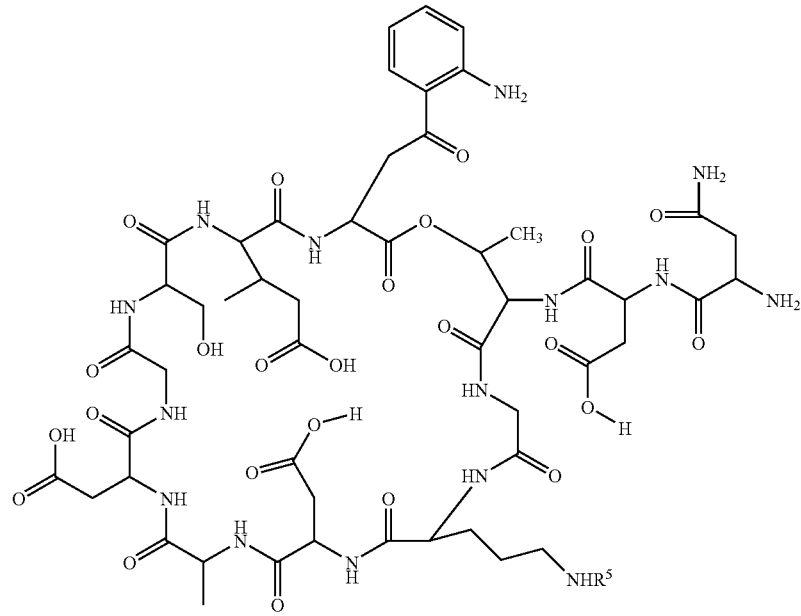

VIII

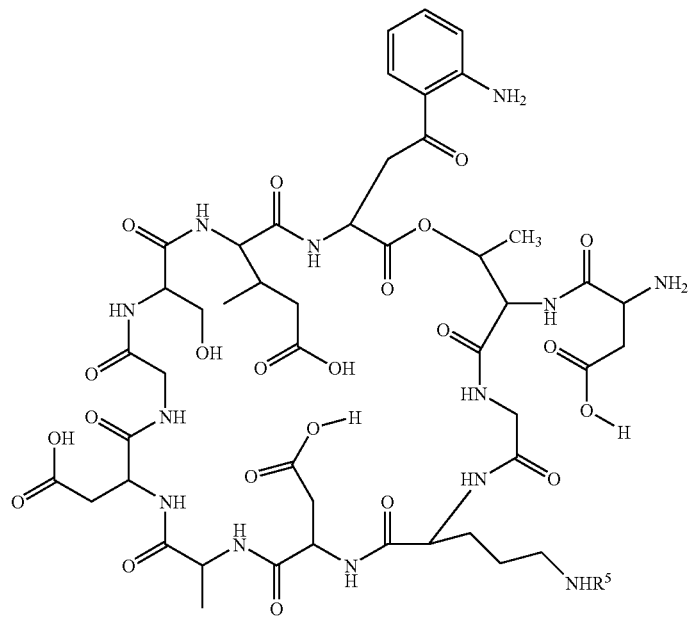

where $R^5$ is an ornithine amino protecting group. In preferred embodiments of the invention, $R^5$ is allyloxycarbonyl, carbobenzyloxycarbonyl or tert-butoxycarbonyl. In a most preferred embodiment, $R^5$ is allyloxycarbonyl.

Pharmaceutical Compositions and Methods of Use Thereof

The present invention also provides pharmaceutical compositions or formulations comprising daptomycin stereoisomeric compounds or salts thereof. Such pharmaceutical compositions or formulations may include one or more daptomycin stereoisomeric compounds, as well as daptomycin itself. The preparation methods of the present invention allow for any desired proportion of daptomycin stereoisomeric compounds and/or daptomycin in pharmaceutical compositions or formulations of the invention.

Daptomycin stereoisomeric compounds, or pharmaceutically acceptable salts thereof, can be formulated for oral, intravenous, intramuscular, subcutaneous or parenteral administration for the therapeutic or prophylactic treatment of diseases, particularly bacterial infections. For oral or parenteral administration, daptomycin stereoisomeric compounds of this invention can be mixed with conventional pharmaceutical carriers and excipients and used in the form of tablets, capsules, elixirs, suspensions, syrups, wafers and the like. Such compositions containing a compound of this invention will contain from about 0.1 to about 99% by weight of the active compound, and more generally from about 10 to about 30%.

The pharmaceutical preparations disclosed herein are prepared in accordance with standard procedures and are administered at dosages that are selected to reduce, prevent or eliminate the infection (See, e. g., Remington's Pharmaceutical Sciences, Mack Publishing Company, Easton, Pa. and Goodman and Gilman's The Pharmaceutical Basis of Therapeutics, Pergamon Press, New York, N.Y., the contents of which are incorporated herein by reference, for a general description of the methods for administering various antimicrobial agents for human therapy). The pharmaceutical compositions or formulations of the invention can be delivered using controlled (e.g., capsules) or sustained release delivery systems (e.g., bioerodable matrices). Exemplary delayed release delivery systems for drug delivery that are suitable for administration of the compositions of the invention (preferably of Formula II) are described in U.S. Pat. Nos. 4,452,775; 5,239,660; and 3,854,480.

The pharmaceutically-acceptable compositions of the present invention comprise one or more compounds of the invention, in association with one or more nontoxic, pharmaceutically-acceptable carriers and/or diluents and/or adjuvants and/or excipients, collectively referred to herein as "carrier" materials, and, if desired, other active ingredients. The compositions may contain common carriers and excipients, such as corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral use, solid formulations such as tablets and capsules are particularly useful. Sustained release or enterically coated preparations may also be devised. For pediatric and geriatric applications, suspensions, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, a daptomycin stereoisomeric compound of the invention can be dissolved or suspended in any of the commonly used intravenous fluids and administered by infusion. Intravenous fluids include, without limitation, physiological saline or Ringer's solution. Intravenous administration may be accomplished by using, without limitation, syringe, minipump or intravenous line.

Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For intramuscular preparations, a sterile formulation including a daptomycin stereoisomeric compound or a suitable soluble salt form of the compound, for example the hydrochloride salt, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular or parental formulation of a daptomycin stereoisomeric compound may be adminstered as a bolus or by slow infusion. A bolus is a dose that is administered in less than 30 minutes. In a preferred embodiment, a bolus is administered in less than 15 or less than 10 minutes. In a more preferred embodiment, a bolus is administered in less than 5 minutes. In an even more preferred embodiment, a bolus is administered in one minute or less. An infusion is a dose that is administered at a rate of 30 minutes or greater. In a preferred embodiment, the infusion is one hour or greater. In another embodiment, the infusion is substantially constant.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution in the appropriate pharmaceutically acceptable carrier at the time of delivery. In another embodiment, the unit dosage form of the compound can be a solution of the compound or preferably a salt thereof in a suitable diluent in sterile, hermetically sealed ampoules or sterile syringes. The concentration of the compound in the unit dosage may vary, e.g. from about 1 percent to about 50 percent, depending on the compound used and its solubility and the dose desired by the physician. If the compositions contain dosage units, each dosage unit preferably contains from 1–500 mg of the active material. For adult human treatment, the dosage employed preferably ranges from 5 mg to 10 g, per day, depending on the route and frequency of administration.

In another aspect, the invention provides a method for inhibiting the growth of microorganisms, preferably bacteria, comprising contacting said organisms with a composition of the invention, under conditions which permit entry of the compound into said organism and into said microorganism. Such conditions are known to one skilled in the art and are exemplified in the Examples. This method involves contacting a microbial cell with a therapeutically-effective amount of a composition of the invention, either in vivo or in vitro.

According to this aspect of the invention, the novel compositions disclosed herein are placed in a pharmaceutically acceptable carrier and are delivered to a recipient subject (preferably a human) in accordance with known methods of drug delivery. In general, the methods of the invention for delivering the compositions of the invention in vivo utilize art-recognized protocols for delivering the agent with the only substantial procedural modification being the substitution of the compounds of the invention for the drugs in the art-recognized protocols. Likewise, the methods for using the claimed composition for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the invention for the agents used in the art-recognized protocols.

In one embodiment, the invention provides a method for treating an infection, especially those caused by gram-positive bacteria, in a subject with a therapeutically-effective amount of a composition of the present invention. Exemplary procedures for delivering an antibacterial agent are described in U.S. Pat. No. 5,041,567, issued to Rogers and in PCT patent application number EP94/02552 (publication no. WO 95/05384), the entire contents of which documents are incorporated in their entirety herein by reference. As used herein the phrase "therapeutically-effective amount" means an amount of a composition of the present invention that prevents the onset, alleviates the symptoms, or stops the progression of a bacterial infection. The term "treating" is defined as administering, to a subject, a therapeutically-effective amount of a compound of the invention both to prevent the occurrence of an infection and to control or eliminate an infection. The term "subject", as described herein, is defined as a mammal, a plant or a cell culture. In a preferred embodiment, a subject is a human or other animal patient.

The method comprises administering to the subject an effective dose of a composition of this invention. An effective dose is generally between about 0.1 and about 100 mg/kg of a composition of the invention. A preferred dose is from about 0.1 to about 50 mg/kg of a composition containing a daptomycin stereoisomeric compound or pharmaceutically acceptable salt thereof. A more preferred dose is from about 1 to 25 mg/kg of a composition containing a daptomycin stereoisomeric compound or pharmaceutically acceptable salt thereof. An effective dose for cell culture is usually between 0.1 and 1000 µg/mL, more preferably between 0.1 and 200 µg/mL.

A composition containing a daptomycin stereoisomeric compound of the invention can be administered as a single daily dose or in multiple doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the compound and the microorganism or microorganisms involved in the infection. A method of administration to a patient of daptomycin is disclosed in U.S. Ser. No. 09/406,568, filed Sep. 24, 1999, which claims the benefit of U.S. Provisional Application Nos. 60/101,828, filed Sep. 25, 1998, and 60/125,750, filed Mar. 24, 1999, the contents of which are herein incorporated by reference.

A composition containing a daptomycin stereoisomeric compound according to this invention may also be administered in the diet or feed of a patient or animal. If administered as part of a total dietary intake, the amount of compound employed can be less than 1% by weight of the diet and preferably no more than 0.5% by weight. The diet for animals can be normal foodstuffs to which the compound can be added or it can be added to a premix.

The methods of the present invention provide administering a composition containing a daptomycin stereoisomeric compound to a subject in need thereof in an amount that is efficacious in reducing or eliminating the bacterial infection. The composition may be administered orally, parenterally, by inhalation, topically, rectally, nasally, buccally, vaginally, or by an implanted reservoir, external pump or catheter. The composition may be prepared for opthalmic or aerosolized uses. The compositions of the present invention can be administered as an aerosol for the treatment of pneumonia or other lung-based infections. A preferred aerosol delivery vehicle is an anhydrous or dry powder inhaler. Compositions containing a daptomycin stereoisomeric compound also may be directly injected or administered into an abscess, ventricle or joint. Parenteral administration includes subcutaneous, intravenous, intramuscular, intra-articular, intra-synovial, cisternal, intrathecal, intrahepatic, intralesional and intracranial injection or infusion. In a preferred embodiment, compositions containing a daptomycin stereoisomeric compound are administered intravenously, subcutaneously or orally. In a preferred embodiment for administering a composition of the invention to a cell culture, the composition may be administered in a nutrient medium.

The method of the instant invention may be used to treat a subject having a bacterial infection in which the infection is caused or exacerbated by any type of bacteria, particularly gram-positive bacteria. In one embodiment, a composition containing a daptomycin stereoisomeric compound is administered to a patient according to the methods of this invention. In a preferred embodiment, the bacterial infection may be caused or exacerbated by gram-positive bacteria. These gram-positive bacteria include, but are not limited to, methicillin-susceptible and methicillin-resistant staphylococci (including *Staphylococcus aureus, S. epidermidis, S. haemolyticus, S. hominis, S. saprophyticus*, and coagulase-negative staphylococci), glycopeptide intermediary-susceptible *S. aureus* (GISA), penicillin-susceptible and penicillin-resistant *streptococci* (including *Streptococcus pneumoniae, S. pyogenes, S. agalactiae, S. avium, S. bovis, S. lactis, S. sangius* and *Streptococci* Group C, *Streptococci* Group G and viridans *streptococci*), enterococci (including vancomycin-susceptible and vancomycin-resistant strains such as *Enterococcus faecalis* and *E. faecium*), *Clostridium difficile, C. clostridiiforme, C. innocuum, C. perfringens, C. ramosum, Haemophilus influenzae, Listeria monocytogenes, Corynebacterium jeikeium, Bifidobacterium* spp., *Eubacterium aerofaciens, E. lentum, Lactobacillus acidophilus, L. casei, L. plantarum, Lactococcus* spp., *Leuconostoc* spp., *Pediococcus, Peptostreptococcus anaerobius, P. asaccarolyticus, P. magnus, P. micros, P. prevotii, P. productus, Propionibacterium acnes, Actinomyces* spp., *Moraxella* spp. (including *M. catarrhalis*) and *Escherichia* spp. (including *E. coli*).

In a preferred embodiment, the antibacterial activity of daptomycin stereoisomeric compounds of Formula II against classically "resistant" strains is comparable to that against classically "susceptible" strains in in vitro experiments. In another preferred embodiment, the minimum inhibitory concentration (MIC) value for daptomycin stereoisomeric compounds according to this invention against susceptible strains is typically the same as or lower than that of vancomycin. Thus, in a preferred embodiment, a composition containing a daptomycin stereoisomeric compound is administered according to the methods of this invention to a patient who exhibits a bacterial infection that is resistant to other compounds, including vancomycin or daptomycin. In addition, unlike glycopeptide antibiotics, lipopeptide compounds exhibits rapid, concentration-dependent bactericidal activity against gram-positive organisms. Thus, in a preferred embodiment, a composition containing a daptomycin stereoisomeric compound is administered to a patient in need of rapidly acting antibiotic therapy.

The administration methods of the instant invention may be used for any bacterial infection of any organ or tissue in the body. In a preferred embodiment, the bacterial infection is caused by gram-positive bacteria. These organs or tissue include, without limitation, skeletal muscle, skin, bloodstream, kidneys, heart, lung and bone. The method of the invention may be used to treat, without limitation, skin and soft tissue infections, bacteremia and urinary tract infections. The methods of the invention may be used to treat respiratory infections, such as otitis media, sinusitis, chronic bronchitis and pneumonia, including pneumonia caused by drug-resistant *S. pneumoniae* or *H. influenzae*. The methods of the invention also may be used to treat mixed infections that comprise different types of gram-positive bacteria, or which comprise both gram-positive and gram-negative bacteria. These types of infections include intra-abdominal infections and obstetrical/gynecological infections. The methods of the invention also may be used to treat an infection including, without limitation, endocarditis, nephritis, septic arthritis, intra-abdominal sepsis, bone and joint infections, and osteomyclitis. In a preferred embodiment, any of the above-described conditions may be treated using a composition containing a daptomycin stereoisomeric compound.

The methods of the instant invention may also be practiced while concurrently administering one or more other antimicrobial agents, such as antibacterial agents (antibiotics) or antifungal agents. As described above, the method may be practiced by administering a composition containing a daptomycin stereoisomeric compound and another lipopeptide compound, such as daptomycin or any other lipopeptide compound.

In one embodiment, the administration methods of the invention include co-administration of antifungal or other antibacterial agents. Antibacterial agents and classes thereof that may be co-administered with daptomycin stereoisomeric compounds or other lipopeptide antibiotics include, without limitation, penicillins and related drugs, carbapenems, cephalosporins and related drugs, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, everninomycin, glycopeptide, glycylcylcline, ketolides, oxazolidinone; imipenen, amikacin, netilmicin, fosfomycin, gentamicin, ceftriaxone, Ziracin, LY 333328, CL 331002, HMR 3647, Zyvox, Synercid, Aztreonam, and Metronidazole, Epiroprim, OCA-983, GV-143253, Sanfetrinem sodium, CS-834, Biapenem, A-99058.1, A-165600, A-179796, KA 159, Dynemicin A, DX8739, DU 6681; Cefluprenam, ER 35786, Cefoselis, Sanfetrinem celexetil, HGP-31, Cefpirome, HMR-3647, RU-59863, Mersacidin, KP 736, Rifalazil; AM 1732, MEN 10700, Lenapenem, BO 2502A, NE-1530, PR 39, K130, OPC 20000, OPC 2045, Veneprim, PD 138312, PD 140248, CP 111905, Sulopenem, ritipenam acoxyl, RO-65-5788, Cyclothialidine, Sch-40832, SEP-132613, micacocidin A, SB-275833, SR-15402, SUN A0026, TOC 39, carumonam, Cefozopran, Cefetamet pivoxil, and T 3811.

Antifungal agents that may be co-administered with daptomycin stereoisomeric compounds or other lipopeptide antibiotic include, without limitation, Caspofungen, Voriconazole, Sertaconazole, IB-367, FK-463, LY-303366, Sch-56592, Sitafloxacin, DB-289 polyenes, such as Amphotericin, Nystatin, Primaricin; azoles, such as Fluconazole, Itraconazole, and Ketoconazole; allylamines, such as Naftifine and Terbinafine; and anti-metabolites such as Flucytosine. Other antifungal agents include without limitation, those disclosed in Fostel et al., Drug Discovery Today 5:25–32 (2000), herein incorporated by reference. Fostel et al. discloses antifungal compounds including Corynecandin, Mer-WF3010, Fusacandins, Artrichitin/LL 15G256, Sordarins, Cispentacin, Azoxybacillin, Aureobasidin and Khafrefungin.

Compositions containing a daptomycin stereoisomeric compound may be administered according to methods of the invention until the bacterial infection is eradicated or reduced. In one embodiment, a composition containing a daptomycin stereoisomeric compound is administered for a period of time from 2 days to 6 months. In a preferred embodiment, a composition containing a daptomycin stereoisomeric compound is administered for 7 to 56 days. In a more preferred embodiment, a composition containing a daptomycin stereoisomeric compound is administered for 7 to 28 days. In an even more preferred embodiment, a daptomycin stereoisomeric compound is administered for 7 to 14 days. Compositions containing a daptomycin stereoisomeric compound may be administered for a longer or shorter time period if it is so desired.

The following examples are provided for the purpose of illustration only and are not to be construed as limiting the scope of the invention in any way.

EXAMPLES

Determination of the Absolute Sterochemical Configuration of Daptomycin

As a preliminary study, daptomycin was hydrolyzed and run on an HPLC system equipped with a column for separating L and D amino acid residues. This data suggested the presence of both L-Asp and D-Asp residues; however, the results did not suggest the presence of a racemic mixture for the remaining residues of daptomycin. Because complete hydrolysis of daptomycin may cause racemization of the amino acids present, further analysis was performed to confirm these preliminary results.

The following approach was used to cleave daptomycin into the two peptides shown:

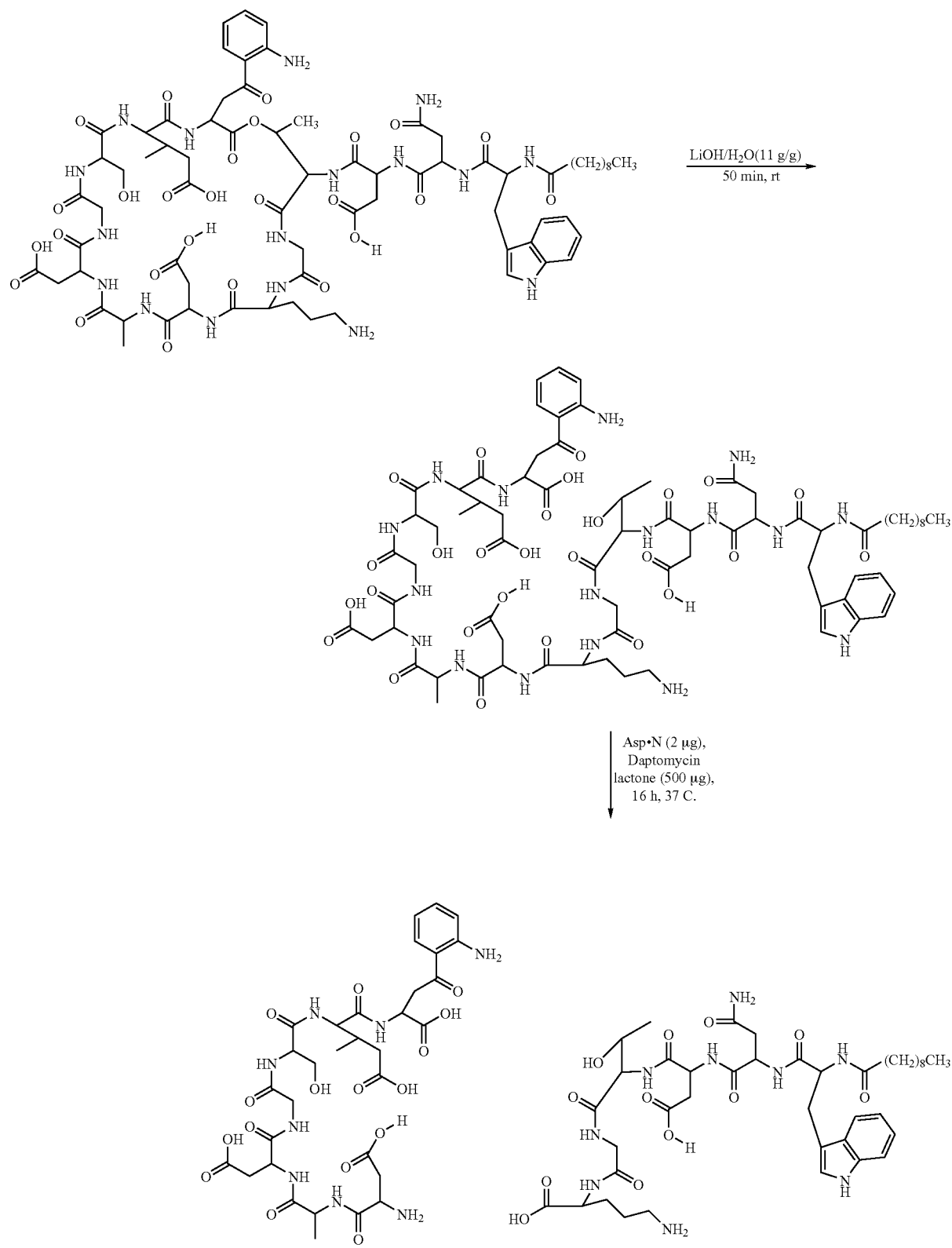

Briefly, daptomycin obtained from *S. roseosporus* was hydrolyzed at ambient temperature with lithium to produce an open-ringed molecule, daptomycin lactone. This hydrolysis was followed by enzymatic digestion with Asp-N for 16 hours at 37° C., resulting in the two peptides (a "ring" peptide (left) and a "tail" peptide (right)) shown above. To confirm the absolute stereochemical configuration of the Asp residue of the "tail" peptide, synthetic peptides were prepared, one having a D-Asp residue, the other having a L-Asp residue. HPLC analysis confirmed that the cleaved "tail" peptide contains a D-Asp residue, thus confirming that daptomycin contains D-Asp in the peptide tail.

Preparation of Acylating Agents

Example 1

Synthesis of Compound E

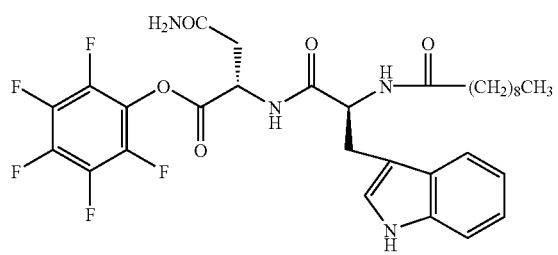

E

Reaction 1

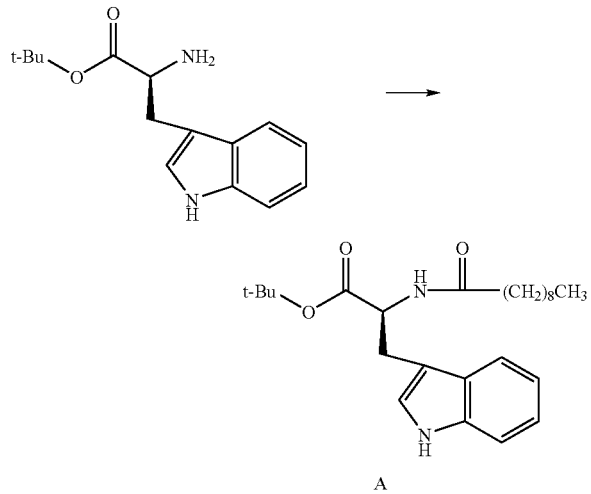

To a solution of commercially available L-tryptophan-t-butyl ester hydrochloride (3.07 g), decanoic acid (3.19 g) and diisopropylethylamine (12.3 ml) in dry tetrahydrofuran (100 ml) was added 1-(3-dimethylaminopropyl)-3-ethylcarbodiimide hydrochloride (2.92 g). The reaction mixture was stirred at room temperature for 18 hours before partitioning between 1 M hydrochloric acid (150 ml) and ethyl acetate (150 ml). The organic layer was washed with saturated sodium chloride (150 ml), dried with anhydrous sodium sulfate and evaporated to dryness to give compound A (6 g).

Reaction 2

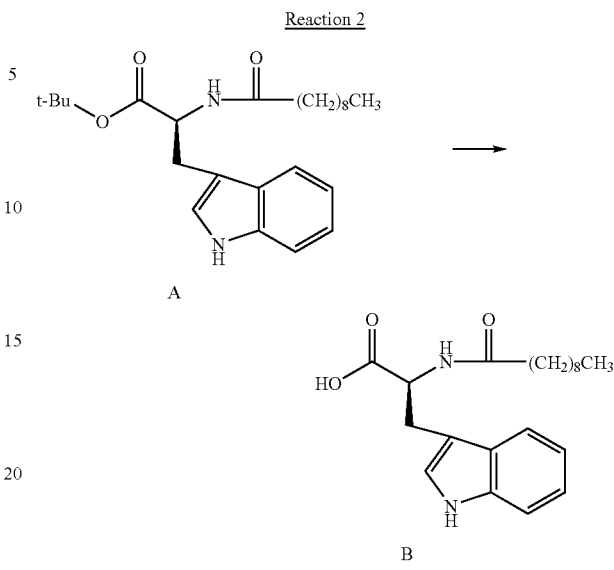

Compound A (6 g) and ethanedithiol (200 µl) were stirred in 25% trifluoroacetic acid in dry dichloromethane (60 ml) at room temperature for 4 hours. The solvent was evaporated and the residue was purified on silica gel using ethyl acetate as eluent to give compound B as an oil (5 g).

Reaction 3

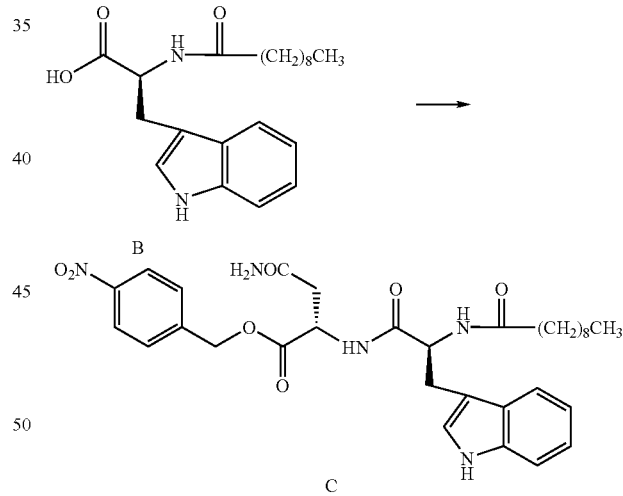

To a solution of compound B (1.13 g), L-asparagine-4-nitrobenzyl ester hydrobromide(1.10 g) and diisopropylethylamine (3.3 ml) in dry tetrahydrofuran (50 ml) was added 1-(3-dimethylaminopropyl)-3-ethylcarbodiimide hydrochloride (0.75 g). The reaction mixture was stirred at room temperature for 18 hours before partitioning between 1 M hydrochloric acid (100 ml) and ethyl acetate (100 ml). The organic layer was washed with saturated sodium chloride (100 ml) then dried with anhydrous sodium sulfate. After evaporation to dryness the residue was triturated with diethylether (30 ml) to give compound C as a yellow solid 0.81 g.

Reaction 4

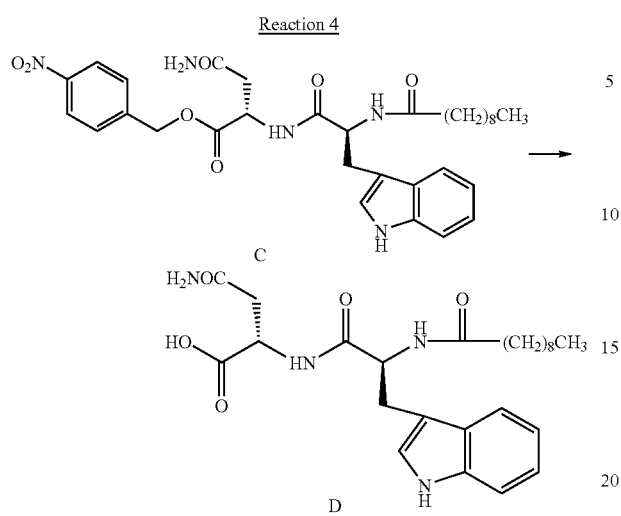

Compound C (0.8 g) and 10% palladium on carbon (0.4 g) were stirred at room temperature in 1:1 ethylacetate/tetrahydrofuran (100 ml) under hydrogen at 1 atmosphere for 24 hours. The catalyst was filtered off and the filtrate was evaporated to dryness. The residue was triturated with diethylether (20 ml) to give compound D as a yellow solid (0.45 g).

Reaction 5

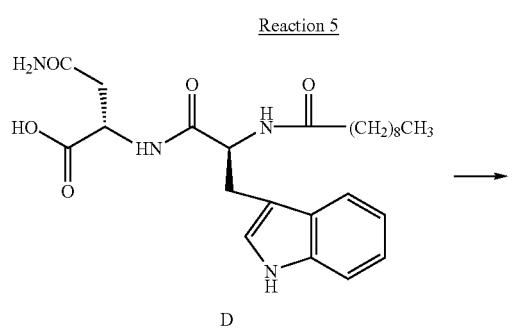

To a solution of compound D (0.45 g) and pentafluorophenol (0.18 g) in dry tetrahydrofuran (25 ml) was added dicyclohexylcarbodiimide (0.20 g). The reaction mixture was stirred at room temperature for 18 hours before being diluted with hexanes (25 ml) and filtered. The filtrate was evaporated to dryness to give compound E as an oil (0.60 g).

Example 2

Synthesis of Compound L

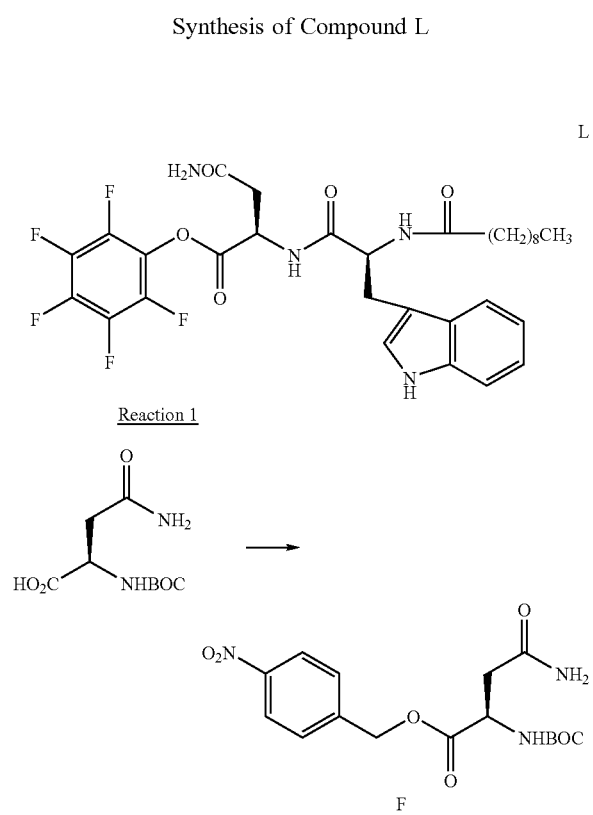

To a stirred solution of commercially available N-Boc-D-Asparagine (4 g), 4-nitrobenzyl alcohol (2.9 g) and triphenylphosphine (6.77 g) in dry tetrahydrofuran (200 ml) was added diisopropylazodicarboxylate (3.81 g) at room temperature. The reaction mixture was stirred for 24 hours. The mixture was diluted with ethyl acetate (100 ml), washed with water (50 ml) and saturated sodium chloride (50 ml). The organic layer was dried over anhydrous sodium sulfate and evaporated to dryness. The residue was triturated with diethylether (50 ml) to give compound F as a white solid (4.3 g).

Reaction 2

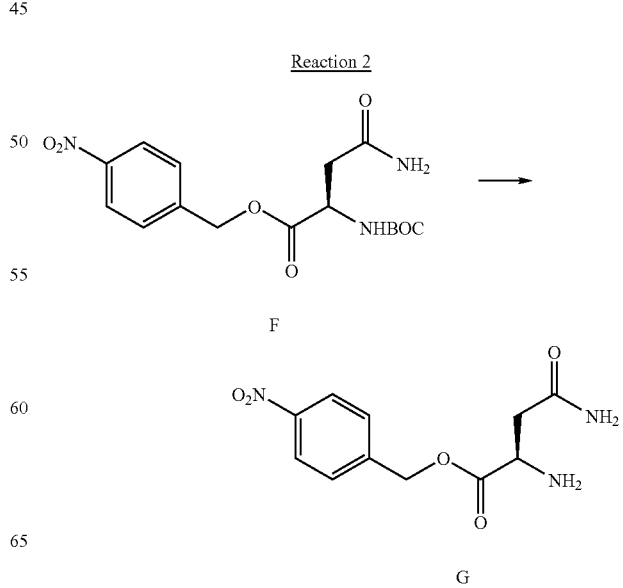

Compound F (2 g) and 1,2-ethanedithiol (0.2 ml) were stirred in trifluoroacetic acid (2 ml) and dry dichloromethane (8 ml) at room temperature for 4 hours before being evaporated to dryness. The residue was purified by silica gel chromatography eluting with 15% methanol/dichloromethane to give the compound G as a white solid (1.2 g).

Compound H (3.65 g) and 10% palladium on carbon (0.5 g) in ethylacetate (50 ml) and tetrahydrofuran (50 ml) were stirred under 1 atmosphere of hydrogen for 24 hours at room temperature before the catalyst was filtered off. Evaporation to dryness gave a residue, which was triturated with diethylether to give compound I (2.04 g).

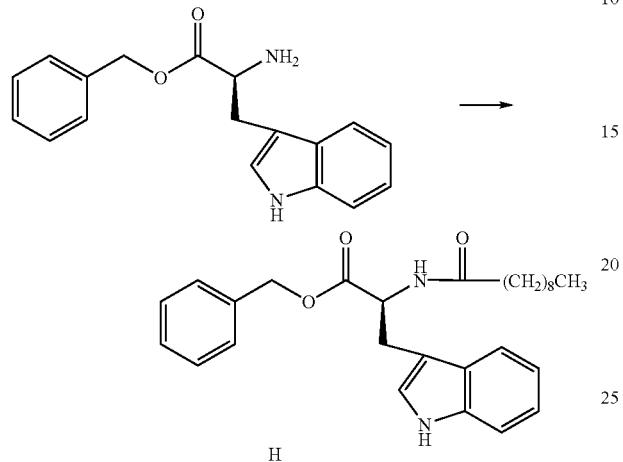

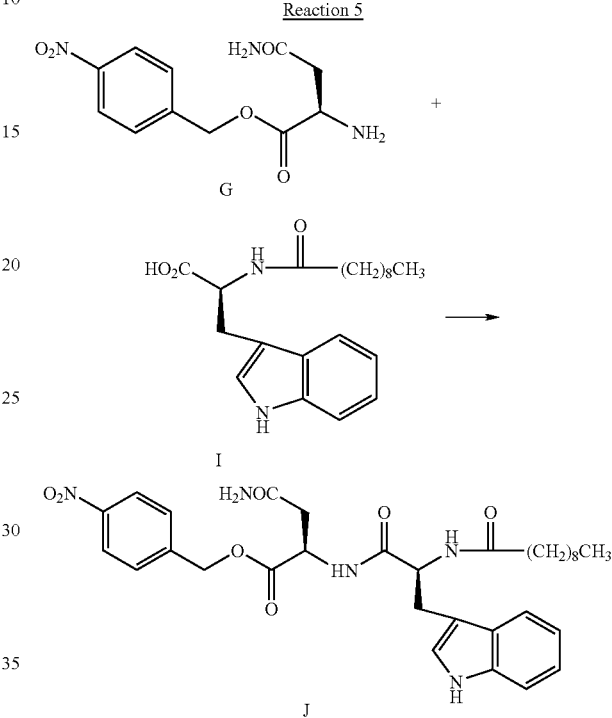

To a stirred solution of commercially available L-tryptophan benzyl ester hydrochloride (6.62 g), decanoic acid (3.79 g) and diisopropylethylamine (20 ml) in dry tetrahydrofuran (300 ml) was added 1-(3-dimethylaminopropyl)-3-ethylcarbodiimde hydrochloride (4.66 g). The reaction mixture was stirred at room temperature for 24 hours before being partitioned between 1 M hydrochloric acid (150 ml) and ethyl acetate (150 ml). The organic layer was washed with saturated sodium chloride (100 ml) and dried with sodium sulfate. Evaporation to dryness gave a residue. The residue was purified by silica gel chromatography eluting with 5% methanol/dichloromethane to give compound H as a light yellow oil (5.85 g).

To a stirred solution of compound G (1.5 g), compound I (2.0 g) and diisopropylethylamine (5.8 ml) in dry tetrahydrofuran (100 ml) was added 1-(3-dimethylaminopropyl)-3-ethylcarbodiimde hydrochloride (2.6 g). The reaction mixture was stirred at room temperature for 24 hours before being partitioned between 1 M hydrochloric acid (150 ml) and ethyl acetate (150 ml). The organic layer was washed with saturated sodium chloride (100 ml) and dried with sodium sulfate. Evaporation of the solvents gave a residue, which was triturated with diethylether to give compound J as the light brown solid (705 mg).

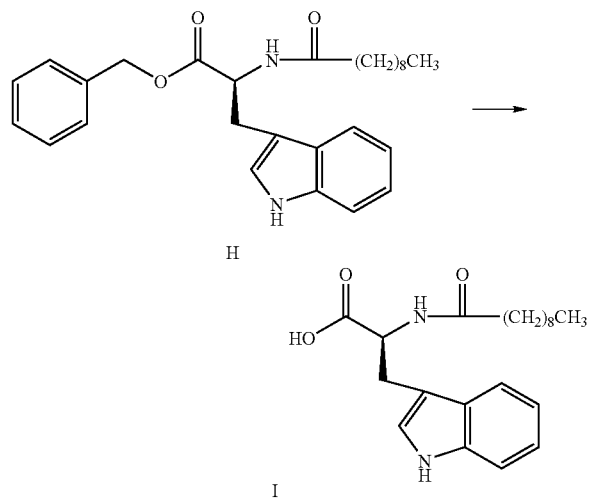

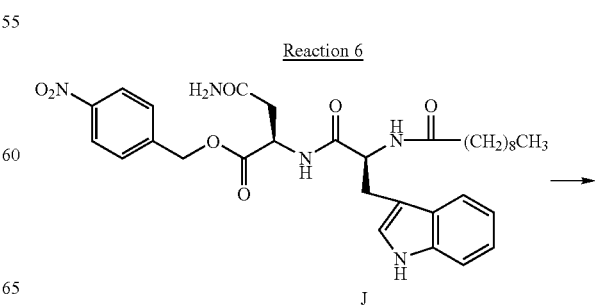

-continued

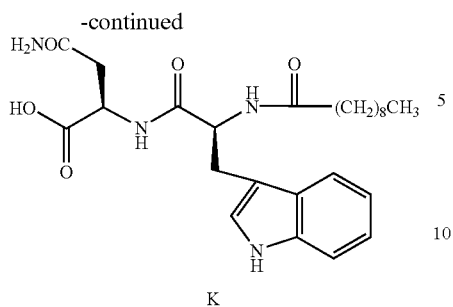

K

Compound J (400 mg) and 10% palladium on carbon (40 mg) in ethylacetate (10 ml) and tetrahydrofuran (10 ml) were stirred under 1 atmosphere of hydrogen at room temperature for 24 hours before filtering off the palladium catalyst. Evaporation of the solvents gave a residue, which was triturated with diethylether to give compound K (125 mg).

Reaction 7

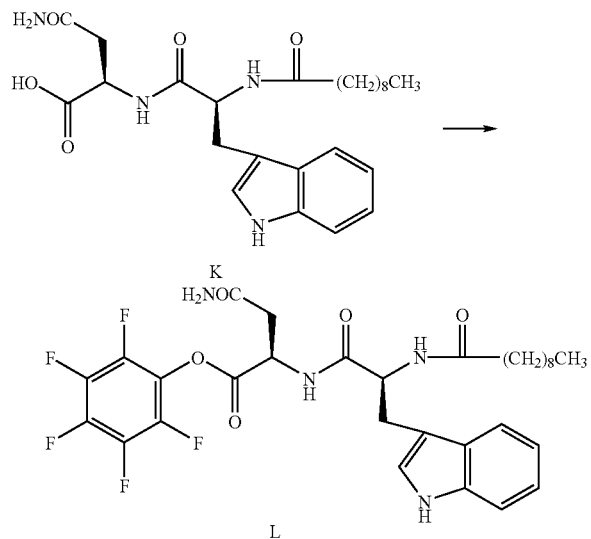

To a stirred solution of compound K (50 mg) and pentafluorophenol (20 mg) in dry tetrahydrofuran (3 ml) was added dicyclohexylcarbodiimide (21 mg). The reaction mixture was stirred at room temperature for 2 hours before being filtered off. Evaporation of the solvent gave compound L which was used without further purification.

Example 3

Synthesis of Compound R

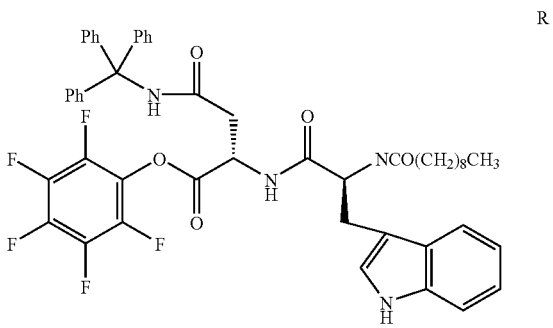

R

General Procedure A Coupling of an Acid to a Resin.

A 0.5 M solution of the acid (2 ml) was added to 0.2 mmol of resin. To this mixture a 0.5 M solution of 1-hydroxybenzotriazole (2 ml), and a 0.5 M solution of 1,3-diisopropylcarbodiimide (2 ml) were added and the mixture was shaken for 90 mins at room temperature. The resin was then filtered and washed with 1-methyl-2-pyrrolidinone (3×6 ml), methanol (3×6 ml), and 1-methyl-2-pyrrolidinone (3×6 ml). Reaction completion was determined by a negative (yellow) Kaiser test. If the test remained positive the coupling procedure was repeated until negative.

General Procedure B Fmoc deprotection on a resin.

The resin (0.2 mmol) was shaken with 20% piperidine in 1-methyl-2-pyrrolidinone (6 ml) for 5 mins. The resin was filtered and shaken with 20% piperidine in 1-methyl-2-pyrrolidinone (6 ml) for 40 mins. The resin was then filtered and washed with 1-methyl-2-pyrrolidinone (3×6 ml), methanol (3×6 ml), and 1-methyl-2-pyrrolidinone (3×6 ml). Reaction completion was determined by a positive (blue) Kaiser test.

Reaction 1

-continued

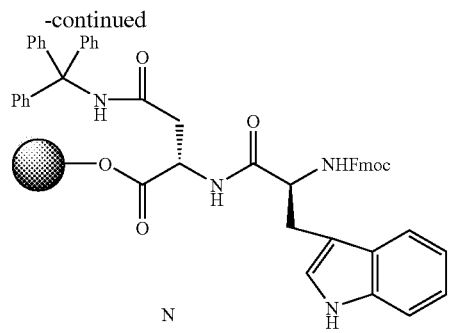

N-Fmoc protected-L-tryptophan in 1-methyl-2-pyrrolidinone was coupled to the commercially available trityl protected-L-asparagine 2-chlorotrityl resin (Advanced ChemTech: Louisville, Ky.) according to the general procedure A above to give resin N.

Reaction 2

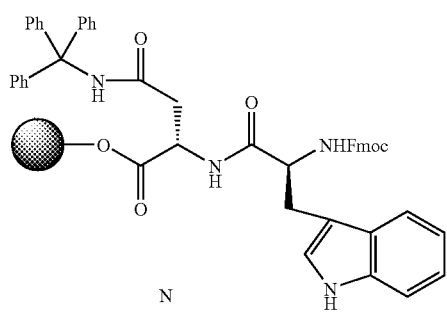

N

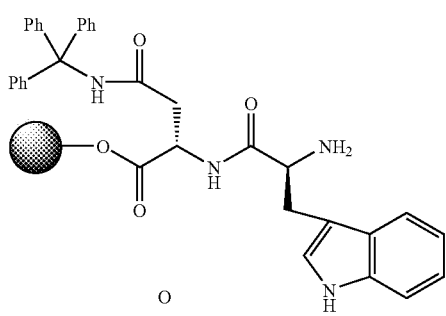

O

The tryptophan Fmoc protecting group was then removed from resin N using general procedure B above to give resin O.

Reaction 3

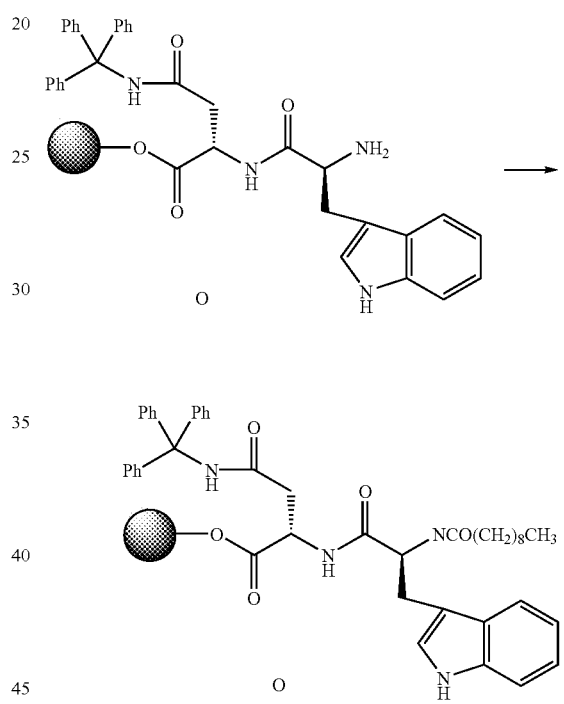

Decanoic acid in 1-methyl-2-pyrrolidinone was coupled to resin O using general procedure A above. The resin was then washed with dry dichloromethane (2×6 ml), and air dried overnight to give resin P.

Reaction 4

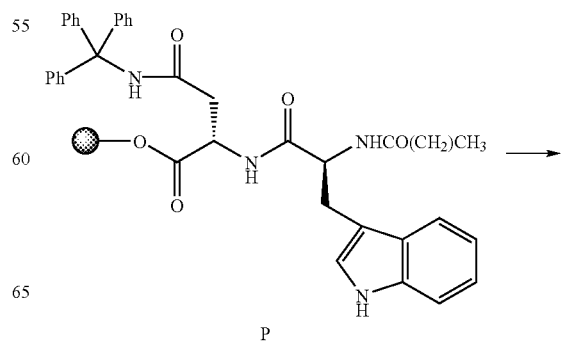

P

-continued

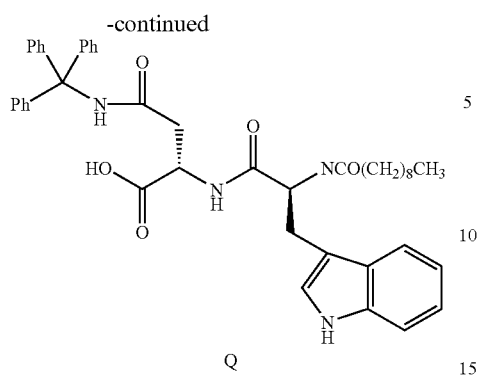

Q

Resin P was treated with dry dichloromethane:trifluoroethanol: acetic acid 18:6:6 (30 ml) for 3.5 hours at room temperature. The resin was filtered, washed with of 1:1 dry dichloromethane:trifluoroethanol (20 ml), and the combined filtrates were evaporated. The residue was then repeatedly dissolved and evaporated from hexane to give Q as a colorless foam (1.1 g).

Reaction 5

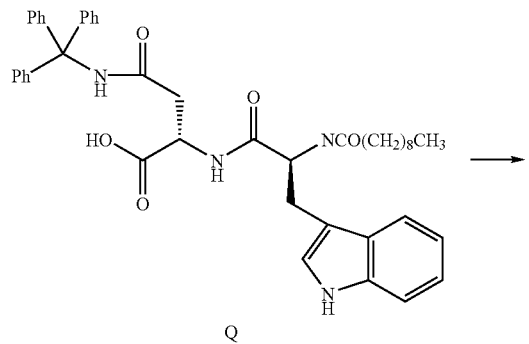

Q

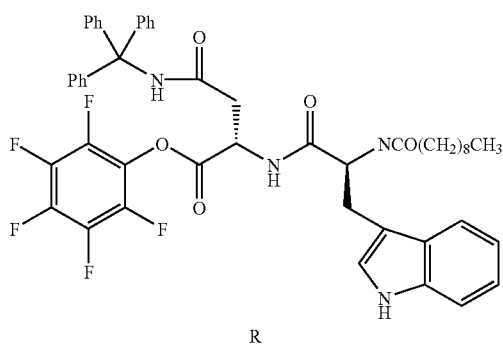

R

To compound Q (0.50 g) and pentafluorophenol (0.13 g) in dry tetrahydrofuran (6 ml) was added dicyclohexylcarbodiimide (0.14 g). The reaction mixture was stirred at room temperature for 2 hours then diluted with hexanes (6 ml) and filtered. The filtrate was evaporated to dryness to give compound R as a colorless oil (0.64 g).

Example 4

Synthesis of Compound U

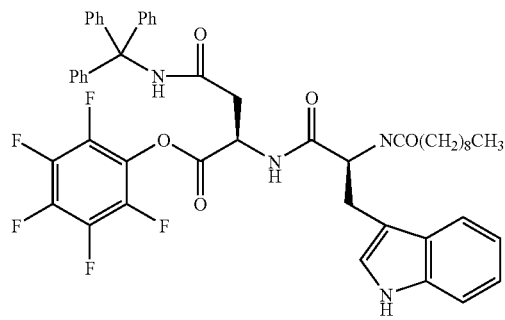

U

Reaction 1

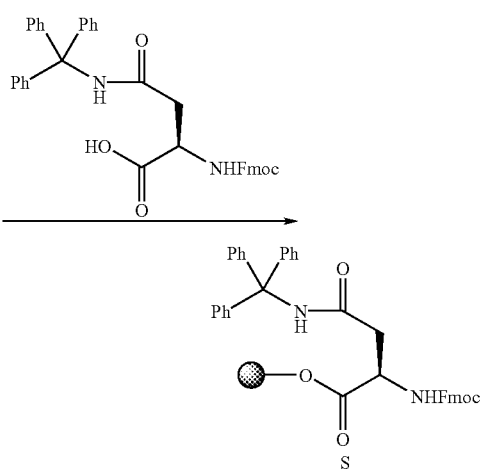

S

Commercially available trityl protected N-Fmoc-D-Asparagine (4.04 g) was suspended in dry dichloromethane (37 ml). Diisopropylethylamine (4.7 ml) was added followed by 2-Cl-Trityl resin (3.7 g 1.4 mmol/g substitution; Advanced ChemTech: Louisville, Ky.). The suspension was stirred for two hours at room 10 temperature, before being filtered. The resin was washed with dichloromethane: methanol:diisopropylethylamine 51:6:3 (60 ml), dichloromethane (60 ml), N,N'-dimethylformamide (60 ml), and dichloromethane (60 ml) and air dried overnight,. to give trityl protected N-Fmoc-D-Asparagine loaded resin S.

Reaction 2

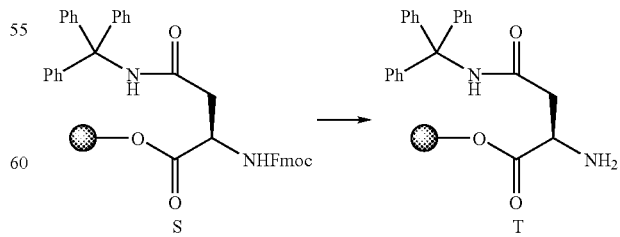

S      T

The terminal Fmoc protecting group of resin S was then removed using the general procedure B above to give resin T.

Compound U was obtained by repeating reactions 1–5 as for the synthesis of compound R by substituting resin M from reaction 1 with resin T obtained from reaction 2 above.

Using Examples 1–4 above, compounds V, W, X and Y can be prepared in a similar manner:

(a) Substituting D-tryptophan ester (e.g. methyl- or-ally-ester) for L-tryptophan t-butyl ester hydrochloride in Example 1 will produce compound V.

V

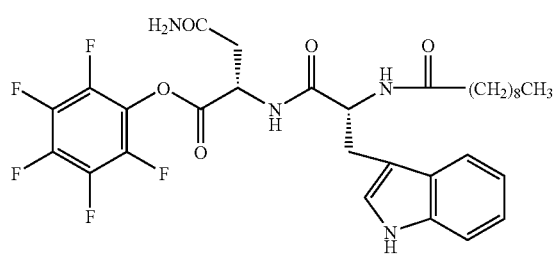

(b) Substituting D-tryptophan ester (e.g. methyl- or-ally-ester) for L-tryptophan benzyl ester in Example 2 will produce compound W.

W

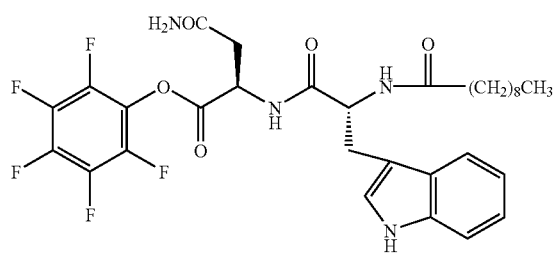

(c) Substituting D-tryptophan ester (e.g. methyl- or-ally-ester) for Fmoc protected-L-tryptophan in Example 3 will produce compound X.

X

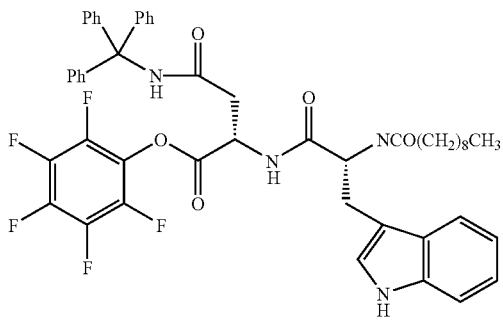

(d) Substituting D-tryptophan ester (e.g. methyl- or-ally-ester) for Fmoc protected-L-tryptophan in Example 4 will produce compound Y.

Y

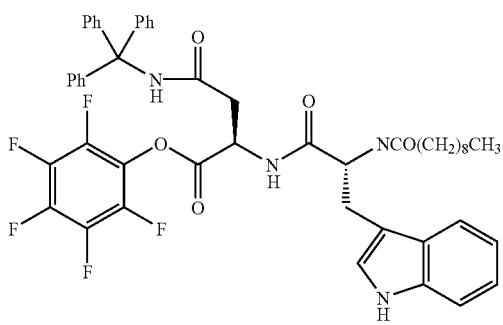

Process

Example 5

Synthesis of Alloc Protected Daptomycin: Compound Z

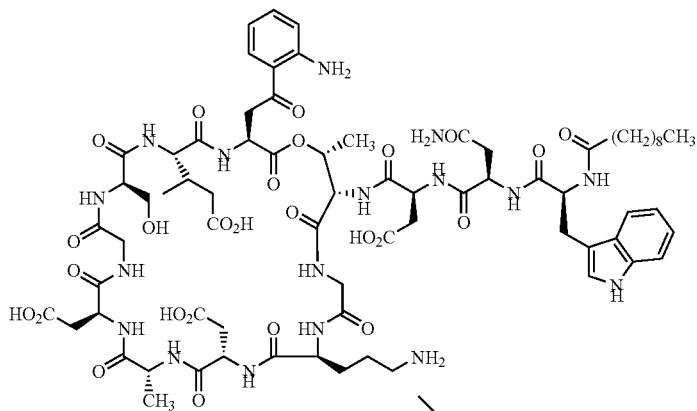

-continued

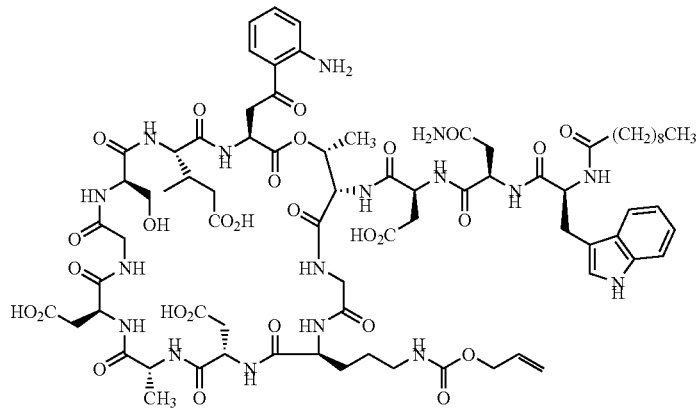

Z

To a solution of daptomycin (10 g) in dry N,N'-dimethylformamide (40 ml) at 0° C. was added allyl-1-benzotriazolylcarbonate (13.5 g). The reaction mixture was allowed to warm up to room temperature and stirred for 18 hours. The mixture was diluted with water (200 ml) then loaded on Bondesil 40μM C8 resin (400 g) that had been prewashed with methanol (1 L) and water (1 L). The resin was washed with water (1 L) and the product was eluted with methanol (1 L). Evaporation of the methanol gave compound Z as a yellow solid (1 g).

Example 6

Preparation of Deacylated Alloc Protected Compound AA

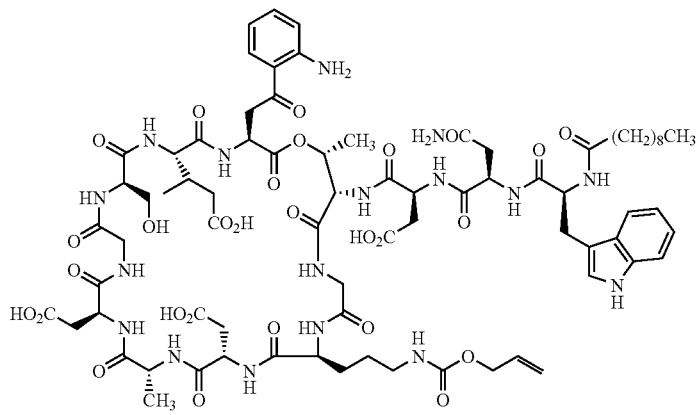

Z

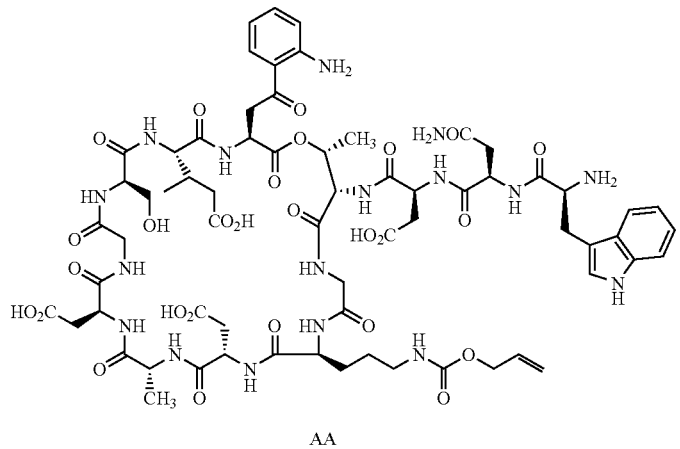

AA

A preparation of deacylase enzyme was produced from recombinant *Streptomyces lividans*, which expresses the *Actinoplanes utahensis* deacylase enzyme. The enzyme in aqueous ethylene glycol (10 ml) was added to a solution of compound Z (15 g in water; 1.9 L) at pH 8. The reaction mixture was stirred at room temperature for 18 hours and the pH was adjusted to 8 using 1 M sodium hydroxide. The reaction mixture was poured on to Bondesil 40 μM C8 resin (400 g) that had been prewashed with methanol (1 L) and water (1 L). The product was eluted with 20% acetonitrile in water (1 L) and freeze-dried to give compound AA as a yellow solid (9.1 g).

Example 7

Edman Degradation to Remove Tryptophan Preparation of Compound BB

Reaction 1

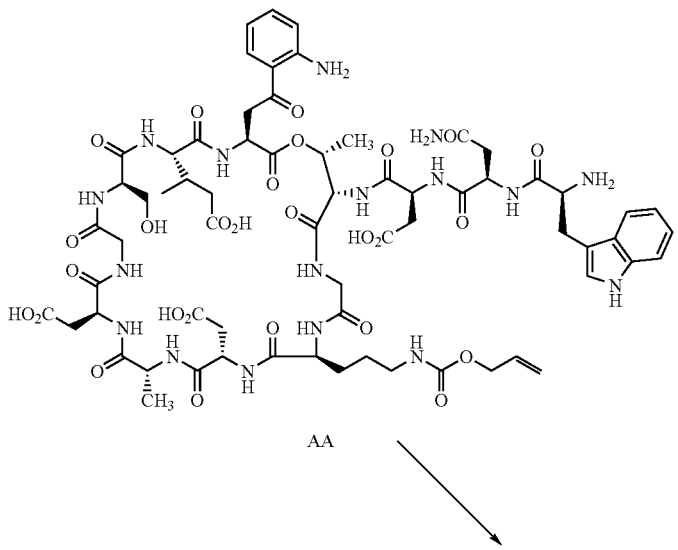

AA

-continued

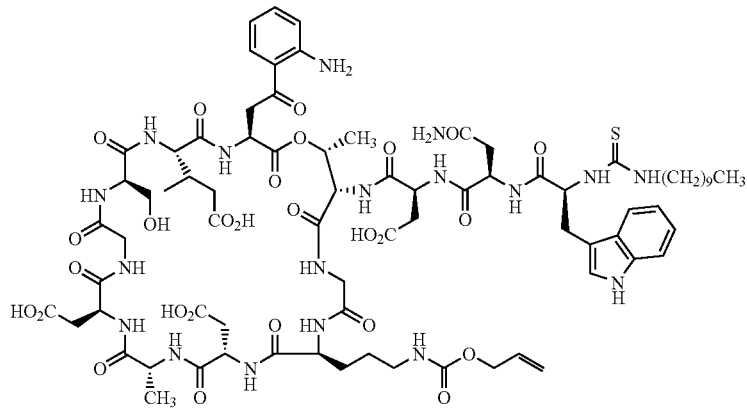

BB

To a suspension of compound AA (9.1 g) in dry N,N'-dimethylformamide (15 ml) was added n-decylisothiocyanate (1.2 ml). The reaction mixture was stirred at room temperature for 18 hours. The reaction mixture was poured on to Bondesil 40 μM C8 resin (400 g) that had been prewashed with methanol (1 L) and water (1 L). The product was eluted with methanol (800 ml) after being first washed with water (800 ml) followed by 20% acetonitrile in water (800 ml). Evaporation of the methanol gave compound BB as a yellow solid (7.3 g).

Reaction 2

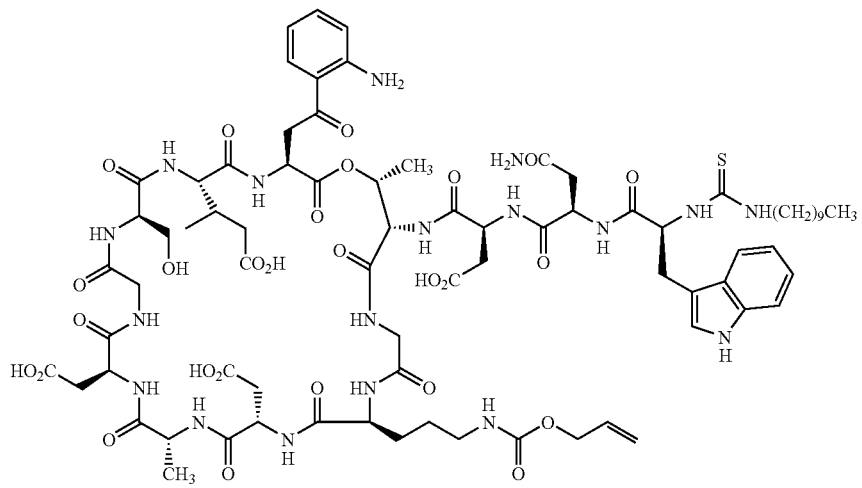

BB

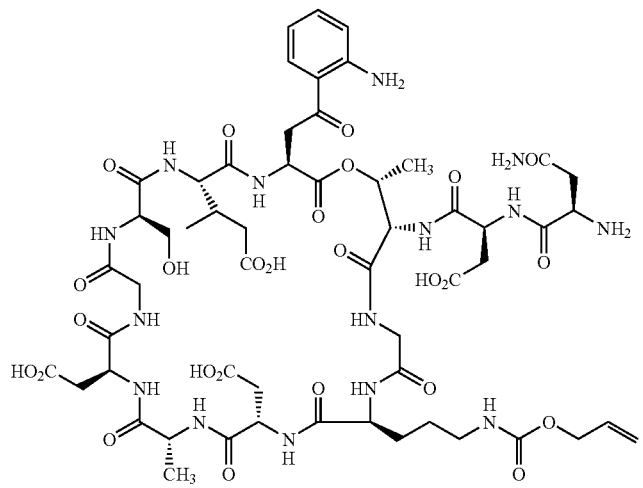

CC

Compound BB (7.3 g) was stirred at room temperature in 25% trifluoroacetic acid in dry dichloromethane (30 ml) for 2 hours before being evaporated to dryness. The residue was dissolved in water (50 ml) poured on to Bondesil 40 μM C8 resin (400 g) that had been prewashed with methanol (1 L) and water (1 L). The product was eluted with a 20 to 40% acetonitrile in water gradient and freeze-dried to give compound CC as a yellow solid (1.05 g).

Example 8

Edman Degradation to Remove Asparagine Preparation of Desasparagine Compound EE

Reaction 1

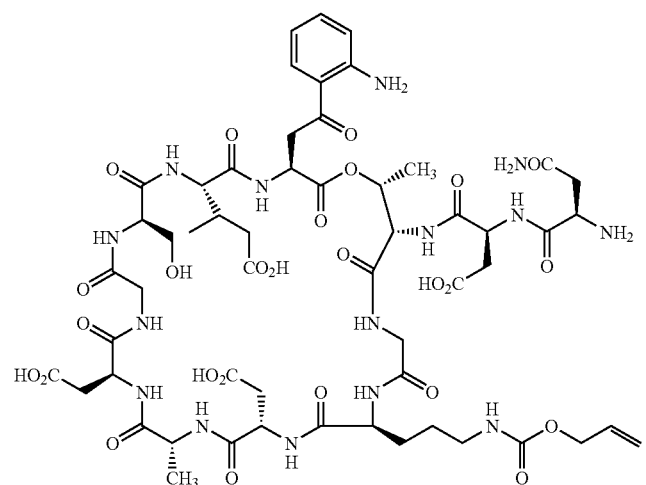

CC

-continued
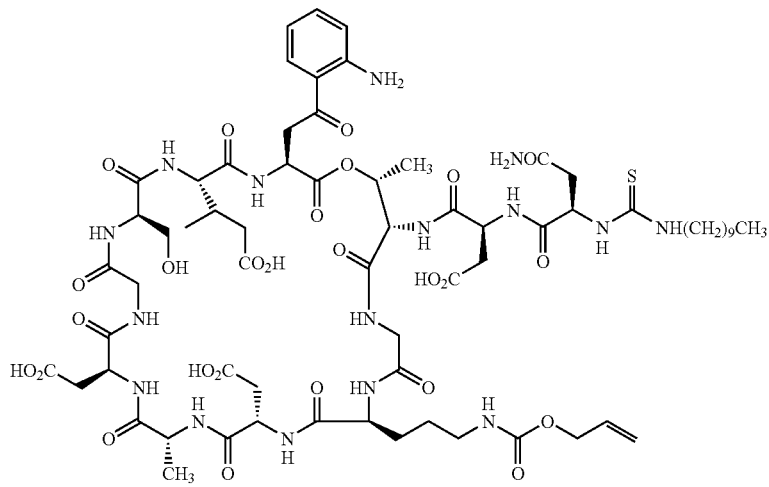
DD
To a suspension of compound CC (0.57 g) in dry N,N'-dimethylformamide (5 ml) was added n-decylisothiocyanate (0.16 ml). The reaction mixture was stirred at room temperature for 18 hours before evaporation to dryness. The residue was tritrated with diethylether (5 ml) to give compound DD as a yellow solid (0.54 g).
Reaction 2
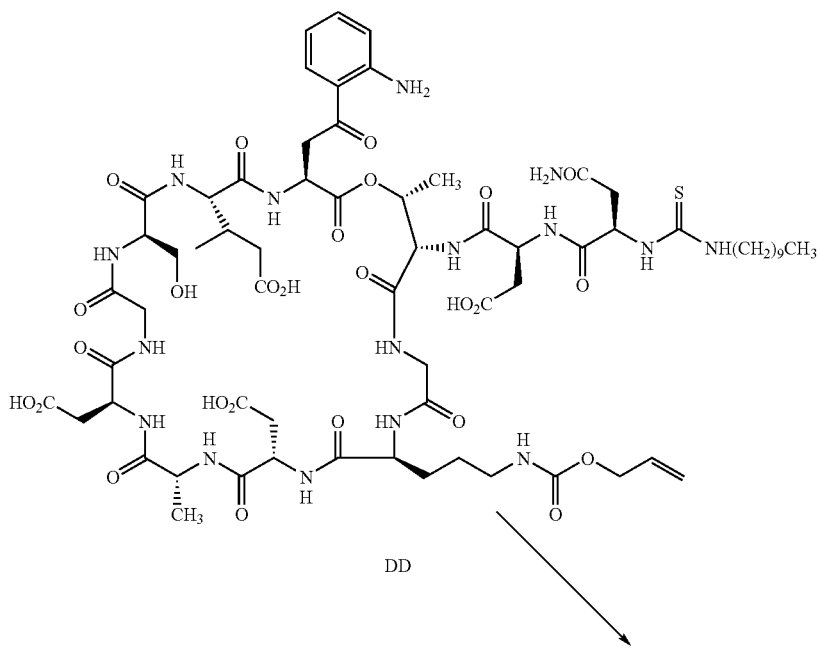
DD -continued

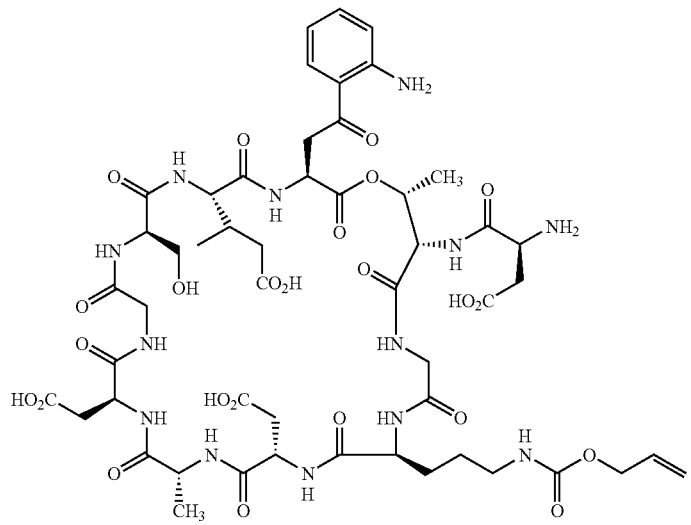

EE

Compound DD (0.54 g) was stirred in 50% trifluoroacetic acid in dry dichloromethane (4 ml) for 2 hours before evaporation to dryness. The residue was dissolved in water (25 ml) poured on to Bondesil 40 μM C8 resin (50 g) that had been prewashed with methanol (100 ml) and water (100 ml). The product was eluted with 20% acetonitrile in water after first being washed with water (100 ml). The eluent was evaporated to dryness to give compound EE as a yellow solid (0.40 g).

Example 9

Acylation and Deprotection to Give Daptomycin Stereoismeric Compound HH

Reaction 1

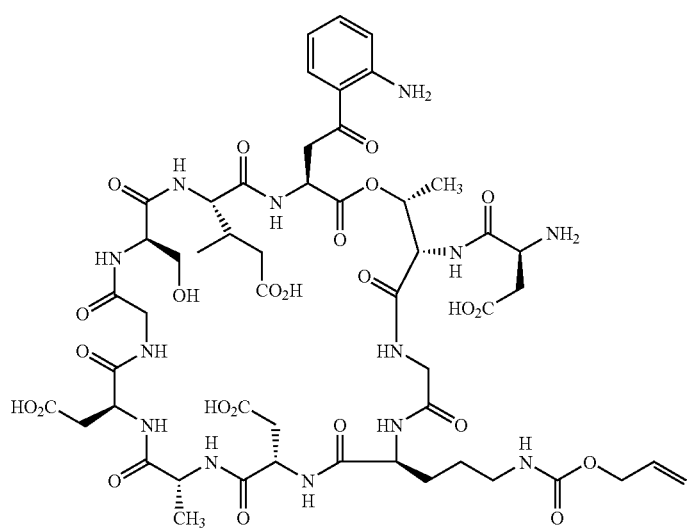

EE

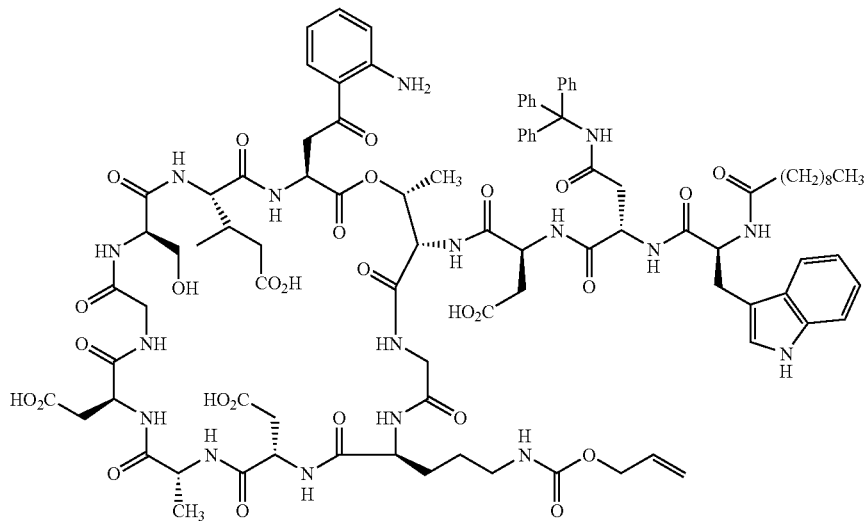
FF
To compound EE (0.1 g) was added compound R (0.85 g) in dry N,N'-dimethylformamide (1.0 ml). The reaction mixture was stirred at room temperature for 18 hours before being evaporated to dryness. The residue was triturated with diethylether (5 ml) to give compound FF as a yellow powder (0.144 g).
Reaction 2
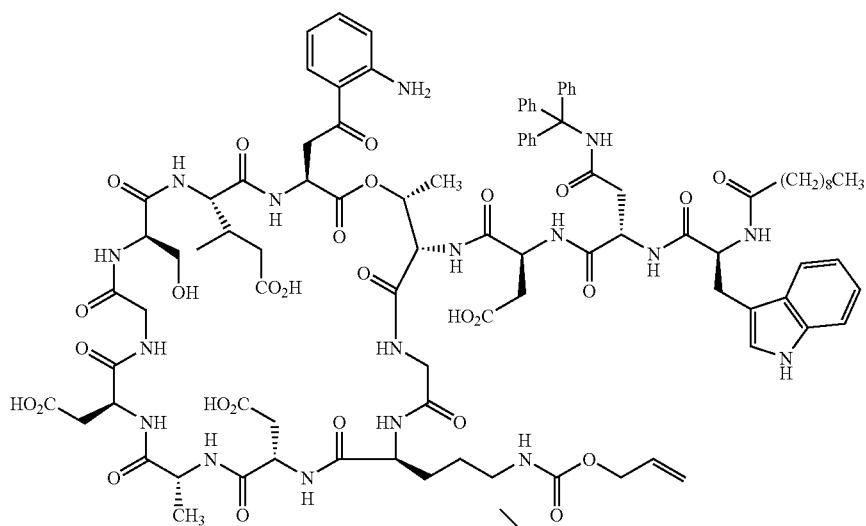
FF -continued

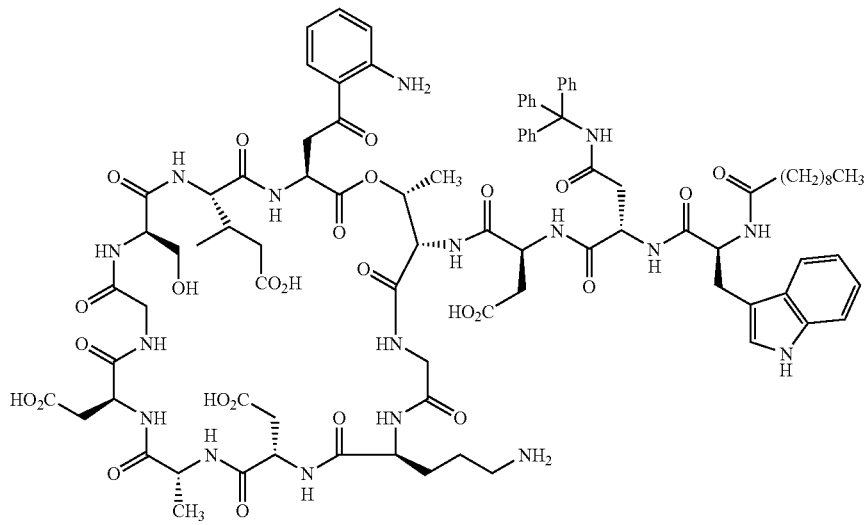

GG

To compound FF (0.144 g) in 0.5 M hydrochloric acid (1.0 ml) and 1,4-dioxane (3.0 ml) was added N-methylmorpholine (0.1 ml) followed by tetrakis-(triphenylphosphine)palladium(0) (0.1 g). The reaction mixture was stirred at room temperature for 24 hours under argon before being filtered. The filtrate was concentrated to a semi-dry solid of crude compound GG (0.4 g) which was used in the next step without further purification.

Reaction 3

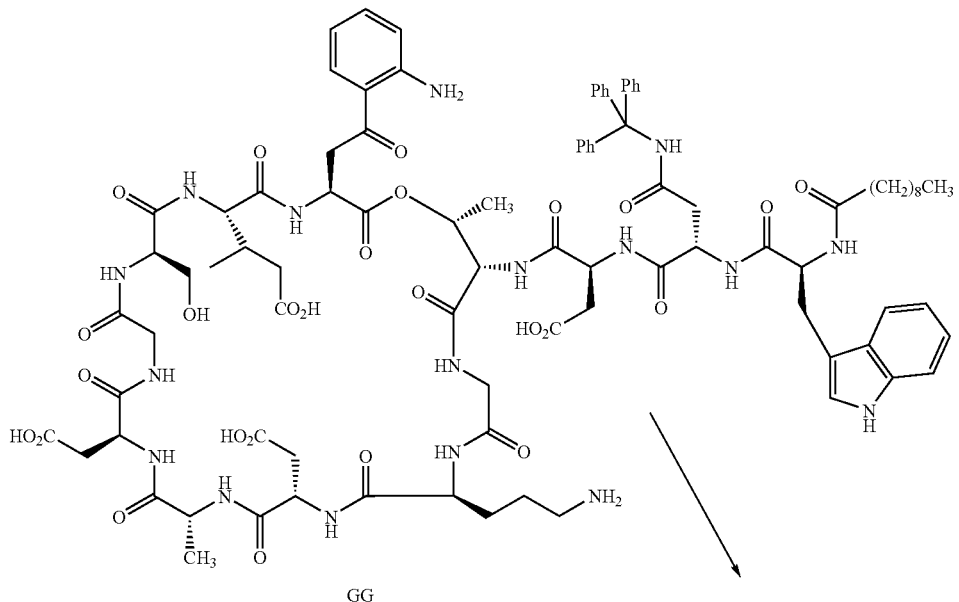

GG

-continued

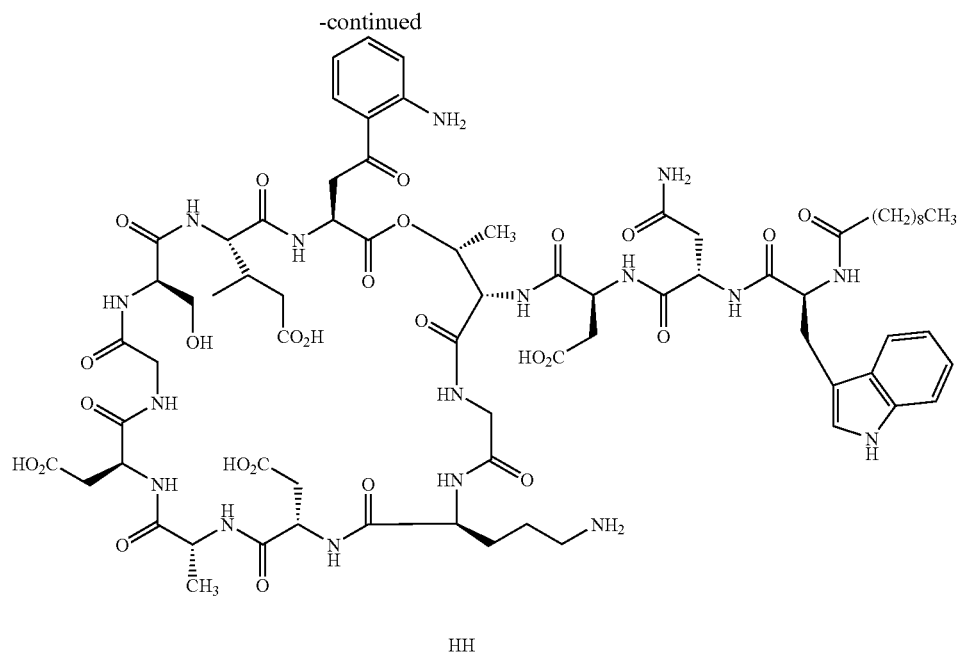

HH

Compound GG (0.2 g) and triisopropylsilane (0.1 ml) were stirred in 25% trifluoroacetic acid in dry diclo-romethane (4.0 ml) at room temperature for 2 hours before being evaporated to dryness. The residue was purified by preparative HPLC with a 250×21.2 mm IBSIL 5μ C8 column using a 20–60% acetonitrile in 0.5% ammonium hydrogenphosphate buffer as eluent. The acetonitrile was evaporated from the collected fractions and the remaining solution was loaded onto Bondesil 40 μM C8 resin (1 g) that had been prewashed with methanol (10 ml) and water (10 ml) and washed with water (10 ml). Then the product was then eluted with methanol (20 ml) and evaporated to dryness to give daptomycin stereoisomeric compound HH as a yellow solid (1.0 mg).

Example 10

Acylation and Deprotection to Give Daptomycin

Reaction 1

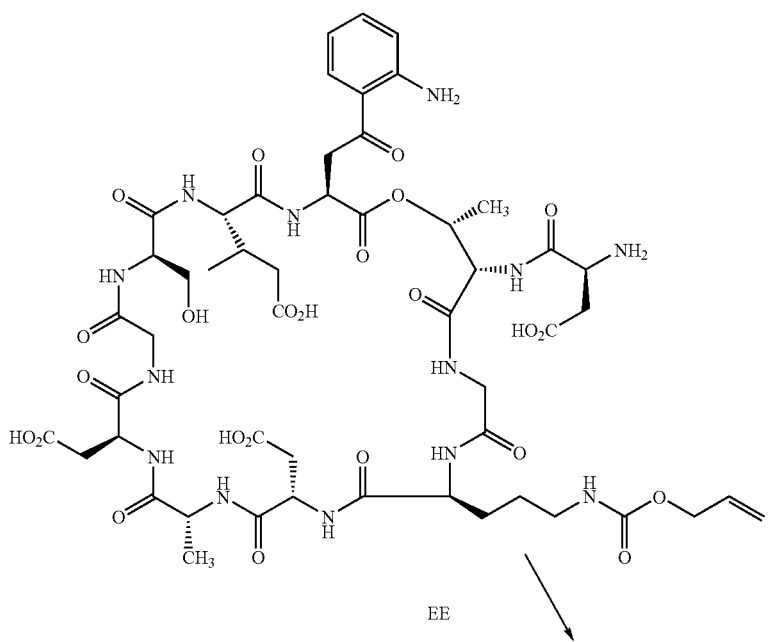

EE

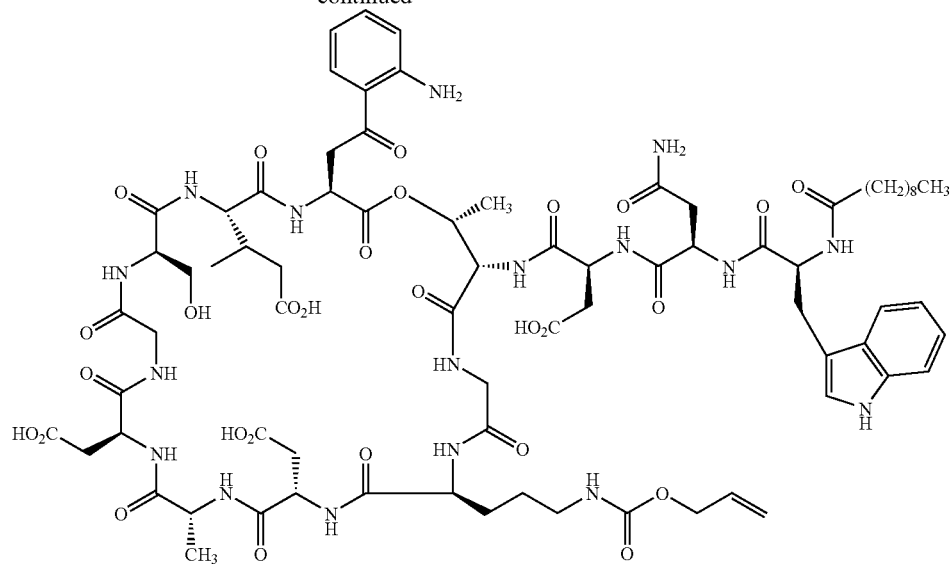
JJ
To compound L in dry N,N'-dimethylformide (1 ml) was added compound EE (50 mg). The reaction mixture was stirred at room temperature for 24 hours before being evaporated to dryness. The residue was triturated with diethylether (5 ml) to give compound JJ as a light yellow powder. Compound JJ was used in the next step without further purification.
Reaction 2
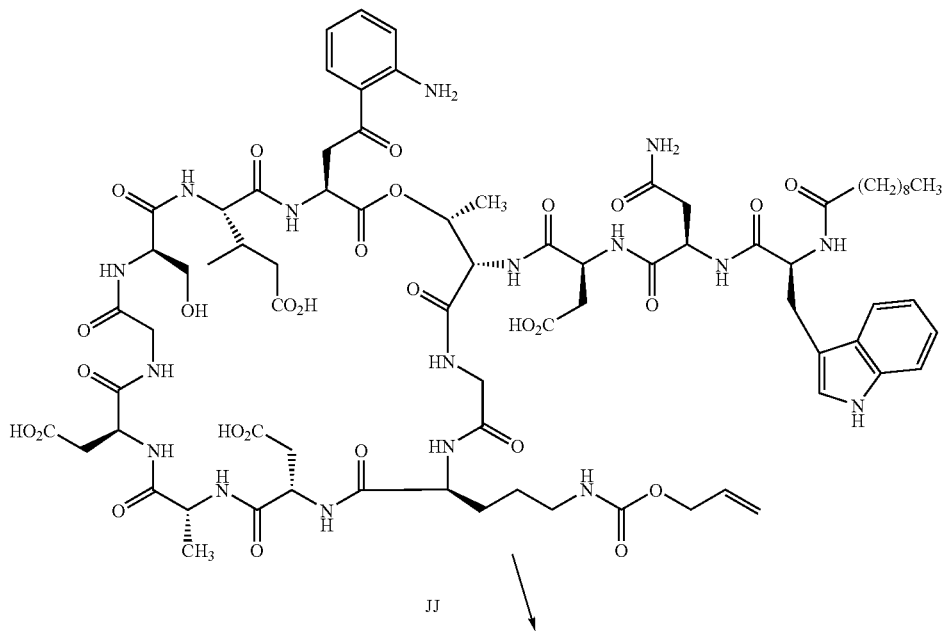
JJ -continued

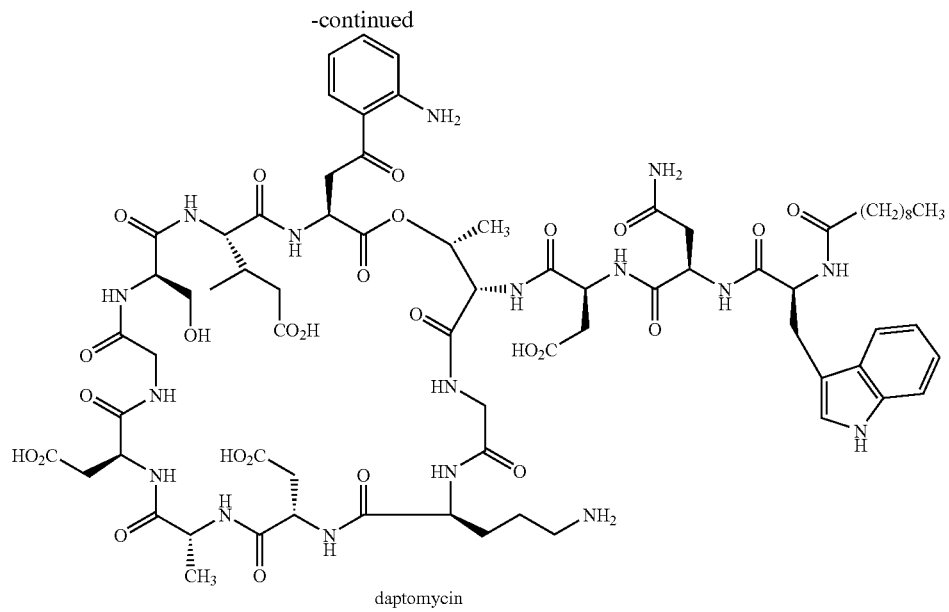

daptomycin

To crude compound JJ from reaction 1 in 0.5 M hydrochloric acid (1 ml) and 1,4-dioxane (3 ml) was added N-methylmorpholine (0.1 ml) followed by tetrakis(triphenylphosphine)palladium(0) (50 mg). The reaction mixture was stirred at room temperature under argon for 24 hours before it was filtered. The filtrate was concentrated to give a residue, which was purified by preparative HPLC with a 250×21.2 mm IBSIL 5µ C8 column using a 20%–60% acetonitrile in 0.5% ammonium hydrogenphosphate buffer as eluent. The acetonitrile was evaporated from the collected fractions and the remaining solution was loaded onto Bondesil 40µM C8 resin (1 g) that had been prewashed with methanol (10 ml) and water (10 ml) and washed with water (10 ml). The product was eluted with methanol and evaporated to dryness to give Daptomycin as a light yellow solid (0.7 mg).

Example 11

Biological Activity

Compounds according to Formula II were tested for antimicrobial activity against a panel of organisms according to standard procedures described by the National Committee for Clinical Laboratory Standards (NCCLS document M7-A5, Vol. 20, No. 2, 2000) except that all testing was performed at 37° C. Compounds were dissolved in 100% dimethyl sulfoxide and were diluted to the final reaction concentration (0.1 µg/mL-100 µg/mL) in microbial growth media. In all cases the final concentration of dimethyl sulfoxide incubated with cells is less than or equal to 1%. For minimum inhibitory concentration (MIC) calculations, 2-fold dilutions of compounds were added to wells of a microtiter plate containing 5×10$^4$ bacteria cells in a final volume of 100 µL of media (Mueller-Hinton Broth supplemented with 50 mg/L Ca$^{2+}$). The optical densities (OD) of the bacterial cells, which measures bacterial cell growth and proliferation, were measured using a commercial plate reader. The MIC value is defined as the lowest compound concentration inhibiting growth of the test organism. The MIC (in µg/ml) value of representative compounds of the present invention are listed in Table I.

TABLE I

| Compound # | MIC (µg/ml) S. aureus | MIC (µg/ml) E. faecalis |
| --- | --- | --- |
| HH | 6.25 | 100 |
| Daptomycin | 0.78 | 6.26 |

Example 12

In Vivo Activity

The mouse protection test is an industry standard for measuring the efficacy of a test compound in vivo [for examples of this model see J. J. Clement, et al., *Antimicrobial Agents and Chemotherapy,* 38 (5), 1071–1078, (1994)]. As exemplified below, this test is used to demonstrate the in vivo efficacy of the compounds of the present invention against bacteria.

The in vivo antibacterial activity is established by infecting female CD-1 mice (Charles River Lab, MA) weighing 19–23 g intraperitoneally with Methicillin Resistant *S. aureus* (MRSA) inoculum. The inoculum is prepared from Methicillin Resistant *S. aureus* (ATCC 43300). The MRSA inoculum is cultured in Mueller-Hinton (MH) broth at 37° C. for 18 hours. The optical density at 600 nm (OD$_{600}$) is determined for a 1:10 dilution of the overnight culture. Bacteria (8×10$^8$ cfu) is added to 20 ml of phosphate buffered saline (Sigma P-0261) containing 5% hog gastric mucin (Sigma M-2378). All animals are injected with 0.5 ml of the inoculum, equivalent to 2×10$^7$ cfu/mouse, which is the dose causing ~100% death of the animals without treatment.

The test compound is dissolved in 10.0 ml of 50 mM phosphate buffer to give a solution of 1 mg/ml (pH=7.0). This solution is serially diluted with vehicle by 4-fold (1.5 ml to 6.0 ml) to give 0.25, 0.063 and 0.016 mg/ml solutions. All the solutions are filtered with 0.2 m Nalgene syringe filter. Immediately after the bacterial inoculation, group 1 animals are subcutaneously (sc) injected with buffer (no test compound) and groups 2 to 5 were given test compound sc

What is claimed is:

1. A composition comprising a compound having the following structure:

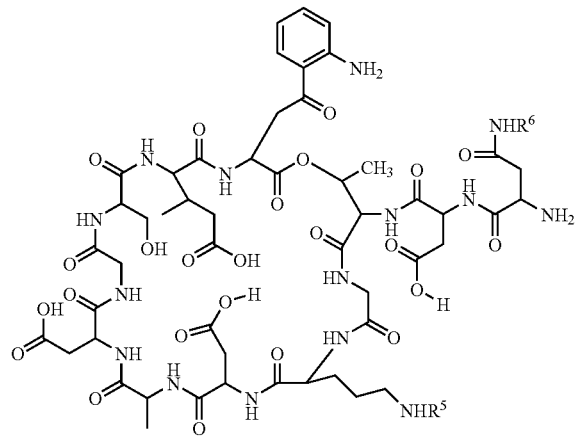

where $R^5$ is an ornithine protecting group and $R^6$ is hydrido or an asparagine protecting group.

2. The composition of claim 1, wherein the compound comprises the following stereochemistry:

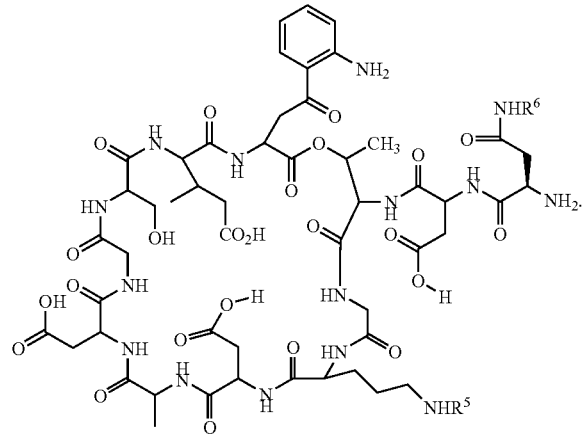

3. The composition of claim 1, wherein the compound comprises the following stereochemistry:

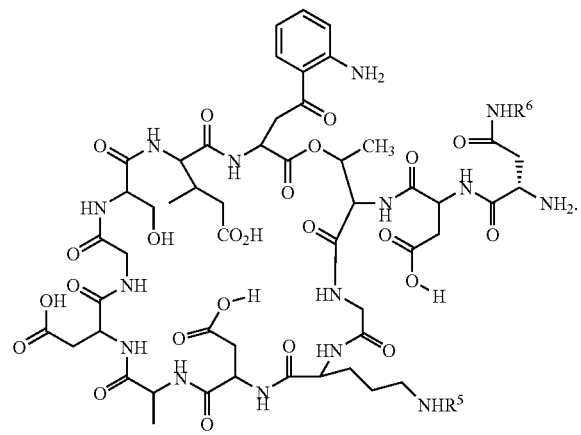

4. The composition of any one of claims 1, 2, or 3, wherein $R^5$ is allyloxycarbonyl, carbobenzyloxycarbonyl or tert-butoxycarbonyl.

5. The composition of claim 4, wherein $R^5$ is allyloxycarbonyl.

6. The composition of claim 5, wherein $R^6$ is hydrido.

7. A composition comprising a compound having the following structure:

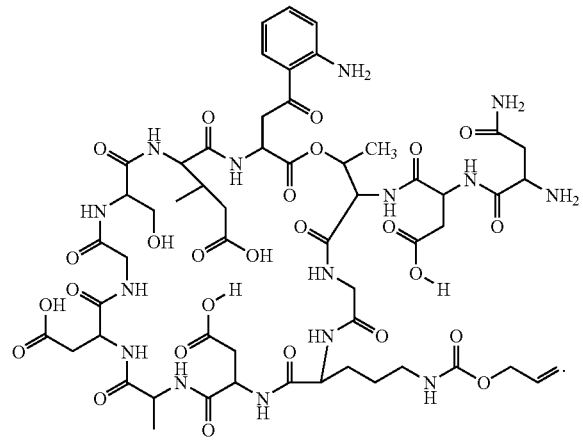

* * * * *